United States Patent
Yamaguchi et al.

(10) Patent No.: US 7,896,931 B2
(45) Date of Patent: Mar. 1, 2011

(54) HAIR DYE COMPOSITION

(75) Inventors: Masakazu Yamaguchi, Sumida-ku (JP); Osamu Takiguchi, Sumida-ku (JP); Masaaki Tsukase, Kanagawa (JP); Yasuhiro Ishiwata, Kanagawa (JP)

(73) Assignees: Kao Corporation, Tokyo (JP); FUJIFILM Corporation, Tokyo (JP)

( * ) Notice: Subject to any disclaimer, the term of this patent is extended or adjusted under 35 U.S.C. 154(b) by 0 days.

(21) Appl. No.: 12/598,790

(22) PCT Filed: Jun. 27, 2008

(86) PCT No.: PCT/JP2008/062121
§ 371 (c)(1), (2), (4) Date: Nov. 4, 2009

(87) PCT Pub. No.: WO2009/005139
PCT Pub. Date: Jan. 8, 2009

(65) Prior Publication Data
US 2010/0146716 A1 Jun. 17, 2010

(30) Foreign Application Priority Data

| Jun. 29, 2007 | (JP) | 2007-173495 |
| Jun. 29, 2007 | (JP) | 2007-173496 |
| Jun. 29, 2007 | (JP) | 2007-173497 |
| Jun. 29, 2007 | (JP) | 2007-173498 |
| Jun. 29, 2007 | (JP) | 2007-173499 |

(51) Int. Cl.
*A61Q 5/10* (2006.01)

(52) U.S. Cl. .......... 8/405; 8/406; 8/437; 8/462; 8/466; 8/565; 8/567; 8/568; 8/570; 8/572; 8/575

(58) Field of Classification Search .......... 8/405, 8/437, 462, 466, 565, 566, 567, 568, 570, 8/571, 572, 575, 406
See application file for complete search history.

(56) References Cited

U.S. PATENT DOCUMENTS

| 7,056,355 B2 | 6/2006 | Pratt et al. |
| 7,476,261 B2 | 1/2009 | Yamaguchi et al. |
| 2004/0019982 A1 | 2/2004 | Pratt et al. |
| 2005/0015896 A1 | 1/2005 | Pratt et al. |
| 2008/0134448 A1 | 6/2008 | Yamaguchi et al. |

FOREIGN PATENT DOCUMENTS

| EP | 1 366 752 | | 12/2003 |
| EP | 1 398 020 | | 3/2004 |
| EP | 1 832 276 | | 9/2007 |
| JP | 2001 214084 | | 8/2001 |
| JP | 2001214084 | * | 8/2001 |
| JP | 2004-107343 | | 4/2004 |
| JP | 2005 162855 | | 6/2005 |
| JP | 2005 171079 | | 6/2005 |
| JP | 2006-182653 | | 7/2006 |

OTHER PUBLICATIONS

STIC Search Report dated Jul. 12, 2010.*
Clarence R. Robbins, "Chemical and Physical Behavior of Human Hair", 4th Ed., Springer-Verlag, 2002, pp. 331-334.
Mohareb, R. M. et al., "Thiophenylhydrazonoacetates in Heterocyclic Synthesis", Retrieved from the Internet URL: http:// www3.interscience.wiley.com/cgi-bin/fulltext/107061169/PDFSTART>, Heteroatom Chemistry, vol. 15, No. 1 pp. 15-20 (2004) XP002500409.

* cited by examiner

*Primary Examiner*—Eisa B Elhilo
(74) *Attorney, Agent, or Firm*—Oblon, Spivak, McClelland, Maier & Neustadt, L.L.P.

(57) ABSTRACT

The present invention relates to a hair dye composition containing a dissociative azo dye which has high dyeing power, is capable of imparting a vivid color to the hair firmly, has excellent fastness to light, shampooing, sweat, friction, and heat, and fades less with the passage of time because the dye is stable against an alkali agent or an oxidizing agent and does not decompose during hair dyeing; and a hair dyeing method using the hair dye composition.

14 Claims, No Drawings

HAIR DYE COMPOSITION

FIELD OF THE INVENTION

The present invention relates to a hair dye composition containing an azo dye.

BACKGROUND OF THE INVENTION

Typical examples of hair dye compositions include two-part permanent hair dyes composed of a first part containing an alkali agent, an oxidation dye and optionally, a direct dye such as nitro dye and a second part containing an oxidizing agent; and one-part semi-permanent hair dyes containing an organic acid or an alkali agent, and at least one direct dye such as acid dye, basic dye or nitro dye.

Permanent hair dyes however have the drawback that their color tone produced by an oxidation dye is not so vivid. It is the common practice to try to produce vivid color by using a direct dye and an oxidation dye in combination. Direct dyes, particularly nitro dyes, however have the problem that color of the hair dyed with them fades considerably and very vivid color tone of the hair just after dyeing is lost rapidly.

Direct dyes usable in combination with oxidation dyes are limited because they are required to be stable against peroxides during the hair dyeing process.

Various acid dyes, basic dyes, and nitro dyes to be added to permanent dyes or semi-permanent dyes are apt to fade in any case because direct dyes on the hair are lost relatively easily by shampooing or exposure to light. Such a tendency is marked in the damaged hair.

For improving resistance (fastness) to light, shampooing, sweat, friction, or heat, a hair dye using a direct dye having a dissociative proton is proposed (refer to Patent Documents 1 and 2). In hair dyes using direct dyes, however, a good balance in dyeing property or fading property between the root and tip of the hair tends to be achieved by mixing a plurality of dyes having the same hue (refer to Non-Patent Document 1) so that there is a demand for the development of dissociative azo dyes different in the structural characteristics.

[Patent Document 1] JP-A-2004-107343
[Patent Document 2] JP-A-2006-182653
[Non-Patent Document 1] Clarence R. Robbins, *Chemical and Physical Behavior of Human Hair*, 4th Ed., pp 331-334, Springer-Verlag, 2002

SUMMARY OF THE INVENTION

In the present invention, there is provided a hair dye composition containing a dissociative azo dye represented by any one of the following formulas (1) to (5):

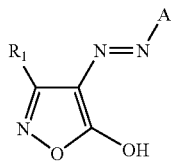
(1)

[wherein, $R_1$ represents a hydrogen atom or a substituent and A represents a monocyclic or bicyclic, aromatic heterocyclic residue which may have a substituent and has a free valence at a carbon atom of the residue, with the proviso that $R_1$ and A each contains, in the structure thereof, none of a carboxy group, a sulfo group and a quaternary ammonium group],

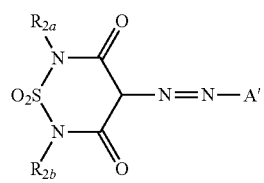
(2)

[wherein, $R_{2a}$ and $R_{2b}$ each represents a hydrogen atom or a substituent, and A' represents a monocyclic or bicyclic, aromatic heterocyclic residue which may have a substituent and has a free valence at a carbon atom of the residue, with the proviso that $R_{2a}$, $R_{2b}$, and A' each contains, in the structure thereof, none of a carboxy group, a sulfo group, and a quaternary ammonium group,

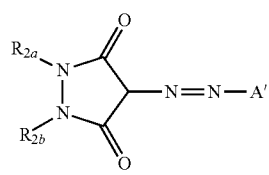
(3)

[wherein, $R_{2a}$, $R_{2b}$, and A' have the same meanings as described above],

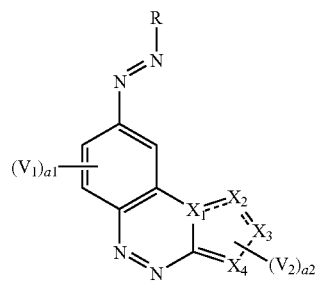
(4)

[wherein, R represents a coupler component, $X_1$, $X_2$, $X_3$, and $X_4$ represent atoms which are coupled together with the carbon atom sandwiched between $X_1$ and $X_4$ to form a 5-membered heteroaromatic ring, $V_1$ and $V_2$ each represents a substituent, and a1 and a2 each stands for an integer from 0 to 3], and

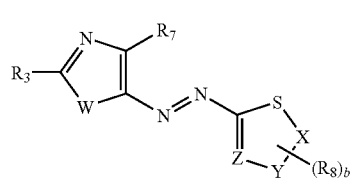
(5)

[wherein, $R_3$ represents a hydroxy group, an alkylsulfonylamino group, an arylsulfonylamino group, or —CH($R_4$)($R_5$)

($R_4$ and $R_5$ each representing a substituent having a Hammett's constant σ of 0.2 or greater and less than 1.4), W represents a sulfur atom or N—$R_6$ ($R_6$ representing a substituent), X, Y and Z each represents a nitrogen atom or a carbon atom, with the proviso that at least one of X, Y and Z is a nitrogen atom and when Z represents a nitrogen atom, either one or both of X and Y represent a nitrogen atom, $R_7$ and $R_8$ each represents a substituent, and b stands for from 0 to 2, with the proviso that when b stands for 2, two $R_{8s}$ may be coupled to form an aromatic ring or a heteroaromatic ring].

In the present invention, there is also provided a hair dyeing method including applying the above-described hair dye composition to the hair.

MODE FOR CARRYING OUT THE INVENTION

The present invention relates to a hair dye composition containing a dissociative azo dye which has high dyeing power, is capable of imparting a vivid color to the hair firmly, has excellent fastness to light, shampooing, sweat, friction, and heat, and fades less with the passage of time because the dye is stable against an alkali agent or an oxidizing agent and does not decompose during hair dyeing; and a hair dyeing method using the hair dye composition.

The term "hair dye composition" as used herein embraces not only a one-part composition, but also a two-part composition composed of a first part containing an alkali agent and a second part containing an oxidizing agent which are stored separately just before use, and a multi-part composition such as a three-part composition composed of, in addition to the first part and the second part, a third part containing an oxidation aid. The term "whole composition" means a mixture of all the parts which is applied to the hair in practice. The term "substituent" as used herein means a group which can be substituted for a hydrogen atom.

Dissociative Azo Dyes Represented by the Formula (1)

Examples of when $R_1$ in the formula (1) is not a hydrogen atom, $R_1$ includes:

halogen atoms (such as a fluorine atom, a chlorine atom, and a bromine atom), a hydroxy group, an amino group, a mercapto group, alkyl groups (linear, branched, or cyclic alkyl groups having from 1 to 15, preferably from 1 to 6 carbon atoms, such as a methyl group, an ethyl group, an n-propyl group, an isopropyl group, an s-butyl group, a t-butyl group, an n-octyl group, a 2-ethylhexyl group, a cyclopentyl group, and a cyclohexyl group), alkenyl groups (linear, branched, or cyclic alkenyl groups having from 2 to 10, preferably from 2 to 6 carbon atoms, such as a vinyl group, an allyl group, a prenyl group, and a cyclopenten-1-yl group), alkynyl groups (alkynyl groups having from 2 to 10, preferably from 2 to 6 carbon atoms, such as an ethynyl group and a propargyl group), aryl groups (aryl groups having from 6 to 16, preferably from 6 to 10 carbon atoms, such as a phenyl group, an o-tolyl group, a p-tolyl group, and a naphthyl group), heterocyclic groups (monovalent groups having from 1 to 12, preferably from 2 to 6 carbon atoms, which are available by removing a hydrogen atom from 5- to 10-membered, preferably from 5- or 6-membered aromatic or non-aromatic heterocyclic compounds, such as a 1-pyrazolyl group, a 1-imidazolyl group, a 2-furyl group, a 2-thienyl group, a 4-pyrimidinyl group, a 2-pyridyl group, a 2-benzothiazolyl group, a 2-tetrahydrofuryl group, and a 2-morpholyl group)

a nitro group, a cyano group, a carbamoyl group, a sulfamoyl group, acyl groups (a formyl group, alkylcarbonyl groups having from 2 to 10, preferably from 2 to 6 carbon atoms, arylcarbonyl groups having from 7 to 12, preferably from 7 to 9 carbon atoms, heterocyclic carbonyl groups having from 2 to 12, preferably from 2 to 6 carbon atoms, such as a formyl group, an acetyl group, a propionyl group, a pivaloyl group, a benzoyl group, and a 2-pyridylcarbonyl group), alkoxycarbonyl groups (alkoxycarbonyl groups having from 2 to 10, preferably from 2 to 6 carbon atoms, such as a methoxycarbonyl group, an ethoxycarbonyl group, a t-butoxycarbonyl group, and an isobutyloxycarbonyl group), aryloxycarbonyl groups (aryloxycarbonyl groups having from 7 to 12, preferably from 7 to 9 carbon atoms, such as a phenoxycarbonyl group and a naphthoxycarbonyl group), heterocyclic oxycarbonyl groups (heterocyclic oxycarbonyl groups having from 1 to 12, preferably from 2 to 6 carbon atoms, such as a 1-pyrazolyloxycarbonyl group, a 1-imidazolyloxycarbonyl group, a 2-furyloxycarbonyl group, a 2-thienyloxycarbonyl group, a 2-tetrahydrofuryloxycarbonyl group, and a 2-morpholyloxycarbonyl group), imido groups (imido groups having from 2 to 10, preferably from 4 to 8 carbon atoms, such as an N-succinimido group and an N-phthalimido group), alkylsulfinyl groups (alkylsulfinyl groups having from 1 to 10, preferably from 1 to 6 carbon atoms, such as a methylsulfinyl group and an ethylsulfinyl group), arylsulfinyl groups (arylsulfinyl groups having from 6 to 12, preferably from 6 to 8 carbon atoms, such as a phenylsulfinyl group), alkylsulfonyl groups (alkylsulfonyl groups having from 1 to 10, preferably from 1 to 6 carbon atoms, such as a methylsulfonyl group, an ethylsulfonyl group, and a cyclohexylsulfonyl group), arylsulfonyl groups (arylsulfonyl groups having from 6 to 12, preferably from 6 to 8 carbon atoms, such as a phenylsulfonyl group), heterocyclic sulfonyl groups (heterocyclic sulfonyl groups having from 1 to 12, preferably from 2 to 6 carbon atoms, such as a 2-tetrahydropyranylsulfonyl group), a phosphanyl group, a phosphoryl group, and a phosphinoyl group.

The examples also include these substituents having one or more substituents. In this case, preferred examples of the one or more substituents include those described above as the substituents. When the number of the substituents is two or more, these substituents may be the same or different.

The following are examples of the substituent having a further substituent. Examples of the alkyl or aryl group having a substituent include:

aralkyl groups (aralkyl groups having from 7 to 18, preferably from 7 to 12 carbon atoms, such as a benzyl group and a phenethyl group), haloalkyl groups (linear, branched, or cyclic haloalkyl groups having from 1 to 15, preferably from 1 to 6 carbon atoms, such as a chloromethyl group, a 2-chloroethyl group, a 2-bromopropyl group, and a 3-bromopropyl group), haloaryl groups (haloaryl groups having from 6 to 12, preferably from 6 to 8 carbon atoms, such as a p-chlorophenyl group, a 2,4-dichlorophenyl group, and a 3-fluorophenyl group), and hydroxyalkyl groups (linear, branched, or cyclic alkyl groups having from 1 to 15, preferably from 1 to 6 carbon atoms, such as a hydroxymethyl group, a 2-hydroxyethyl group, a 2-hydroxypropyl group, and a 3-hydroxypropyl group).

Examples of the hydroxy group having a substituent include:

alkoxy groups (linear, branched, or cyclic alkoxy groups having from 1 to 10, preferably from 1 to 6 carbon atoms, such as a methoxy group, an ethoxy group, an isopropoxy group, a t-butoxy group, and a cyclopentyloxy group), alkenyloxy groups (linear, branched, or cyclic alkenyloxy groups having from 2 to 10, preferably from 2 to 6 carbon atoms, such as a 2-buten-1-yloxy group), aryloxy groups (aryloxy groups having from 6 to 12, preferably from 6 to 10 carbon atoms, such as a phenoxy group, a 2-methylphenoxy group, and a 4-t-butylphenoxy group), silyloxy groups (silyloxy groups having from 3 to 10, preferably from 3 to 6 carbon atoms, such as a trimethylsilyloxy group and a t-butyldimethylsilyloxy group), heterocyclic oxy groups (heterocyclic oxy groups having from 1 to 12, preferably from 2 to 6 carbon atoms, such as a 1-phenyltetrazol-5-oxy group and a 2-tetrahydropyranyloxy group), alkylsulfonyloxy groups (linear, branched, or cyclic alkylsulfonyloxy groups having from 1 to 10, preferably from 1 to 6 carbon atoms, such as a methanesulfonyloxy group and an ethanesulfonyloxy group), arylsulfonyloxy groups (arylsulfonyloxy groups having from 6 to 12, preferably from 6 to 10 carbon atoms, such as a phenylsulfonyloxy group), heterocyclic sulfonyloxy groups (heterocyclic sulfonyloxy groups having from 1 to 12, preferably from 2 to 6 carbon atoms, such as a 2-pyridylsulfonyloxy group), acyloxy groups (acyloxy groups having from 1 to 12, preferably from 1 to 8 carbon atoms, such as a formyloxy group, an acetyloxy group, a pivaloyloxy group, and a benzoyloxy group), carbamoyloxy groups (carbamoyloxy groups having from 1 to 10, preferably from 1 to 6 carbon atoms, such as an N,N-dimethylcarbamoyloxy group, an N,N-diethylcarbamoyloxy group, and a morpholinocarbonyloxy group), alkoxycarbonyloxy groups (alkoxycarbonyloxy groups having from 2 to 10, preferably from 2 to 8 carbon atoms, such as a methoxycarbonyloxy group, an ethoxycarbonyloxy group, a t-butoxycarbonyloxy group, and an n-octyloxycarbonyloxy group), aryloxycarbonyloxy groups (aryloxycarbonyloxy groups having from 7 to 12, preferably from 7 to 10 carbon atoms, such as a phenoxycarbonyloxy group and a p-methoxyphenoxycarbonyloxy group), and dialkylphosphinyloxy groups (phosphinyloxy groups having from 2 to 12, preferably from 2 to 6 carbon atoms, such as a dimethylphosphinyloxy group and a dibutylphosphinyloxy group).

Examples of the amino group having a substituent include:

alkylamino groups (alkylamino groups having from 1 to 20, preferably from 1 to 12 carbon atoms, such as a methylamino group, a dimethylamino group, a cyclohexylmethylamino group, and a 1-pyrrolidyl group), arylamino groups (arylamino groups having from 6 to 16, preferably from 6 to 12 carbon atoms, such as an anilino group, an N-methylanilino group, and a diphenylamino group), heterocyclic amino groups (heterocyclic amino groups having from 1 to 12, preferably from 2 to 6 carbon atoms, such as a 2-pyridylamino group, a pyrazol-4-ylamino group, a benzimidazol-2-ylamino group, a benzothiazol-2-ylamino group, a benzoxazol-2-ylamino group, a 2-oxazolylamino group, a 1,2,4-triazol-3-ylamino group, a 1,2,4-thiadiazol-2-ylamino group, a 1,3,4-thiadiazol-2-ylamino group, a 1,2,4-oxadiazol-2-ylamino group, and a 1,3,4-oxadiazol-2-ylamino group), acylamino groups (alkylcarbonylamino groups having from 1 to 10, preferably from 1 to 6 carbon atoms, arylcarbonylamino groups having from 6 to 18, preferably from 6 to 12 carbon atoms, and heterocyclic carbonylamino groups having from 2 to 12, preferably from 2 to 6 carbon atoms, such as a formylamino group, an acetylamino group, an ethylcarbonylamino group, a pivaloylamino group, a benzoylamino group, and a 4-pyridylcarbonylamino group), ureido groups (aminocarbonylamino groups having from 1 to 12, preferably from 1 to 8 carbon atoms, such as a carbamoylamino group, an N,N-dimethylaminocarbonylamino group, an N,N-diethylaminocarbonylamino group, and a morpholin-4-ylcarbonylamino group), alkoxycarbonylamino groups (alkoxycarbonylamino groups having from 2 to 10, preferably from 2 to 6 carbon atoms, such as a methoxycarbonylamino group, an ethoxycarbonylamino group, and a t-butoxycarbonylamino group), aryloxycarbonylamino groups (aryloxycarbonylamino groups having from 7 to 12, preferably from 7 to 9 carbon atoms, such as a phenoxycarbonylamino group), heterocyclic oxycarbonylamino groups (heterocyclic oxycarbonylamino groups having from 1 to 12, preferably from 2 to 6 carbon atoms, such as a 2-pyridyloxycarbonylamino group), sulfamoylamino groups (sulfamoylamino groups having from 0 to 10, preferably from 0 to 6 carbon atoms, such as a sulfamoylamino group and an N,N-dimethylaminosulfonylamino group), alkylsulfonylamino groups (alkylsulfonylamino groups having from 1 to 10, preferably from 1 to 6 carbon atoms, such as a methylsulfonylamino group, an ethylsulfonylamino group, and an n-butylsulfonylamino group), arylsulfonylamino groups (arylsulfonylamino groups having from 6 to 12, preferably from 6 to 8 carbon atoms, such as a phenylsulfonylamino group), and phosphinylamino groups (phosphinylamino groups having from 2 to 12, preferably from 2 to 6 carbon atoms, such as a dimethoxyphosphinylamino group and a dimethylaminophosphinylamino group).

Examples of the mercapto group having a substituent include:

alkylthio groups (alkylthio groups having from 1 to 10, preferably from 1 to 6 carbon atoms, such as a methylthio group, an ethylthio group, and a butylthio group), arylthio groups (arylthio groups having from 6 to 12, preferably from 6 to 8 carbon atoms, such as a phenylthio group), and heterocyclic thio groups (heterocyclic thio groups having from 1 to 10, preferably from 1 to 6 carbon atoms, such as a 2-benzothiazolylthio group, and a 1-phenyltetrazol-5-ylthio group).

Examples of the carbamoyl group having a substituent include:

alkylcarbamoyl groups (carbamoyl groups having from 1 to 12, preferably from 1 to 8 carbon atoms, such as a methylcarbamoyl group, a dimethylcarbamoyl group, a diethylcarbamoyl group, and a 1-pyrrolidylcarbamoyl group), and sulfamoylcarbamoyl groups (sulfamoylcarbamoyl groups having from 1 to 12, preferably from 1 to 8 carbon atoms, such as an N-(sulfamoyl)carbamoyl group, and an N—(N',N'-dimethylsulfamoyl)carbamoyl group).

Examples of the sulfamoyl group having a substituent include:

alkylsulfamoyl groups (alkylsulfamoyl groups having from 1 to 12, preferably from 1 to 6 carbon atoms, such as an ethylsulfamoyl group, a dimethylsulfamoyl group, a dibutylsulfamoyl group, an ethylmethylsulfamoyl group, a diethylsulfamoyl group, and an N-cyclohexyl-N-methylsulfamoyl group), arylsulfamoyl groups (arylsulfamoyl groups having from 6 to 12, preferably from 6 to 8 carbon atoms, such as a phenylsulfamoyl group), and carbamoylsulfamoyl groups (carbamoylsulfamoyl groups having from 1 to 12, preferably from 1 to 6 carbon atoms, such as an N-(carbamoyl)sulfamoyl group).

Examples of the phosphoryl group having a substituent include:

alkylphosphoryl groups (alkylphosphoryl groups having from 1 to 12, preferably from 1 to 6 carbon atoms, such as a methylphosphoryl group and an ethylphosphoryl group).

Examples of the substituent having a substituent, the latter substituent having a substituent further, include:

alkoxyalkyl groups (linear, branched, or cyclic alkoxyalkyl groups having from 1 to 32, preferably from 1 to 12 carbon atoms, such as a methoxymethyl group, a methoxyethyl group, an ethoxyethyl group, and a cyclohexyloxypropyl group), alkoxyaryl groups (alkoxyaryl groups having from 7 to 18, preferably from 7 to 12 carbon atoms, such as a p-methoxyphenyl group and a 2,4-dimethoxyphenyl group), alkoxycarbonylalkyl groups (alkoxycarbonylalkyl groups having from 2 to 15, preferably from 2 to 6 carbon atoms, such as a methoxycarbonylethyl group and a 3-ethoxycarbonylpropyl group), alkylaminoalkyl groups (alkylamino alkyl groups having from 2 to 15, preferably from 2 to 6 carbon atoms, such as an N-methylaminomethyl group and a dimethylaminoethyl group), alkylthioalkyl groups (alkylthioalkyl groups having from 2 to 15, preferably from 2 to 6 carbon atoms, such as a methylthiomethyl group, a methylthioethyl group, and an ethylthioethyl group), haloalkoxyaryl groups (haloalkoxyaryl groups having from 7 to 18, preferably from 7 to 12 carbon atoms, such as a 2-chloro-4-methoxyphenyl group and a 2,5-dichloro-4-methoxyphenyl group), alkoxycarbonyloxy groups (alkoxycarbonyloxy groups having from 2 to 15, preferably from 2 to 6 carbon atoms, such as a methoxycarbonyloxy group and an ethoxycarbonyloxy group), aryloxycarbonyloxy groups (aryloxycarbonyloxy groups having from 7 to 18, preferably from 7 to 12 carbon atoms, such as a phenoxycarbonyloxy group), alkoxycarbonylamino groups (alkoxycarbonylamino groups having from 2 to 10, preferably from 2 to 6 carbon atoms, such as a methoxycarbonylamino group, an ethoxycarbonylamino group, a t-butoxycarbonylamino group, and an isobutyloxycarbonylamino group), and hydroxyalkylthio groups (hydroxyalkylthio groups having from 1 to 15, preferably from 1 to 6 carbon atoms, such as a hydroxyethylthio group and a 2-hydroxypropylthio group).

Preferred examples of $R_1$ include a hydrogen atom, halogen atoms, alkyl groups, aryl groups, heterocyclic groups, a cyano group, a hydroxy group, a nitro group, alkoxy groups, aryloxy groups, silyloxy groups, heterocyclic oxy groups, acyloxy groups, carbamoyloxy groups, alkoxycarbonyloxy groups, aryloxycarbonyloxy groups, an amino group, acylamino groups, ureido groups, alkoxycarbonylamino groups, aryloxycarbonylamino groups, sulfamoylamino groups, alkylsulfonylamino groups, arylsulfonylamino groups, alkylthio groups, arylthio groups, heterocyclic thio groups, a sulfamoyl group, alkylsulfinyl groups, arylsulfinyl groups, alkylsulfonyl groups, arylsulfonyl groups, acyl groups, aryloxycarbonyl groups, alkoxycarbonyl groups, a carbamoyl group, and imido groups. Of these, alkyl groups, aryl groups, heterocyclic groups, and alkoxycarbonyl groups are more preferred as $R_1$. As the alkyl group, a methyl group, an ethyl group, an isopropyl group, and a t-butyl group are more preferred, while as the aryl group, a phenyl group and a naphthyl group are more preferred.

In the formula (1), the monocyclic or bicyclic, aromatic heterocyclic residue of A preferably has, in the ring thereof, at least one hetero atom selected from an oxygen atom, a sulfur atom, and a nitrogen atom. The monocyclic aromatic heterocyclic residue is preferably a 5-membered ring group. The bicyclic aromatic heterocyclic residue is preferably a fused group of a 5- or 6-membered ring and a 5- or 6-membered ring. The aromatic heterocyclic residue has preferably from 2 to 20 carbon atoms, more preferably from 2 to 10 carbon atoms.

Preferred examples of the aromatic heterocyclic residue of A include residues of a pyrrole ring, a thiophene ring, a furan ring, an oxazole ring, a pyrazole ring, an imidazole ring, an isoxazole ring, a thiadiazole ring, a thiazole ring, an isothiazole ring, a triazole ring, an oxadiazole ring, a benzoxazole ring, a benzisoxazole ring, a benzothiazole ring, a benzisothiazole ring, and a benzimidazole ring. Of these, the residues of a benzoxazole ring, a pyrazole ring, a thiazole ring, an isothiazole ring, a thiadiazole ring, a benzothiazole ring, and a benzisothiazole ring are preferred, of which the residues of a benzisothiazole ring, a pyrazole ring, an isothiazole ring, and a thiadiazole ring are especially preferred.

As a substituent which the aromatic heterocyclic group may have, examples of the substituents described above as $R_1$ can be used. When these substituents are adjacent to each other, they may be coupled to form a saturated or unsaturated, 5- or 6-membered ring structure. The ring structure thus formed may be a heterocyclic ring or a carbon ring, or may be a saturated ring or an unsaturated ring. The total number of the carbon atoms and hetero atoms of the cyclic structure thus formed is preferably from 3 to 6, more preferably from 5 or 6.

The substituents which the aromatic heterocyclic group may have are more preferably halogen atoms, alkyl groups, aryl groups, heterocyclic groups, a cyano group, a hydroxy group, a nitro group, alkoxy groups, aryloxy groups, amino groups (including anilino group), acylamino groups, ureido groups, alkoxycarbonylamino groups, alkylsulfonylamino groups, arylsulfonylamino groups, alkylthio groups, arylthio groups, heterocyclic thio groups, a sulfamoyl group, alkylsulfonyl groups, arylsulfonyl groups, acyl groups, alkoxycarbonyl groups, and a carbamoyl group.

The substituent which the aromatic heterocyclic group may have has preferably from 1 to 10, more preferably from 1 to 8 carbon atoms.

When these substituents have an asymmetric carbon, either one of enantiomers or a mixture of both of them mixed at a desired ratio can be used freely for the dissociative azo dye to be used in the present invention. When these substituents have two or more asymmetric carbons, there exists a plurality of stereoisomers for one structure. For the dissociative azo dye to be used in the present invention, one or more of the stereoisomers may be used as a mixture.

In the formula (1), $R_1$ and A each does not contain a carboxy group, a sulfo group, and a quaternary ammonium group. These carboxy groups and sulfo groups include, in addition to these acid type groups, neutral type groups such as —COONa and —SO₃Na. This means that the dye to be used in the present invention contains none of the acid-type and neutral type carboxy groups and sulfo groups, and a quaternary ammonium group.

Examples of the group represented by A in the formula (1) include aromatic heterocyclic groups represented by the following formulas (A-1) to (A-33). In the following formulas, symbol * means a position at which A is linked to the azo group in the formula (1), n stands for an integer from 0 to 4, and $R_{11}$ to $R_{68}$ each represents a substituent. Examples of the substituent include those described above as examples of $R_1$. Two adjacent substituents may be coupled to form a saturated or unsaturated 5- or 6-membered ring structure.

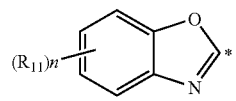
(A-1)

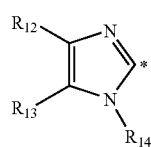
(A-2)

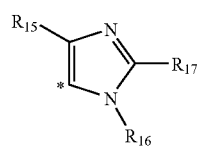
(A-3)

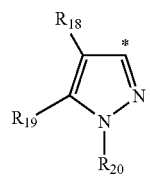
(A-4)

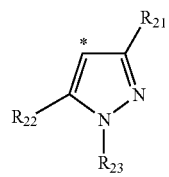
(A-5)

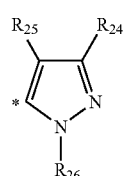
(A-6)

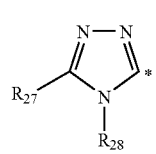
(A-7)

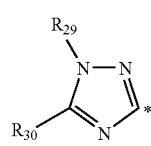
(A-8)

-continued

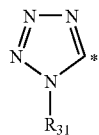
(A-9)

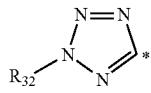
(A-10)

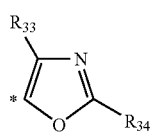
(A-11)

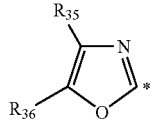
(A-12)

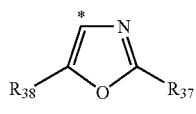
(A-13)

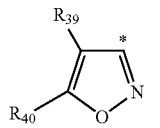
(A-14)

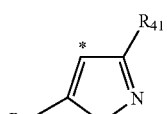
(A-15)

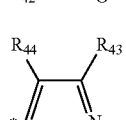
(A-16)

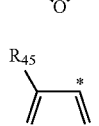
(A-17)

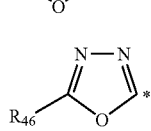
(A-18)

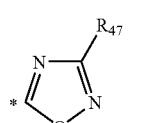
(A-19)

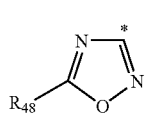
(A-20)

-continued
(A-21) 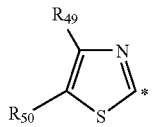
(A-22) 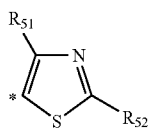
(A-23) 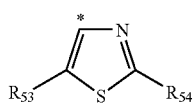
(A-24) 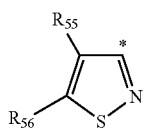
(A-25) 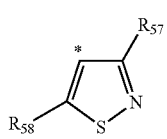
(A-26) 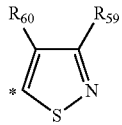
(A-27) 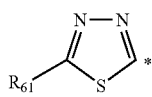
(A-28) 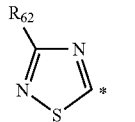
(A-29) 
(A-30) 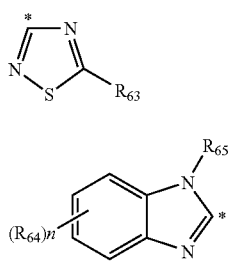
(A-31) 
(A-32) 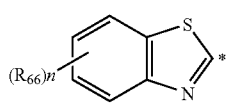
-continued
(A-33) 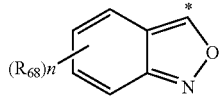
As the group represented by A, the group represented by the formula (A-1), (A-2), (A-6), (A-21), (A-26), (A-27), (A-28), (A-31) or (A-32) is preferred, with the group represented by the formula (A-6), (A-26), (A-27), (A-28) or (A-32) being more preferred.
The following are specific examples of the dissociative azo dye represented by the formula (1) but they are not limited to the following examples.
D1-1 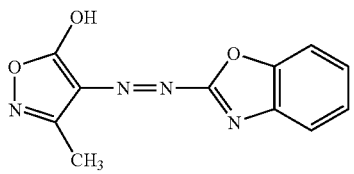
D1-2 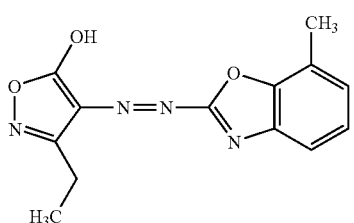
D1-3 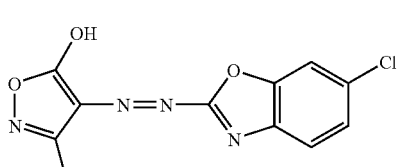
D1-4 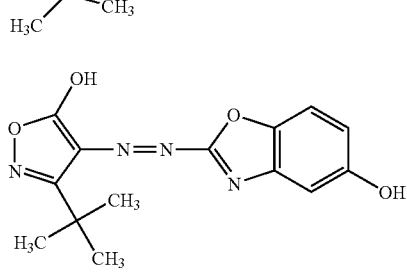
D1-5 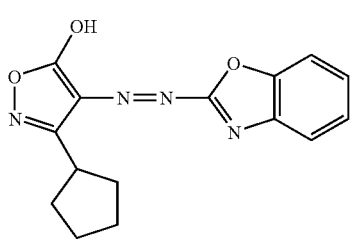

-continued
D1-6 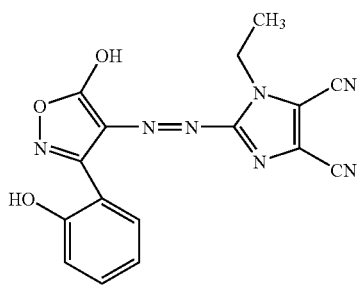
D1-7 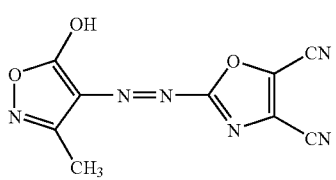
D1-8 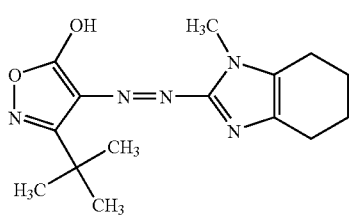
D1-9 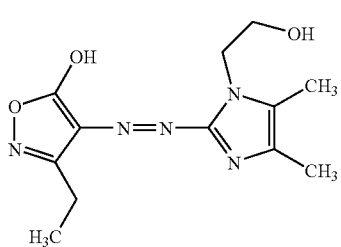
D1-10 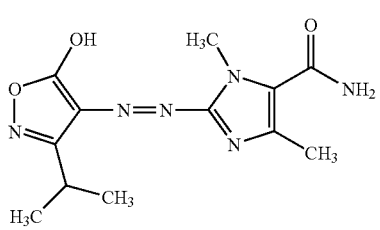
D1-11 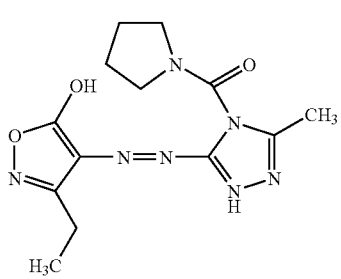
-continued
D1-12 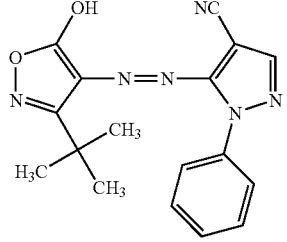
D1-13 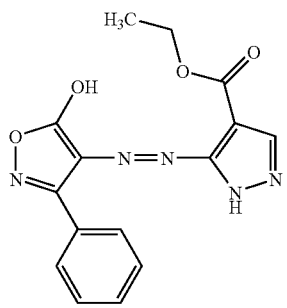
D1-14 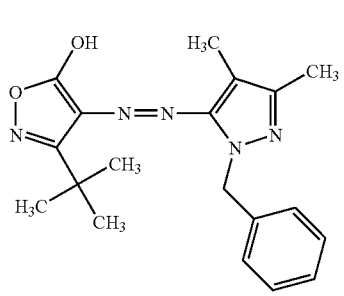
D1-15
D1-16
D1-17

-continued
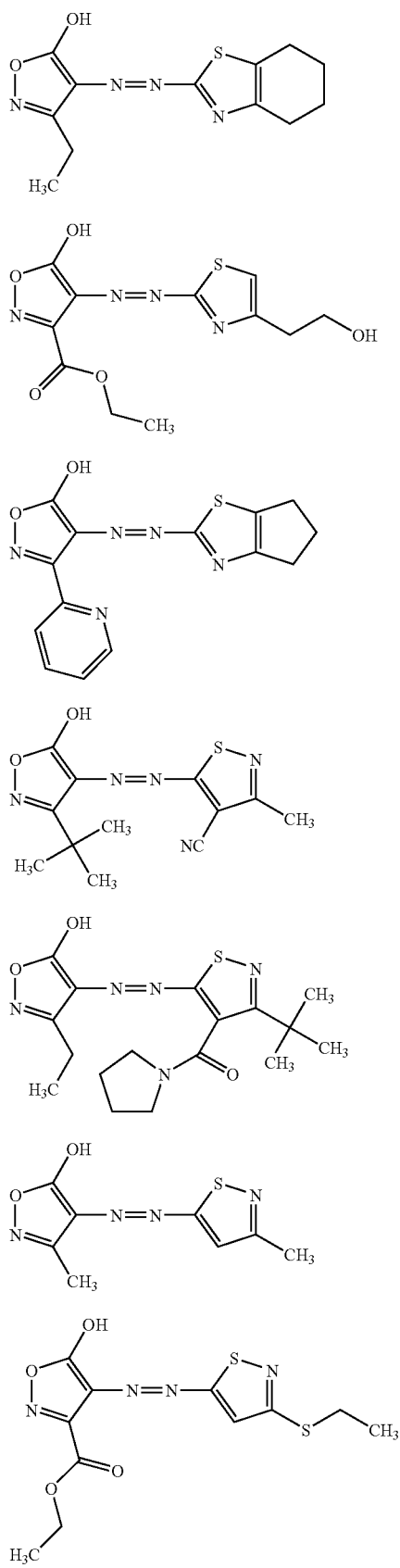
D1-18
D1-19
D1-20
D1-21
D1-22
D1-23
D1-24
-continued
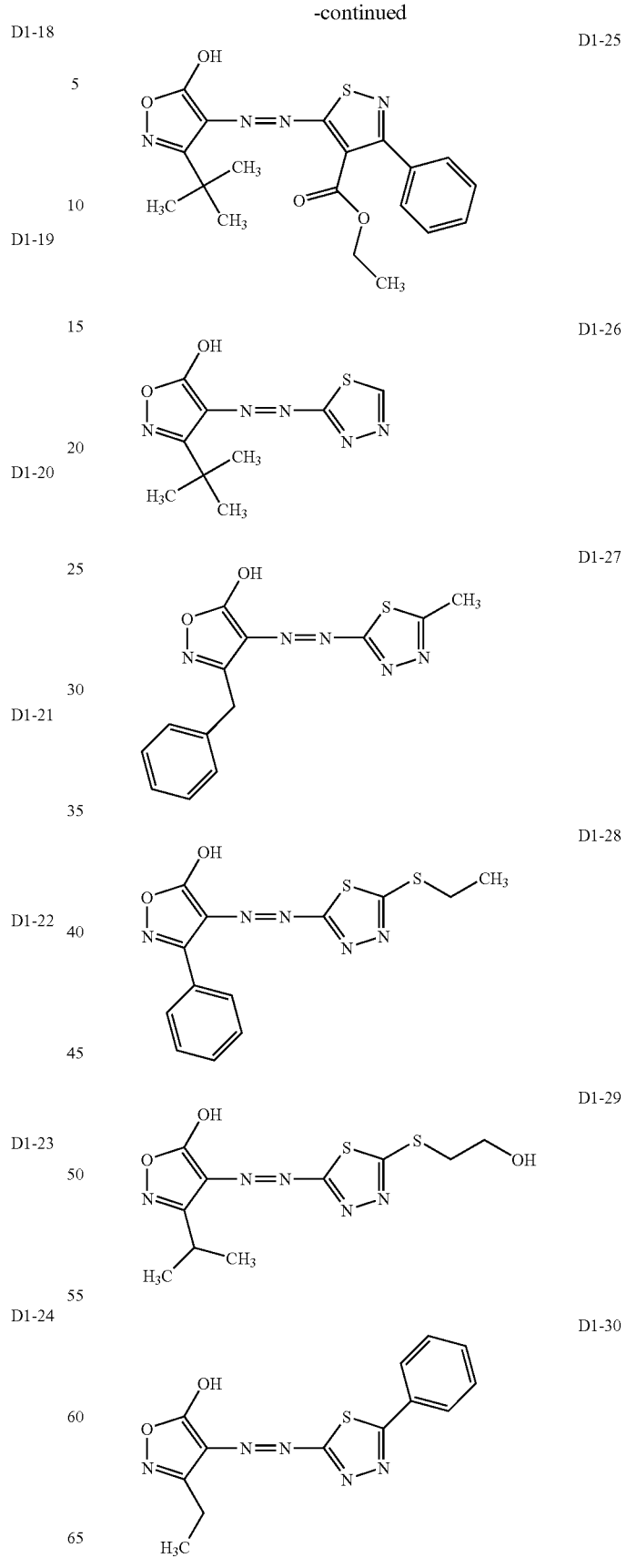
D1-25
D1-26
D1-27
D1-28
D1-29
D1-30

-continued
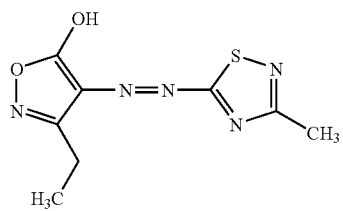
D1-31
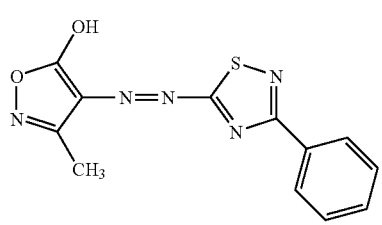
D1-32
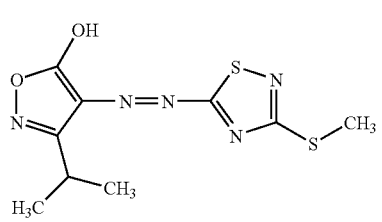
D1-33
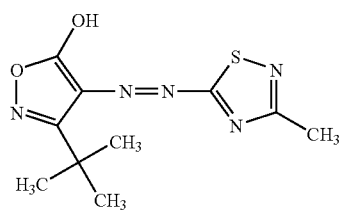
D1-34
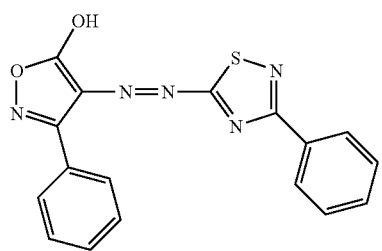
D1-35
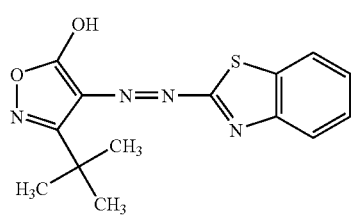
D1-36
-continued
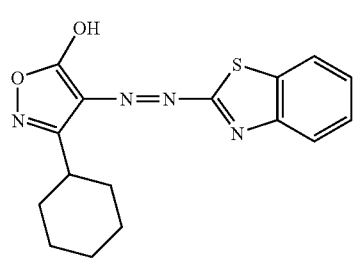
D1-37
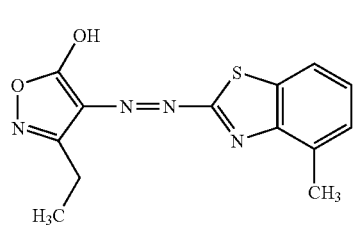
D1-38
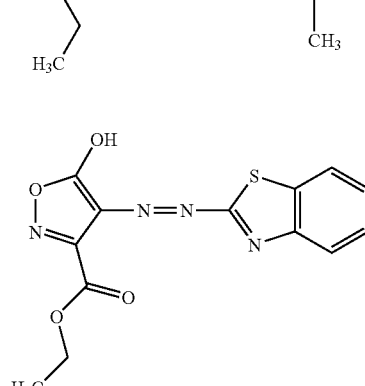
D1-39
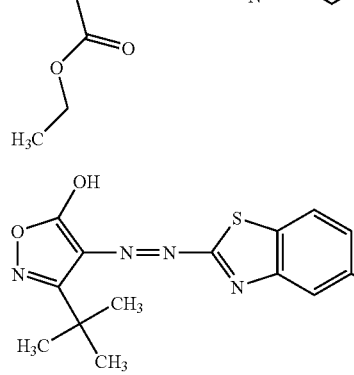
D1-40
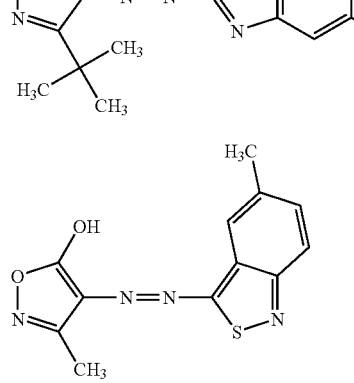
D1-41
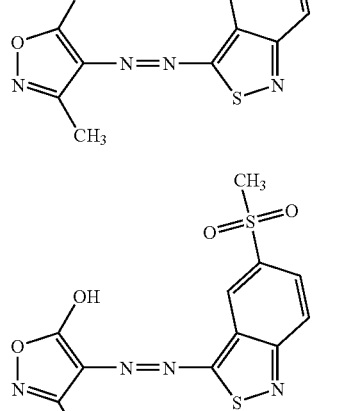
D1-42

-continued

D1-43 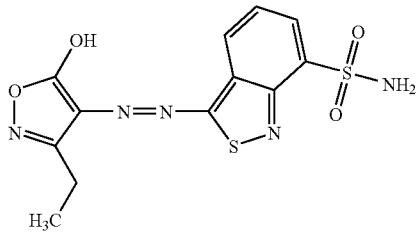

D1-44 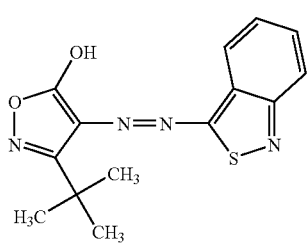

D1-45 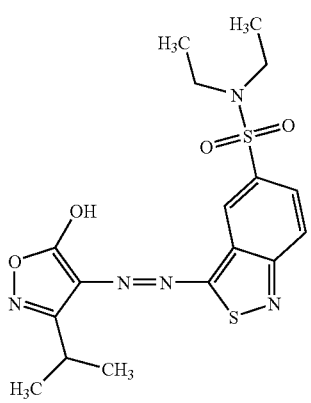

D1-46 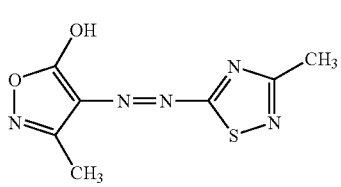

-continued

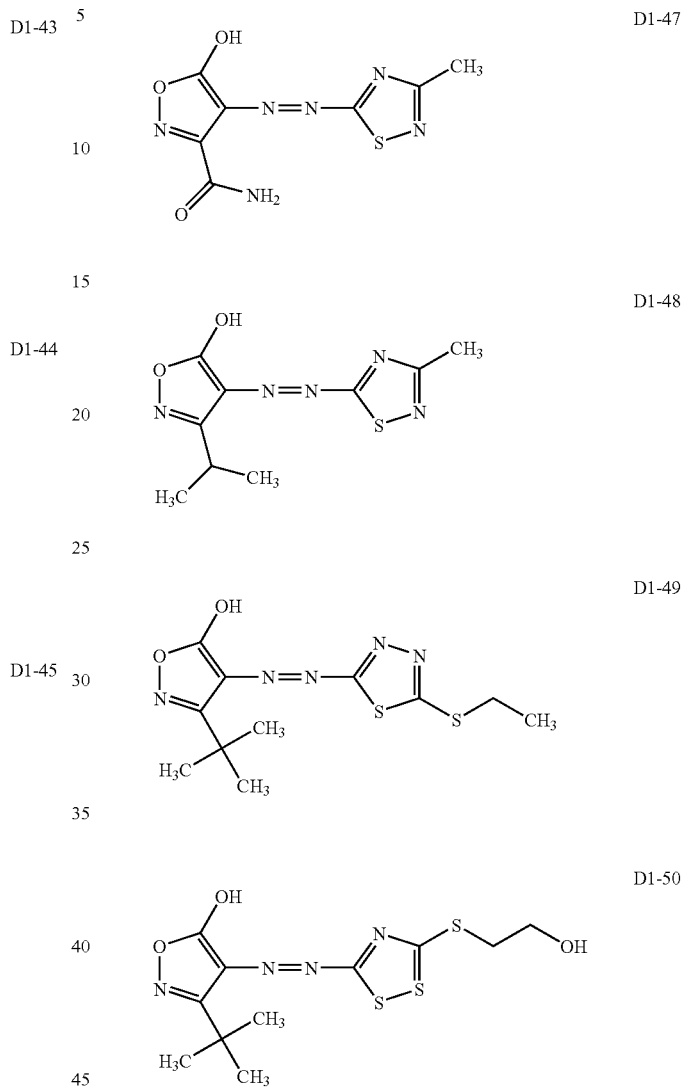

D1-47

D1-48

D1-49

D1-50

Dissociative Azo Dyes Represented by the Formula (2)

The dissociative azo dye represented by the formula (2) imparts a desired hue to hair in the following manner. The carbonyl group of the thiadiazinane dione ring becomes a hydroxy group in the hair dye system based on the keto-enol tautomerism represented by the following reaction scheme and the dissociation of a proton at pH 2 or greater causes a change in hue.

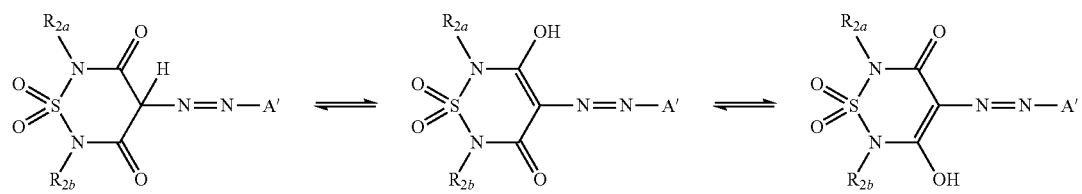

Examples of when $R_{2a}$ or $R_{2b}$ in the formula (2) is not a hydrogen atom, $R_{2a}$ or $R_{2b}$ includes:

alkyl groups (linear, branched, or cyclic alkyl groups having from 1 to 15, preferably from 1 to 6 carbon atoms, such as a methyl group, an ethyl group, an n-propyl group, an isopropyl group, an s-butyl group, a t-butyl group, an n-octyl group, a 2-ethylhexyl group, a cyclopentyl group, and a cyclohexyl group), alkenyl groups (linear, branched, or cyclic alkenyl groups having from 2 to 10, preferably from 2 to 6 carbon atoms, such as a vinyl group, an allyl group, a prenyl group, and a cyclopenten-1-yl group), alkynyl groups (alkynyl groups having from 2 to 10, preferably from 2 to 6 carbon atoms, such as an ethynyl group and a propargyl group), aryl groups (aryl groups having from 6 to 16, preferably from 6 to 10 carbon atoms, such as a phenyl group, an o-tolyl group, a p-tolyl group, and a naphthyl group), heterocyclic groups (monovalent groups having from 1 to 12, preferably from 2 to 6 carbon atoms, which are available by removing a hydrogen atom from 5- to 10-membered, preferably from 5- or 6-membered aromatic or non-aromatic heterocyclic compounds, such as a 1-pyrazolyl group, a 1-imidazolyl group, a 2-furyl group, a 2-thienyl group, a 4-pyrimidinyl group, a 2-pyridyl group, a 2-benzothiazolyl group, a 2-tetrahydrofuryl group, and a 2-morpholyl group)

a carbamoyl group, a sulfamoyl group, acyl groups (a formyl group, alkylcarbonyl groups having from 2 to 10, preferably from 2 to 6 carbon atoms, arylcarbonyl groups having from 7 to 12, preferably from 7 to 9 carbon atoms, heterocyclic carbonyl groups having from 2 to 12, preferably from 2 to 6 carbon atoms, such as a formyl group, an acetyl group, a propionyl group, a pivaloyl group, a benzoyl group, and a 2-pyridylcarbonyl group), alkoxycarbonyl groups (alkoxycarbonyl groups having from 2 to 10, preferably from 2 to 6 carbon atoms, such as a methoxycarbonyl group, an ethoxycarbonyl group, a t-butoxycarbonyl group, and an isobutyloxycarbonyl group), aryloxycarbonyl groups (aryloxycarbonyl groups having from 7 to 12, preferably from 7 to 9 carbon atoms, such as a phenoxycarbonyl group and a naphthoxycarbonyl group), heterocyclic oxycarbonyl groups (heterocyclic oxycarbonyl groups having from 1 to 12, preferably from 2 to 6 carbon atoms, such as a 1-pyrazolyloxycarbonyl group, a 1-imidazolyloxycarbonyl group, a 2-furyloxycarbonyl group, a 2-thienyloxycarbonyl group, a 2-tetrahydrofuryloxycarbonyl group, and a 2-morpholyloxycarbonyl group), imido groups (imido groups having from 2 to 10, preferably from 4 to 8 carbon atoms, such as an N-succinimido group and an N-phthalimido group), alkylsulfinyl groups (alkylsulfinyl groups having from 1 to 10, preferably from 1 to 6 carbon atoms, such as a methylsulfinyl group and an ethylsulfinyl group), arylsulfinyl groups (arylsulfinyl groups having from 6 to 12, preferably from 6 to 8 carbon atoms, such as a phenylsulfinyl group), alkylsulfonyl groups (alkylsulfonyl groups having from 1 to 10, preferably from 1 to 6 carbon atoms, such as a methylsulfonyl group, an ethylsulfonyl group, and a cyclohexylsulfonyl group), arylsulfonyl groups (arylsulfonyl groups having from 6 to 12, preferably from 6 to 8 carbon atoms, such as a phenylsulfonyl group), and heterocyclic sulfonyl groups (heterocyclic sulfonyl groups having from 1 to 12, preferably from 2 to 6 carbon atoms, such as a 2-tetrahydropyranylsulfonyl group).

Examples also include these substituents having one or more substituents. In this case, preferred examples of the one or more substituents include the groups described above as examples of the substituents. When the substituents have two or more substituents, the two or more substituents may be the same or different.

The following are examples of the substituent having a further substituent. Examples of the alkyl or aryl group having a substituent include:

aralkyl groups (aralkyl groups having from 7 to 18, preferably from 7 to 12 carbon atoms, such as a benzyl group and a phenethyl group), haloalkyl groups (linear, branched, or cyclic haloalkyl groups having from 1 to 15, preferably from 1 to 6 carbon atoms, such as a chloromethyl group, a 2-chloroethyl group, a 2-bromopropyl group, and a 3-bromopropyl group), haloaryl groups (haloaryl groups having from 6 to 12, preferably from 6 to 8 carbon atoms, such as a p-chlorophenyl group, a 2,4-dichlorophenyl group, and a 3-fluorophenyl group), and hydroxyalkyl groups (linear, branched, or cyclic alkyl groups having from 1 to 15, preferably from 1 to 6 carbon atoms, such as a hydroxymethyl group, a 2-hydroxyethyl group, a 2-hydroxypropyl group, and a 3-hydroxypropyl group).

Examples of the carbamoyl group having a substituent include:

alkylcarbamoyl groups (carbamoyl groups having from 1 to 12, preferably from 1 to 8 carbon atoms, such as a methylcarbamoyl group, a dimethylcarbamoyl group, a diethylcarbamoyl group, and a 1-pyrrolidylcarbonyl group), and sulfamoylcarbamoyl groups (sulfamoylcarbamoyl groups having from 1 to 12, preferably from 1 to 8 carbon atoms, such as an N-(sulfamoyl)carbamoyl group, and an N—(N',N'-dimethylsulfamoyl)carbamoyl group).

Examples of the sulfamoyl group having a substituent include:

alkylsulfamoyl groups (alkylsulfamoyl groups having from 1 to 12, preferably from 1 to 6 carbon atoms, such as an ethylsulfamoyl group, a dimethylsulfamoyl group, a dibutylsulfamoyl group, an ethylmethylsulfamoyl group, a diethylsulfamoyl group, and an N-cyclohexyl-N-methylsulfamoyl group), arylsulfamoyl groups (arylsulfamoyl groups having from 6 to 12, preferably from 6 to 8 carbon atoms, such as a phenylsulfamoyl group), and carbamoylsulfamoyl groups (carbamoylsulfamoyl groups having from 1 to 12, preferably from 1 to 6 carbon atoms, such as an N-(carbamoyl)sulfamoyl group).

Examples of the substituent having a substituent, the latter substituent having a substituent further, include:

alkoxyalkyl groups (linear, branched, or cyclic alkoxyalkyl groups having from 1 to 32, preferably from 1 to 12 carbon atoms, such as a methoxymethyl group, a methoxyethyl group, an ethoxyethyl group, and a cyclohexyloxypropyl group), alkoxyaryl groups (alkoxyaryl groups having from 7 to 18, preferably from 7 to 12 carbon atoms, such as a p-methoxyphenyl group and a 2,4-dimethoxyphenyl group), alkoxycarbonylalkyl groups (alkoxycarbonylalkyl groups having from 2 to 15, preferably from 2 to 6 carbon atoms, such as a methoxycarbonylethyl group and a 3-ethoxycarbonylpropyl group), alkylaminoalkyl groups (alkylamino alkyl groups having from 2 to 15, preferably from 2 to 6 carbon atoms, such as an N-methylaminomethyl group and a dimethylaminoethyl group), alkylthioalkyl groups (alkylthioalkyl groups having from 2 to 15, preferably from 2 to 6 carbon atoms, such as a methylthiomethyl group, a methylthioethyl group, and an ethylthioethyl group), haloalkoxyaryl groups (haloalkoxyaryl groups having from 7 to 18, preferably from 7 to 12 carbon atoms, such as a 2-chloro-4-methoxyphenyl group and a 2,5-dichloro-4-methoxyphenyl group), alkoxycarbonyloxy groups (alkoxycarbonyloxy groups having from 2 to 15, preferably from 2 to 6 carbon atoms, such as a methoxycarbonyloxy group and an ethoxycarbonyloxy group), aryloxycarbonyloxy groups (aryloxycarbonyloxy groups having from 7 to 18, preferably from 7 to 12 carbon atoms, such as a phenoxycarbonyloxy group), alkoxycarbonylamino groups (alkoxycarbonylamino groups having from 2 to 10, preferably from 2 to 6 carbon atoms, such as a methoxycarbonylamino group, an ethoxycarbonylamino group, a t-butoxycarbonylamino group, and an isobutyloxycarbonylamino group), and hydroxyalkylthio groups (hydroxyalkylthio groups having from 1 to 15, preferably from 1 to 6 carbon atoms, such as a hydroxyethylthio group and a 2-hydroxypropylthio group).

$R_{2a}$ and $R_{2b}$ are each preferably a hydrogen atom, an alkyl group, an aryl group, a heterocyclic group, an alkylsulfonyl group, an arylsulfonyl group, an acyl group, an aryloxycarbonyl group, an alkoxycarbonyl group, or a carbamoyl group, more preferably a hydrogen atom, an alkyl group, an aryl group, or an acyl group. The alkyl group is more preferably a methyl group, an ethyl group, an isopropyl group, a t-butyl group, or a cyclohexyl group; the aryl group is more preferably a phenyl group, a tolyl group, or a naphthyl group; and the acyl group is more preferably an acetyl group or a propionyl group.

In the formula (2), the monocyclic or bicyclic aromatic heterocyclic residue of A' preferably has, in the ring thereof, at least one hetero atom selected from an oxygen atom, a sulfur atom, and a nitrogen atom. The monocyclic aromatic heterocyclic residue is preferably a 5-membered ring group. The bicyclic aromatic heterocyclic residue is preferably a fused group of a 5- or 6-membered ring and a 5- or 6-membered ring. The aromatic heterocyclic residue has preferably from 2 to 20 carbon atoms, more preferably from 2 to 10 carbon atoms.

Preferred examples of the aromatic heterocyclic residue of A' include residues of a pyrrole ring, a thiophene ring, a furan ring, an oxazole ring, a pyrazole ring, an imidazole ring, an isoxazole ring, a thiadiazole ring, an isothiazole ring, a triazole ring, an oxadiazole ring, a benzoxazole ring, a benzisoxazole ring, a benzothiazole ring, a benzisothiazole ring, and a benzimidazole ring. Of these, residues of a benzoxazole ring, a pyrazole ring, a thiazole ring, an isothiazole ring, a thiadiazole ring, a benzothiazole ring, and a benzisothiazole ring are preferred, of which the residues of a benzisothiazole ring, an isothiazole ring, and a thiadiazole ring are more preferred.

Examples of the substituent which the aromatic heterocyclic group may have include those described above as $R_{2a}$ and $R_{2b}$ and halogen atoms (such as a fluorine atom, a chlorine atom, and a bromine atom),
  a hydroxy group,
  an amino group,
  a mercapto group,
  a nitro group,
  a cyano group, and
  a phosphoryl group. The aromatic heterocyclic group may have two or more substituents and these two or more substituents may be the same or different. These two or more substituents may have one or more substituents further. In this case, examples of the one or more substituents are preferably those described above as substituents. When the number of the substituents is two or more, they may be the same or different. When these substituents are adjacent to each other, they may be coupled together to form a saturated or unsaturated 5- or 6-membered ring structure. The ring structure thus formed may be either a heterocyclic ring or a carbon ring, or a saturated ring or an unsaturated ring. The total number of carbon atoms and hetero atoms of the ring structure thus formed is preferably from 3 to 6, more preferably from 5 to 6.

The following are examples of the substituent having a substituent further. Examples of a hydroxy group having a substituent include:

alkoxy groups (linear, branched, or cyclic alkoxy groups having from 1 to 10, preferably from 1 to 6 carbon atoms, such as a methoxy group, an ethoxy group, an isopropoxy group, a t-butoxy group, and a cyclopentyloxy group), alkenyloxy groups (linear, branched, or cyclic alkenyloxy groups having from 2 to 10, preferably from 2 to 6 carbon atoms, such as a 2-buten-1-yloxy group), aryloxy groups (aryloxy groups having from 6 to 12, preferably from 6 to 10 carbon atoms, such as a phenoxy group, a 2-methylphenoxy group, and a 4-t-butylphenoxy group), silyloxy groups (silyloxy groups having from 3 to 10, preferably from 3 to 6 carbon atoms such as a trimethylsilyloxy group and a t-butyldimethylsilyloxy group), heterocyclic oxy groups (heterocyclic oxy groups having from 1 to 12, preferably from 2 to 6 carbon atoms, such as a 1-phenyltetrazol-5-oxy group and a 2-tetrahydropyranyloxy group), alkylsulfonyloxy groups (linear, branched, or cyclic alkylsulfonyloxy groups having from 1 to 10, preferably from 1 to 6 carbon atoms, such as a methanesulfonyloxy group and an ethanesulfonyloxy group), arylsulfonyloxy groups (arylsulfonyloxy groups having from 6 to 12, preferably from 6 to 10 carbon atoms, such as a phenylsulfonyloxy group), heterocyclic sulfonyloxy groups (heterocyclic sulfonyloxy groups having from 1 to 12, preferably from 2 to 6 carbon atoms, such as a 2-pyridylsulfonyloxy group), acyloxy groups (acyloxy groups having from 1 to 12, preferably from 1 to 8 carbon atoms, such as a formyloxy group, an acetyloxy group, a pivaloyloxy group and a benzoyloxy group), carbamoyloxy groups (carbamoyloxy groups having from 1 to 10, preferably from 1 to 6 carbon atoms, such as an N,N-dimethylcarbamoyloxy group, an N,N-diethylcarbamoyloxy group, and a morpholinocarbonyloxy group), alkoxycarbonyloxy groups (alkoxycarbonyloxy groups having from 2 to 10, preferably from 2 to 8 carbon atoms, such as a methoxycarbonyloxy group, an ethoxycarbonyloxy group, a t-butoxycarbonyloxy group, and an n-octyloxycarbonyloxy group), aryloxycarbonyloxy groups (aryloxycarbonyloxy groups having from 7 to 12, preferably from 7 to 10 carbon atoms, such as a phenoxycarbonyloxy group and a p-methoxyphenoxycarbonyloxy group), and dialkylphosphinyloxy groups (phosphinyloxy groups having from 2 to 12, preferably from 2 to 6 carbon atoms, such as a dimethylphosphinyloxy group and a dibutylphosphinyloxy group).

Examples of the amino group having a substituent include:
  alkylamino groups (alkylamino groups having from 1 to 20, preferably from 1 to 12 carbon atoms, such as a methylamino group, a dimethylamino group, a cyclohexylmethylamino group, and a 1-pyrrolidyl group), arylamino groups (arylamino groups having from 6 to 16, preferably from 6 to 12 carbon atoms, such as an anilino group, an N-methylanilino group, and a diphenylamino group), heterocyclic amino groups (heterocyclic amino groups having from 1 to 12, preferably from 2 to 6 carbon atoms, such as a 2-pyridylamino group, a pyrazol-4-ylamino group, a benzimidazol-2-ylamino group, a benzothiazol-2-ylamino group, a benzoxazol-2-ylamino group, a 2-oxazolylamino group, a 1,2,4-triazol-3-ylamino group, a 1,2,4-thiadiazol-2-ylamino group, a 1,3,4-thiadiazol-2-ylamino group, a 1,2,4-oxadiazol-2-ylamino group, and a 1,3,4-oxadiazol-2-ylamino group), acylamino groups (alkylcarbonylamino groups having from 1 to 10, preferably from 1 to 6 carbon atoms, arylcarbonylamino groups having from 6 to 18, preferably from 6 to 12 carbon atoms, and heterocyclic carbonylamino groups having from 2 to 12, preferably from 2 to 6 carbon atoms, such as a formylamino group, an acetylamino group, an ethylcarbonylamino group, a pivaloylamino group, a benzoylamino group, and a 4-pyridylcarbonylamino group), ureido groups (aminocarbonylamino groups having from 1 to 12, preferably from 1 to 8 carbon atoms, such as a carbamoylamino group, an N,N-dimethylaminocarbonylamino group, an N,N-diethylaminocarbonylamino group, and a morpholin-4-ylcarbonylamino group), alkoxycarbonylamino groups (alkoxycarbonylamino groups having from 2 to 10, preferably from 2 to 6 carbon atoms, such as a methoxycarbonylamino group, an ethoxycarbonylamino group, and a t-butoxycarbonylamino group), aryloxycarbonylamino groups (aryloxycarbonylamino groups having from 7 to 12, preferably from 7 to 9 carbon atoms, such as a phenoxycarbonylamino group), heterocyclic oxycarbonylamino groups (heterocyclic oxycarbonylamino groups having from 1 to 12, preferably from 2 to 6 carbon atoms, such as a 2-pyridyloxycarbonylamino group), sulfamoylamino groups (sulfamoylamino groups having from 0 to 10, preferably from 0 to 6 carbon atoms, such as a sulfamoylamino group and an N,N-dimethylaminosulfonylamino group), alkylsulfonylamino groups (alkylsulfonylamino groups having from 1 to 10, preferably from 1 to 6 carbon atoms, such as a methylsulfonylamino group, an ethylsulfonylamino group, and an n-butylsulfonylamino group), arylsulfonylamino groups (arylsulfonylamino groups having from 6 to 12, preferably from 6 to 8 carbon atoms, such as a phenylsulfonylamino group), and phosphinylamino groups (phosphinylamino groups having from 2 to 12, preferably from 2 to 6 carbon atoms, such as a dimethoxyphosphinylamino group and a dimethylaminophosphinylamino group).

Examples of the mercapto group having a substituent include:

alkylthio groups (alkylthio groups having from 1 to 10, preferably from 1 to 6 carbon atoms, such as a methylthio group, an ethylthio group, and a butylthio group), arylthio groups (arylthio groups having from 6 to 12, preferably from 6 to 8 carbon atoms, such as a phenylthio group), and heterocyclic thio groups (heterocyclic thio groups having from 1 to 10, preferably from 1 to 6 carbon atoms, such as a 2-benzothiazolylthio group, and a 1-phenyltetrazol-5-ylthio group).

Examples of the phosphoryl group having a substituent include:

alkylphosphoryl groups (alkylphosphoryl groups having from 1 to 12, preferably from 1 to 6 carbon atoms, such as a methylphosphoryl group and an ethylphosphoryl group).

The substituent which the aromatic heterocyclic group may have is preferably a halogen atom, an alkyl group, an aryl group, a heterocyclic group, a cyano group, a hydroxy group, a nitro group, an alkoxy group, an aryloxy group, an amino group (including an anilino group), an acylamino group, a ureido group, an alkoxycarbonylamino group, an alkylsulfonylamino group, an arylsulfonylamino group, an alkylthio group, an arylthio group, a heterocyclic thio group, a sulfamoyl group, an alkylsulfonyl group, an arylsulfonyl group, an acyl group, an alkoxycarbonyl group, or a carbamoyl group.

The substituent which the aromatic heterocyclic group may have has preferably from 1 to 10, more preferably from 1 to 8 carbon atoms.

The A', $R_{2a}$ and $R_{2b}$ in the formula (2) each contains none of a carboxy group, a sulfo group, and a quaternary ammonium group. These carboxy groups and sulfo groups include, in addition to these acid type groups, neutral type groups such as —COONa and —SO$_3$Na. This means that the dye of the present invention contains none of the acid-type and neutral type carboxy groups and sulfo groups, and a quaternary ammonium group.

In the formula (2), specific examples of the group represented by A' and preferred examples thereof are similar to those described as A in the formula (1).

The following are specific examples of the dissociative azo dye represented by the formula (2), but they are not limited to the following examples.

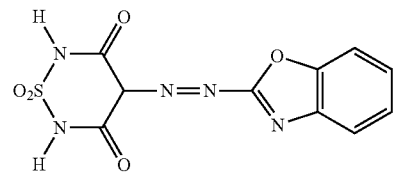

D2-1

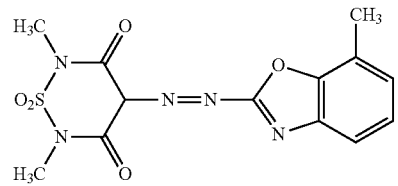

D2-2

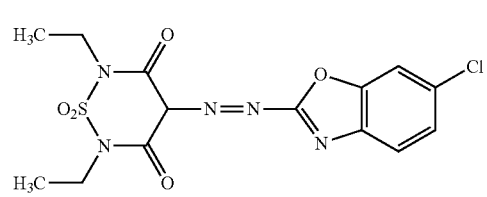

D2-3

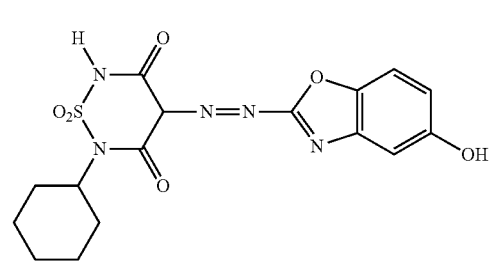

D2-4

-continued
D2-5
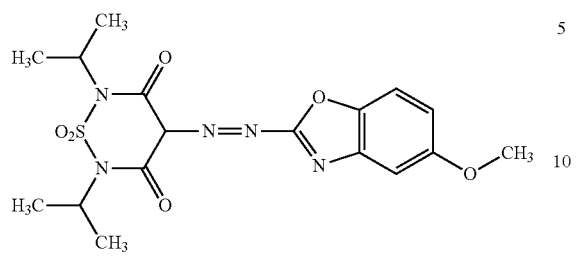
D2-6
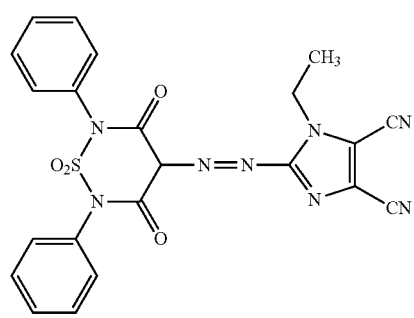
D2-7
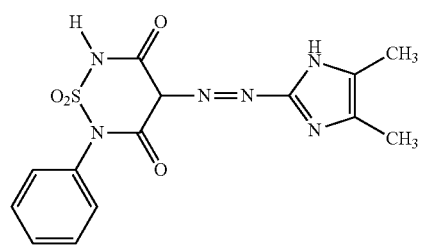
D2-8
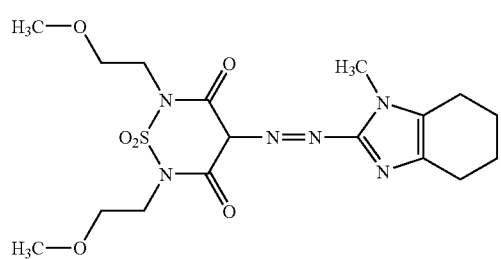
D2-9
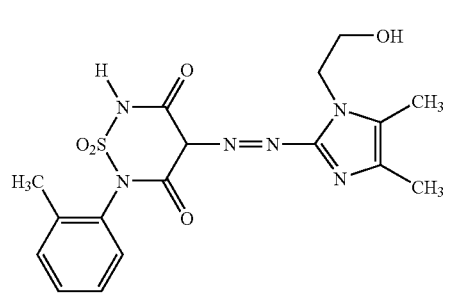
-continued
D2-10
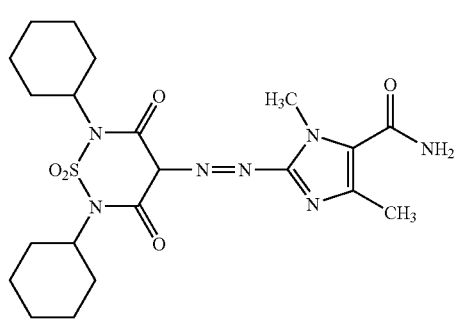
D2-11
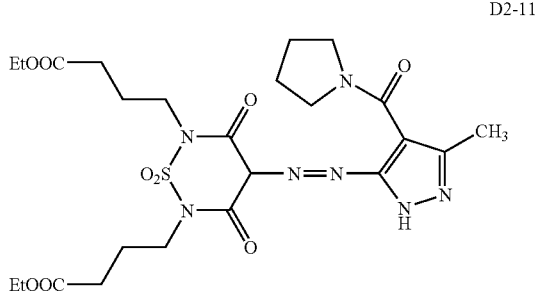
D2-12
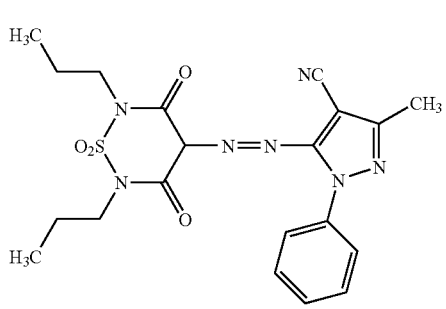
D2-13
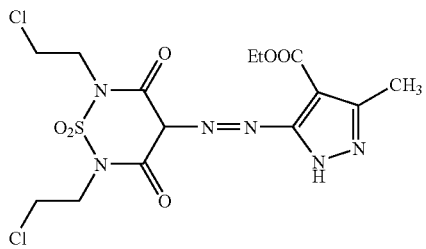
D2-14
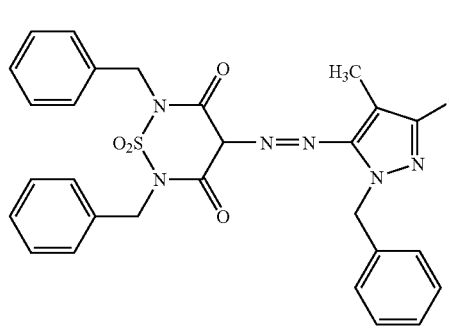

-continued
D2-15
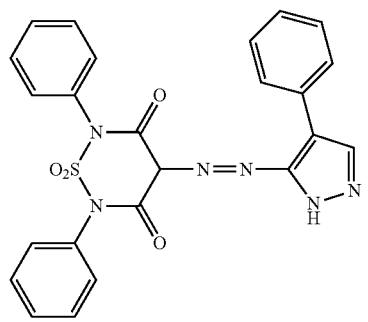
D2-16
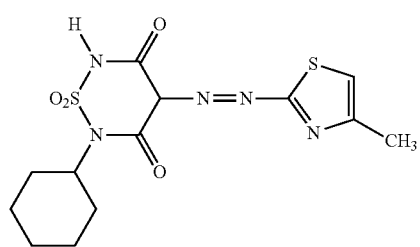
D2-17
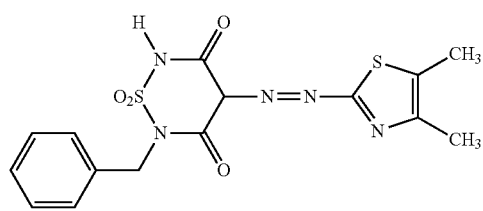
D2-18
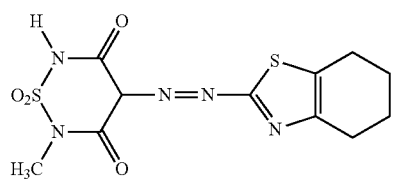
D2-19
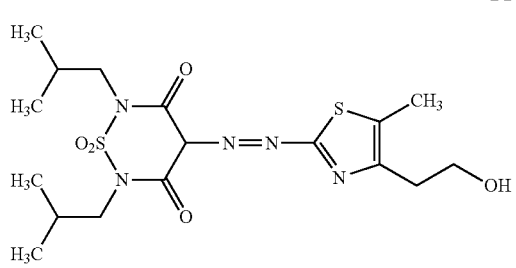
D2-20
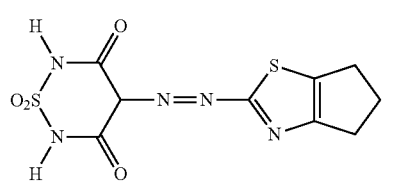
D2-21
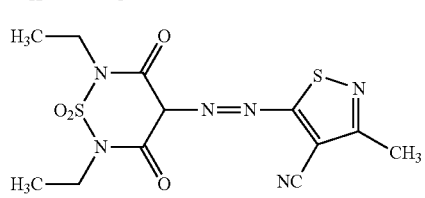
-continued
D2-22
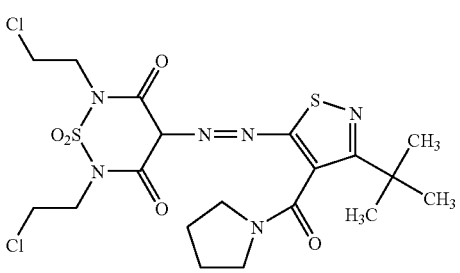
D2-23
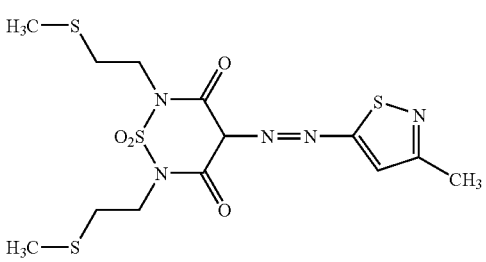
D2-24
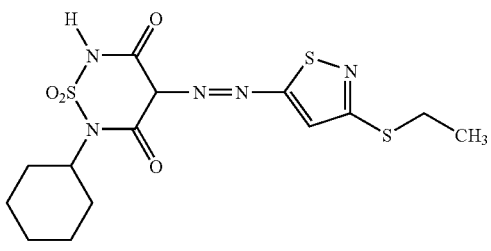
D2-25
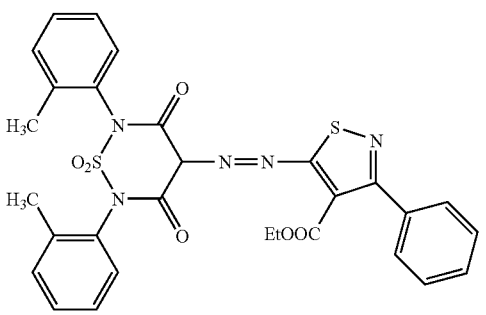
D2-26
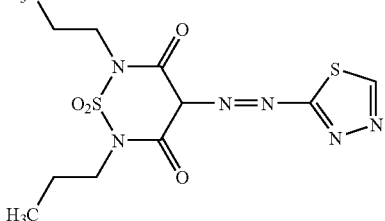
D2-27
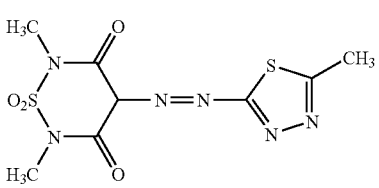

D2-28
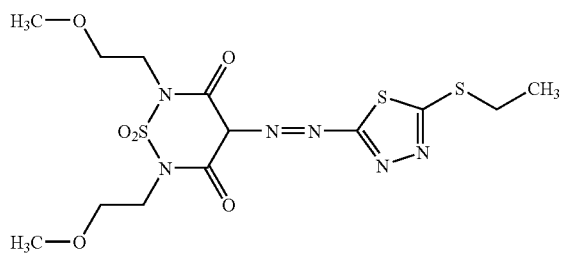
D2-29
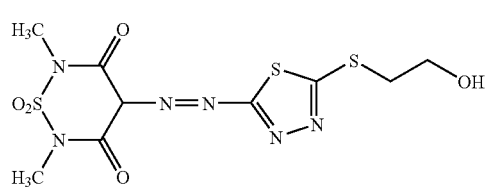
D2-30
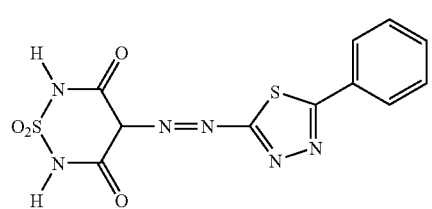
D2-31
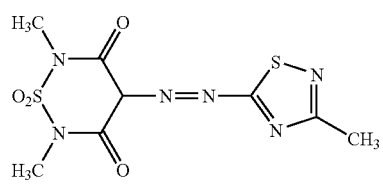
D2-32
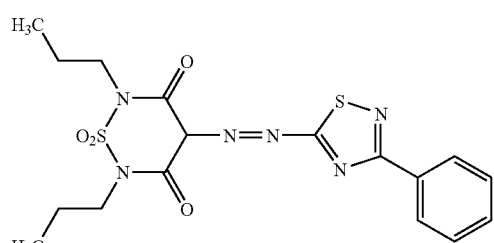
D2-33
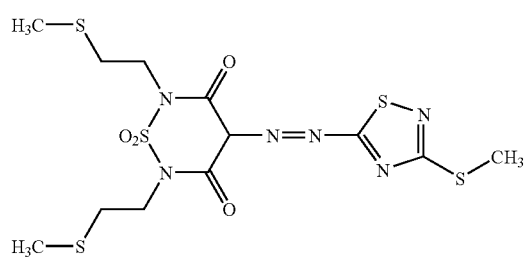
D2-34
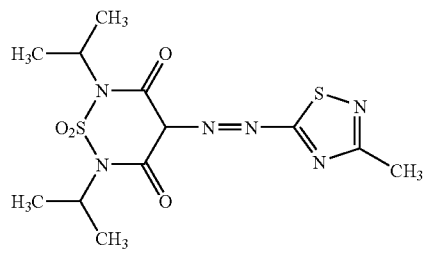
D2-35
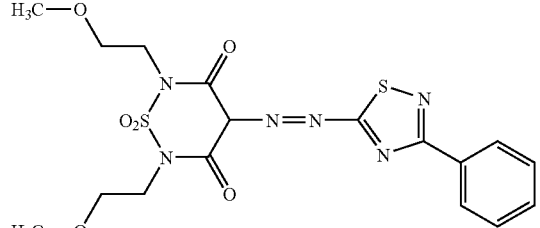
D2-36
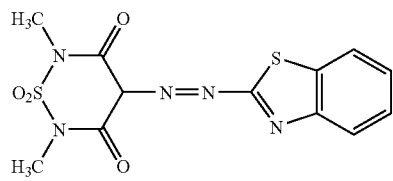
D2-37
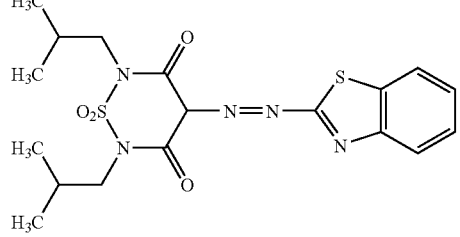
D2-38
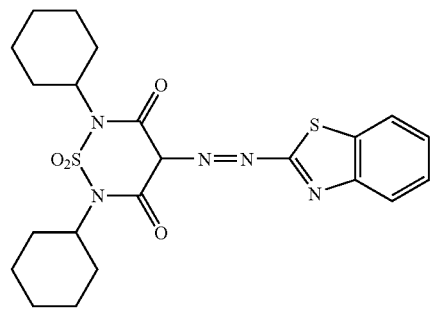

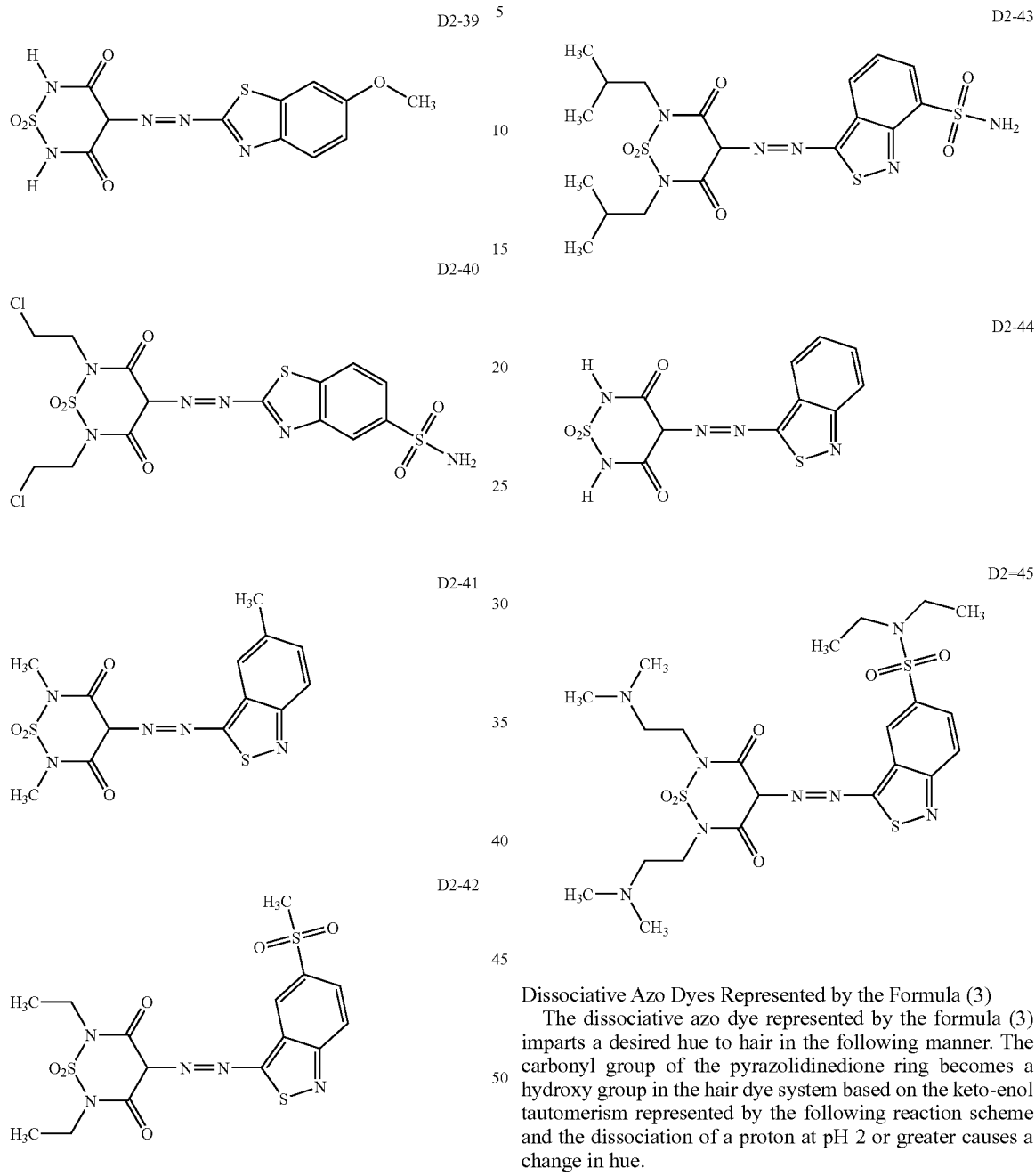

Dissociative Azo Dyes Represented by the Formula (3)

The dissociative azo dye represented by the formula (3) imparts a desired hue to hair in the following manner. The carbonyl group of the pyrazolidinedione ring becomes a hydroxy group in the hair dye system based on the keto-enol tautomerism represented by the following reaction scheme and the dissociation of a proton at pH 2 or greater causes a change in hue.

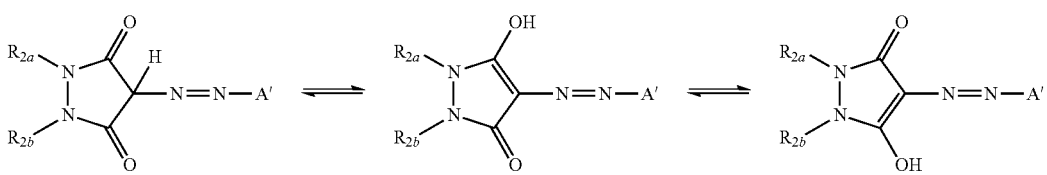

Examples of the $R_{2a}$, $R_{2b}$, and A' in the formula (3) except a hydrogen atom are similar to those described above in the description of the formula (2).
The following are specific examples of the dissociative azo dye represented by the formula (3) but they are not limited by the following examples.
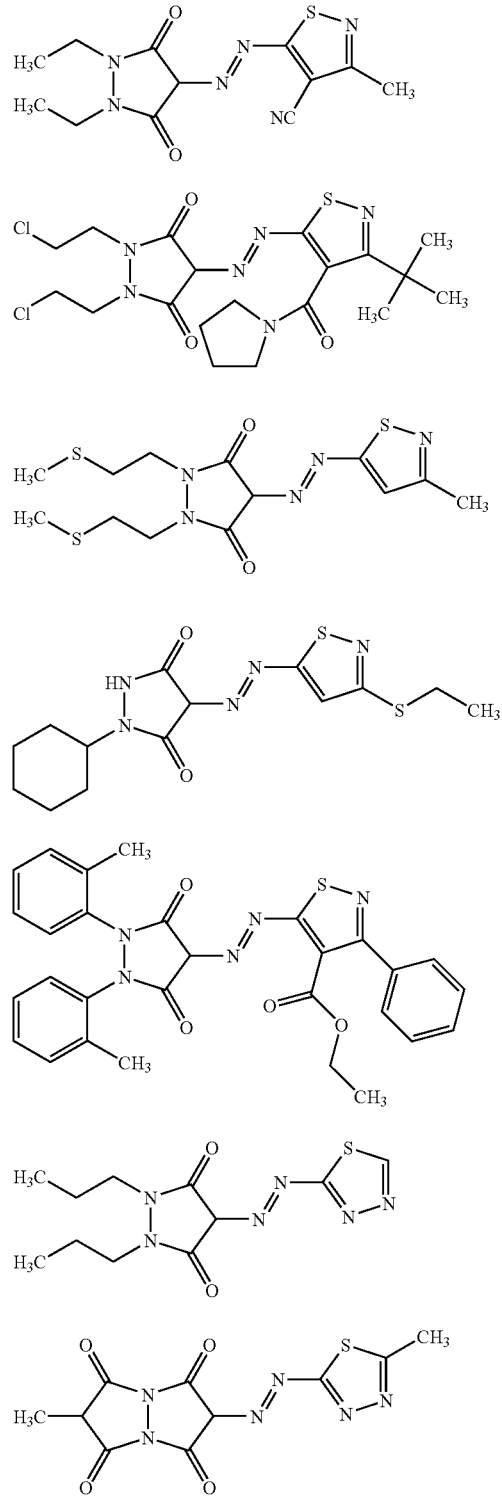
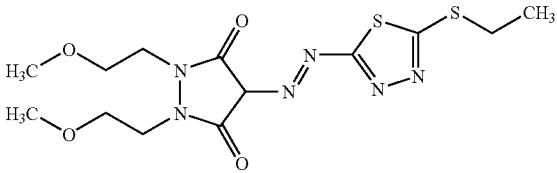
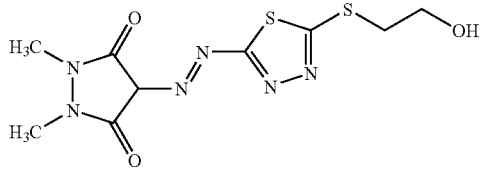
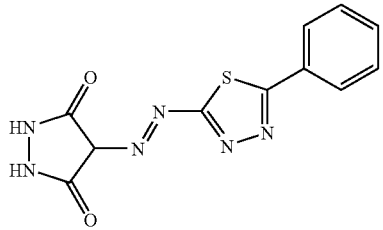
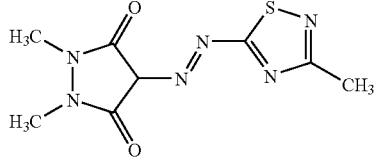
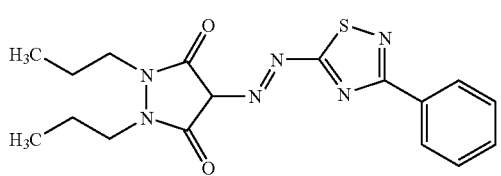
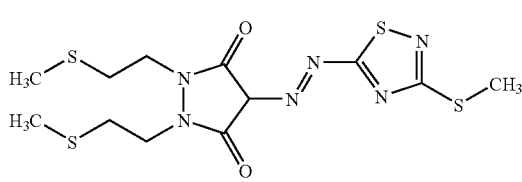
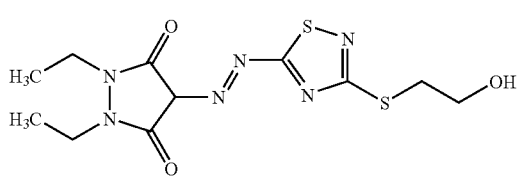
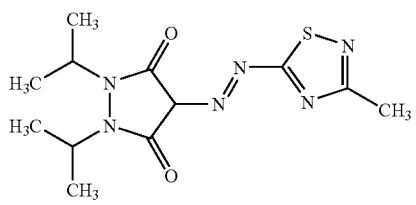

-continued

D3-16
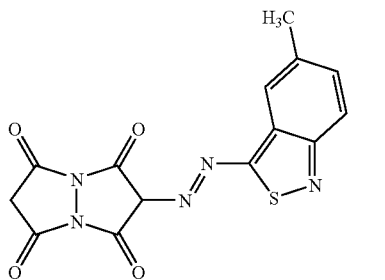

D3-17
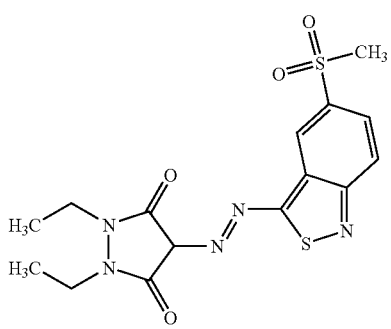

D3-18
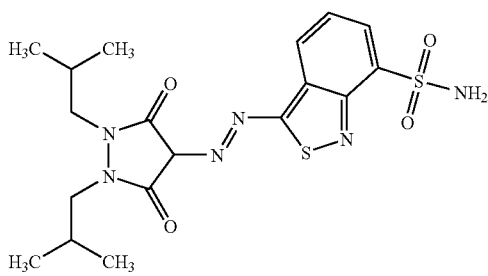

D3-19
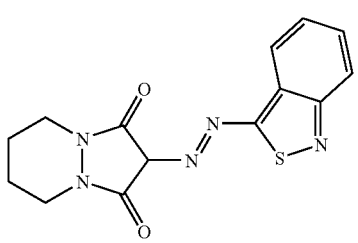

D3-20
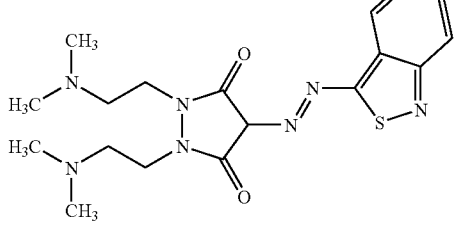

Dissociative Azo Dyes Represented by the Formula (4)

Examples of the substituent represented by $V_1$ or $V_2$ in the formula (4) include:

halogen atoms (such as a fluorine atom, a chlorine atom, and a bromine atom), a hydroxy group, an amino group, a mercapto group, alkyl groups (linear, branched, or cyclic alkyl groups having from 1 to 15 carbon atoms, preferably from 1 to 6 carbon atoms, such as a methyl group, an ethyl group, an n-propyl group, an isopropyl group, an s-butyl group, a t-butyl group, an n-octyl group, a 2-ethylhexyl group, a cyclopentyl group, and a cyclohexyl group), alkenyl groups (linear, branched, or cyclic alkenyl groups having from 2 to 10 carbon atoms, preferably from 2 to 6 carbon atoms, such as a vinyl group, an allyl group, a prenyl group, and a cyclopenten-1-yl group), alkynyl groups (alkynyl groups having from 2 to 10 carbon atoms, preferably from 2 to 6 carbon atoms, such as an ethynyl group and a propargyl group), aryl groups (aryl groups having from 6 to 16 carbon atoms, preferably from 6 to 10 carbon atoms, such as a phenyl group, an o-tolyl group, a p-tolyl group, and a naphthyl group), heterocyclic groups (monovalent groups having from 1 to 12, preferably from 2 to 6 carbon atoms, which are available by removing a hydrogen atom from 5- to 10-membered, preferably from 5- or 6-membered aromatic or non-aromatic heterocyclic compounds, such as a 1-pyrazolyl group, a 1-imidazolyl group, a 2-furyl group, a 2-thienyl group, a 4-pyrimidinyl group, a 2-pyridyl group, a 2-benzothiazolyl group, a 2-tetrahydrofuryl group, and a 2-morpholyl group), a nitro group, a cyano group, a carbamoyl group, a sulfamoyl group, acyl groups (a formyl group, alkylcarbonyl groups having from 2 to 10, preferably from 2 to 6 carbon atoms, arylcarbonyl groups having from 7 to 12, preferably from 7 to 9 carbon atoms, heterocyclic carbonyl groups having from 2 to 12, preferably from 2 to 6 carbon atoms, such as a formyl group, an acetyl group, a propionyl group, a pivaloyl group, a benzoyl group, and a 2-pyridylcarbonyl group), alkoxycarbonyl groups (alkoxycarbonyl groups having from 2 to 10, preferably from 2 to 6 carbon atoms, such as a methoxycarbonyl group, an ethoxycarbonyl group, a t-butoxycarbonyl group, and an isobutyloxycarbonyl group), aryloxycarbonyl groups (aryloxycarbonyl groups having from 7 to 12, preferably from 7 to 9 carbon atoms, such as a phenoxycarbonyl group and a naphthoxycarbonyl group), heterocyclic oxycarbonyl groups (heterocyclic oxycarbonyl groups having from 1 to 12, preferably from 2 to 6 carbon atoms, such as a 1-pyrazolyloxycarbonyl group, a 1-imidazolyloxycarbonyl group, a 2-furyloxycarbonyl group, a 2-thienyloxycarbonyl group, a 2-tetrahydrofuryloxycarbonyl group, and a 2-morphoryloxycarbonyl group), imido groups (imido groups having from 2 to 10, preferably from 4 to 8 carbon atoms, such as an N-succinimido group and an N-phthalimido group), alkylsulfinyl groups (alkylsulfinyl groups having from 1 to 10, preferably from 1 to 6 carbon atoms, such as a methylsulfinyl group and an ethylsulfinyl group), arylsulfinyl groups (arylsulfinyl groups having from 6 to 12, preferably from 6 to 8 carbon atoms, such as a phenylsulfinyl group), alkylsulfonyl groups (alkylsulfonyl groups having from 1 to 10, preferably from 1 to 6 carbon atoms, such as a methylsulfonyl group, an ethylsulfonyl group, and a cyclohexylsulfonyl group), arylsulfonyl groups (arylsulfonyl groups having from 6 to 12, preferably from 6 to 8 carbon atoms, such as a phenylsulfonyl group), heterocyclic sulfonyl groups (heterocyclic sulfonyl groups having from 1 to 12, preferably from 2 to 6 carbon atoms, such as a 2-tetrahydropyranylsulfonyl group), a phosphanyl group, a phosphoryl group, and a phosphinoyl group.

These substituents may have one or more substituents further. In this case, preferred examples of the one or more substituents include examples of the substituents described above. When the number of the substituents is two or more, the two or more substituents may be the same or different.

The following are examples of the substituent having a substituent further. Examples of the alkyl or aryl group having a substituent include:

aralkyl groups (aralkyl groups having from 7 to 18, preferably 7 to 12 carbon atoms, such as a benzyl group and a phenethyl group), haloalkyl groups (linear, branched, or cyclic haloalkyl groups having from 1 to 15, preferably from 1 to 6 carbon atoms, such as a chloromethyl group, a 2-chloroethyl group, a 2-bromopropyl group, and a 3-bromopropyl group), haloaryl groups (haloaryl groups having from 6 to 12, preferably from 6 to 8 carbon atoms, such as a p-chlorophenyl group, a 2,4-dichlorophenyl group, and a 3-fluorophenyl group), and hydroxyalkyl groups (linear, branched, or cyclic alkyl groups having from 1 to 15, preferably from 1 to 6 carbon atoms, such as a hydroxymethyl group, a 2-hydroxyethyl group, a 2-hydroxypropyl group, and a 3-hydroxypropyl group).

Examples of the hydroxy group having a substituent include:

alkoxy groups (linear, branched, or cyclic alkoxy groups having from 1 to 10, preferably from 1 to 6 carbon atoms, such as a methoxy group, an ethoxy group, an isopropoxy group, a t-butoxy group, and a cyclopentyloxy group), alkenyloxy groups (linear, branched, or cyclic alkenyloxy groups having from 2 to 10, preferably from 2 to 6 carbon atoms, such as a 2-buten-1-yloxy group), aryloxy groups (aryloxy groups having from 6 to 12, preferably from 6 to 10 carbon atoms, such as a phenoxy group, a 2-methylphenoxy group, and a 4-t-butylphenoxy group), silyloxy groups (silyloxy groups having from 3 to 10, preferably from 3 to 6 carbon atoms, such as a trimethylsilyloxy group and a t-butyldimethylsilyloxy group), heterocyclic oxy groups (heterocyclic oxy groups having from 1 to 12, preferably from 2 to 6 carbon atoms, such as a 1-phenyltetrazol-5-oxy group and a 2-tetrahydropyranyloxy group), alkylsulfonyloxy groups (linear, branched, or cyclic alkylsulfonyloxy groups having from 1 to 10, preferably from 1 to 6 carbon atoms, such as a methanesulfonyloxy group and an ethanesulfonyloxy group), arylsulfonyloxy groups (arylsulfonyloxy groups having from 6 to 12, preferably from 6 to 10 carbon atoms, such as a phenylsulfonyloxy group), heterocyclic sulfonyloxy groups (heterocyclic sulfonyloxy groups having from 1 to 12, preferably from 2 to 6 carbon atoms, such as a 2-pyridylsulfonyloxy group), acyloxy groups (acyloxy groups having from 1 to 12, preferably from 1 to 8 carbon atoms, such as a formyloxy group, an acetyloxy group, a pivaloyloxy group, and a benzoyloxy group), carbamoyloxy groups (carbamoyloxy groups having from 1 to 10, preferably from 1 to 6 carbon atoms, such as an N,N-dimethylcarbamoyloxy group, an N,N-diethylcarbamoyloxy group, and a morpholinocarbonyloxy group), alkoxycarbonyloxy groups (alkoxycarbonyloxy groups having from 2 to 10, preferably from 2 to 8 carbon atoms, such as a methoxycarbonyloxy group, an ethoxycarbonyloxy group, a t-butoxycarbonyloxy group, and an n-octyloxycarbonyloxy group), aryloxycarbonyloxy groups (aryloxycarbonyloxy groups having from 7 to 12, preferably from 7 to 10 carbon atoms, such as a phenoxycarbonyloxy group and a p-methoxyphenoxycarbonyloxy group), and dialkylphosphinyloxy groups (phosphinyloxy groups having from 2 to 12, preferably from 2 to 6 carbon atoms, such as a dimethylphosphinyloxy group and a dibutylphosphinyloxy group).

Examples of the amino group having a substituent include:

alkylamino groups (alkylamino groups having from 1 to 20, preferably from 1 to 12 carbon atoms, such as a methylamino group, a dimethylamino group, a cyclohexylmethylamino group, and a 1-pyrrolidyl group), arylamino groups (arylamino groups having from 6 to 16, preferably from 6 to 12 carbon atoms, such as an anilino group, an N-methylanilino group, and a diphenylamino group), heterocyclic amino groups (heterocyclic amino groups having from 1 to 12, preferably from 2 to 6 carbon atoms, such as a 2-pyridylamino group, a pyrazol-4-ylamino group, a benzimidazol-2-ylamino group, a benzothiazol-2-ylamino group, a benzoxazol-2-ylamino group, a 2-oxazolylamino group, a 1,2,4-triazol-3-ylamino group, a 1,2,4-thiadiazol-2-ylamino group, a 1,3,4-thiadiazol-2-ylamino group, a 1,2,4-oxadiazol-2-ylamino group, and a 1,3,4-oxadiazol-2-ylamino group), acylamino groups (alkylcarbonylamino groups having from 1 to 10, preferably from 1 to 6 carbon atoms, arylcarbonylamino groups having from 6 to 18, preferably from 6 to 12 carbon atoms, and heterocyclic carbonylamino groups having from 2 to 12, preferably from 2 to 6 carbon atoms, such as a formylamino group, an acetylamino group, an ethylcarbonylamino group, a pivaloylamino group, a benzoylamino group, a 4-pyridylcarbonylamino group), ureido groups (aminocarbonylamino groups having from 1 to 12, preferably from 1 to 8 carbon atoms, such as a carbamoylamino group, an N,N-dimethylaminocarbonylamino group, an N,N-diethylaminocarbonylamino group, and a morpholin-4-ylcarbonylamino group), alkoxycarbonylamino groups (alkoxycarbonylamino groups having from 2 to 10, preferably from 2 to 6 carbon atoms, such as a methoxycarbonylamino group, an ethoxycarbonylamino group, and a t-butoxycarbonylamino group), aryloxycarbonylamino groups (aryloxycarbonylamino groups having from 7 to 12, preferably from 7 to 9 carbon atoms, such as a phenoxycarbonylamino group), heterocyclic oxycarbonylamino groups (heterocyclic oxycarbonylamino groups having from 1 to 12, preferably from 2 to 6 carbon atoms, such as a 2-pyridyloxycarbonylamino group), sulfamoylamino groups (sulfamoylamino groups having from 0 to 10, preferably from 0 to 6 carbon atoms, such as a sulfamoylamino group and an N,N-dimethylaminosulfonylamino group), alkylsulfonylamino groups (alkylsulfonylamino groups having from 1 to 10, preferably from 1 to 6 carbon atoms, such as a methylsulfonylamino group, an ethylsulfonylamino group, and an n-butylsulfonylamino group), arylsulfonylamino groups (arylsulfonylamino groups having from 6 to 12, preferably from 6 to 8 carbon atoms, such as a phenylsulfonylamino group), and phosphinylamino groups (phosphinylamino groups having from 2 to 12, preferably from 2 to 6 carbon atoms, such as a dimethoxyphosphinylamino group and a dimethylaminophosphinylamino group).

Examples of the mercapto group having a substituent include:

alkylthio groups (alkylthio groups having from 1 to 10, preferably from 1 to 6 carbon atoms, such as a methylthio group, an ethylthio group, and a butylthio group), arylthio groups (arylthio groups having from 6 to 12, preferably from 6 to 8 carbon atoms, such as a phenylthio group), and heterocyclic thio groups (heterocyclic thio groups having from 1 to 10, preferably from 1 to 6 carbon atoms, such as a 2-benzothiazolylthio group, and a 1-phenyltetrazol-5-ylthio group).

Examples of the carbamoyl group having a substituent include:

alkylcarbamoyl groups (carbamoyl groups having from 1 to 12, preferably from 1 to 8 carbon atoms, such as a methylcarbamoyl group, a dimethylcarbamoyl group, a diethylcarbamoyl group, and a 1-pyrrolidylcarbamoyl group), and sulfamoylcarbamoyl groups (sulfamoylcarbamoyl groups having from 1 to 12, preferably from 1 to 8 carbon atoms, such as an N-(sulfamoyl)carbamoyl group, and an N—(N',N'-dimethylsulfamoyl)carbamoyl group).

Examples of the sulfamoyl group having a substituent include:

alkylsulfamoyl groups (alkylsulfamoyl groups having from 1 to 12, preferably from 1 to 6 carbon atoms, such as an ethylsulfamoyl group, a dimethylsulfamoyl group, a dibutylsulfamoyl group, an ethylmethylsulfamoyl group, a diethylsulfamoyl group, and an N-cyclohexyl-N-methylsulfamoyl group), arylsulfamoyl groups (arylsulfamoyl groups having from 6 to 12, preferably from 6 to 8 carbon atoms, such as a phenylsulfamoyl group), and carbamoylsulfamoyl groups (carbamoylsulfamoyl groups having from 1 to 12, preferably from 1 to 6 carbon atoms, such as an N-(carbamoyl)sulfamoyl group).

Examples of the phosphoryl group having a substituent include:

alkylphosphoryl groups (alkylphosphoryl groups having from 1 to 12, preferably 1 to 6 carbon atoms, such as a methylphosphoryl group and an ethylphosphoryl group).

Examples of the substituent having a substituent, the latter substituent having a substituent further, include:

alkoxyalkyl groups (linear, branched, or cyclic alkoxyalkyl groups having from 1 to 32, preferably from 1 to 12 carbon atoms, such as a methoxymethyl group, a methoxyethyl group, an ethoxyethyl group, and a cyclohexyloxypropyl group), alkoxyaryl groups (alkoxyaryl groups having from 7 to 18, preferably from 7 to 12 carbon atoms, such as a p-methoxyphenyl group and a 2,4-dimethoxyphenyl group), alkoxycarbonylalkyl groups (alkoxycarbonylalkyl groups having from 2 to 15, preferably from 2 to 6 carbon atoms, such as a methoxycarbonylethyl group and a 3-ethoxycarbonylpropyl group), alkylaminoalkyl groups (alkylamino alkyl groups having from 2 to 15, preferably from 2 to 6 carbon atoms, such as an N-methylaminomethyl group and a dimethylaminoethyl group), alkylthioalkyl groups (alkylthioalkyl groups having from 2 to 15, preferably from 2 to 6 carbon atoms, such as a methylthiomethyl group, a methylthioethyl group, and an ethylthioethyl group), haloalkoxyaryl groups (haloalkoxyaryl groups having from 7 to 18, preferably from 7 to 12 carbon atoms, such as a 2-chloro-4-methoxyphenyl group and a 2,5-dichloro-4-methoxyphenyl group), alkoxycarbonyloxy groups (alkoxycarbonyloxy groups having from 2 to 15, preferably from 2 to 6 carbon atoms, such as a methoxycarbonyloxy group and an ethoxycarbonyloxy group), aryloxycarbonyloxy groups (aryloxycarbonyloxy groups having from 7 to 18, preferably from 7 to 12 carbon atoms, such as a phenoxycarbonyloxy group), alkoxycarbonylamino groups (alkoxycarbonylamino groups having from 2 to 10, preferably from 2 to 6 carbon atoms, such as a methoxycarbonylamino group, an ethoxycarbonylamino group, a t-butoxycarbonylamino group, and an isobutyloxycarbonylamino group), and hydroxyalkylthio groups (hydroxyalkylthio groups having from 1 to 15, preferably from 1 to 6 carbon atoms, such as a hydroxyethylthio group and a 2-hydroxypropylthio group).

The substituent represented by $V_1$ or $V_2$ is preferably an alkyl group, an aryl group, a halogen atom, a cyano group, a carbamoyl group, a sulfamoyl group, an alkylsulfonyl group, an arylsulfonyl group, or an acylamino group. As the alkyl group, a methyl group, an ethyl group, and a t-butyl group are preferred, with a methyl group and an ethyl group being more preferred. As the aryl group, a phenyl group and a naphthyl group are preferred, with a phenyl group being more preferred. As the halogen atom, a chlorine atom and a fluorine atom are preferred. The carbamoyl group and the sulfamoyl group preferably have no substituent. As the alkylsulfonyl group, a methylsulfonyl group and an ethylsulfonyl group are preferred. As the arylsulfonyl group, a phenylsulfonyl group and a p-toluenesulfonyl group are preferred. As the acylamino group, an acetylamino group and a propionylamino group are preferred.

A plurality of $V_1$s or a plurality of $V_2$s may be the same or different. Alternatively, the plurality of $V_1$s or the plurality of $V_2$s may be coupled together to form a ring (aromatic or nonaromatic hydrocarbon ring or heterocyclic ring including a polycyclic fused ring and a ring assembly). Preferred examples of the ring include a benzene ring, a naphthalene ring, an anthracene ring, a phenanthrene ring, a fluorene ring, a triphenylene ring, naphthacene ring, a biphenyl ring, a pyrrole ring, a furan ring, a thiophene ring, an imidazole ring, an oxazole ring, a thiazole ring, a pyridine ring, a pyrazine ring, a pyrimidine ring, a pyridazine ring, an indolidine ring, an indole ring, a benzofuran ring, a benzothiophene ring, an isobenzofuran ring, a quinolidine ring, a quinoline ring, a phthalazine ring, a naphthylidine ring, a quinoxaline ring, a quinoxazoline ring, an isoquinoline ring, a carbazole ring, a phenanthridine ring, an acridine ring, a phenanthroline ring, a thianthrene ring, a chromene ring, a xanthene ring, a phenoxathiin ring, a phenothiazine ring and a phenazine ring. Of these, a benzene ring, a naphthalene ring, and a pyridine ring are preferred.

$X_1$, $X_2$, $X_3$ and $X_4$ are coupled together with the carbon atom sandwiched between $X_1$ and $X_4$ to form a 5-membered heteroaromatic ring and examples include a carbon atom, a nitrogen atom, a sulfur atom, and an oxygen atom. Specific examples of such a 5-membered heteroaromatic ring include a furan ring, a pyrrole ring, a thiophene ring, an imidazole ring, a pyrazole ring, a thiazole ring, an isothiazole ring, an oxazole ring, an isoxazole ring, a triazole ring, a tetrazole ring, a thiadiazole ring, an oxadiazole ring, an oxatriazole ring, and a thiatriazole ring. Of these, a pyrazole ring, an isothiazole ring, an imidazole ring, and a thiazole ring are preferred, with an isothiazole ring, a pyrazole ring, and an imidazole ring being more preferred. The following formulas (i) to (iii) are preferable heteroaromatic ring structures shown together with $(V_2)_{a2}$.

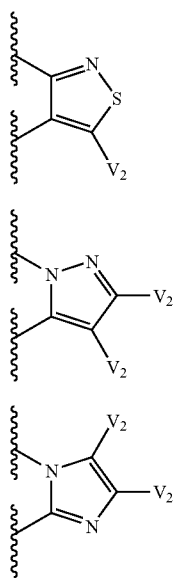

R represents a coupler component. The term "coupler component" as used herein means a partial structure derived from a coupler compound capable of reacting with a diazonium salt to provide an azo dye. This concept is popularly used in the field of azo dyes. In the present invention, R is required to have a dissociative proton and it is, for example, a group represented by the following formula (C):

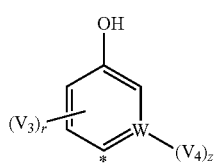

[wherein, the symbol * means a carbon atom which is bonded to the azo portion of the formula (4), $V_3$ represents a substituent, r stands for an integer from 0 to 3, $V_4$ represents a hydrogen atom or a substituent, and W stands for a carbon atom or a nitrogen atom, with the proviso that when W represents a carbon atom, z stands for 1 and when W represents a nitrogen atom, z stands for 0].

Examples of the substituent represented by $V_3$ or $V_4$ include those described as the substituent represented by $V_1$ or $V_2$. When there are two or more $V_3$s, they may be the same or different. When two or more $V_3$s, or $V_3$ and $V_4$ are adjacent to each other, they may be coupled together to form a ring (aromatic or non-aromatic hydrocarbon ring or heterocyclic ring) or they may form a polycyclic fused ring or ring assembly.

Examples of the coupler component represented by the formula (C) include groups represented by the following formulas (Cp-1) and (Cp-2):

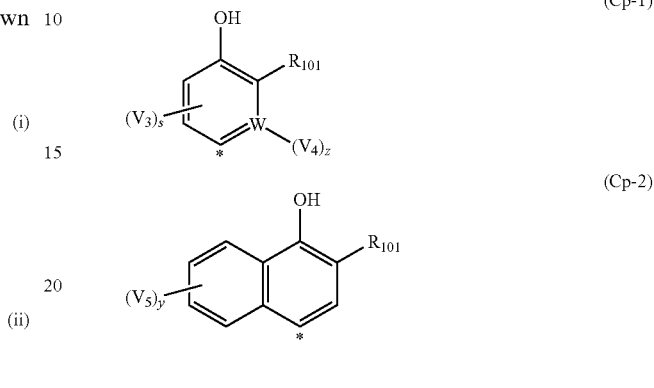

[wherein, *, $V_3$, $V_4$, W, and z have the same meanings as described above, $R_{101}$ represents a hydrogen atom, a halogen atom, a carbamoyl group, a sulfamoyl group, an acylamino group, an ureido group, or a sulfamoylamino group, $V_5$ represents a group exemplified above as the substituent represented by $V_1$ or $V_2$, s stands for an integer from 0 to 2, and y stands for an integer from 0 to 4].

When there are two or more $V_3$s or $V_5$s, they may be the same or different. When the two or more $V_3$s or $V_5$s are adjacent to each other, they may be coupled together to form a saturated or unsaturated, 5-membered or 6-membered cyclic structure.

These substituents may further have, if possible, the substituent represented by $V_1$ or $V_2$, preferably an alkyl group having from 1 to 10 carbon atoms, an aryl group having from 6 to 10 carbon atoms, or a heterocyclic group having from 1 to 10 carbon atoms. In the formula (Cp-1), it is preferred that W represents a carbon atom, z stands for 1, and $V_4$ represents a hydrogen atom. In the formula (Cp-2), $V_5$ is placed preferably at the 5- or 8-position of the 1-naphthol ring.

Examples of R include, in addition to the groups represented by the formulas (Cp-1) and (Cp-2), groups represented by the following formulas (Cp-3) to (Cp-13). It is to be noted that they are typically components collectively called "phenolic coupler" (Cp-1), "naphthol coupler" (Cp-2), "active methylene couplers" (Cp-3) to (Cp-6), "pyrazolone coupler" (Cp-7), "pyrazoloazole coupler" (Cp-8), "isoxazolone coupler" (Cp-9), and "pyrrotriazole couplers" (Cp-10) to (Cp-13).

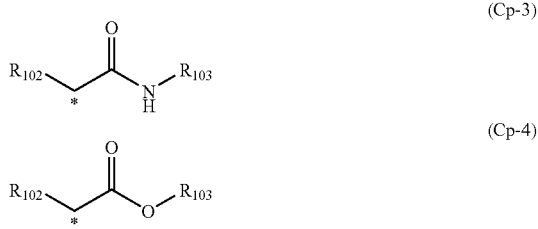

-continued

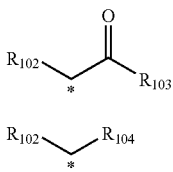
(Cp-5)

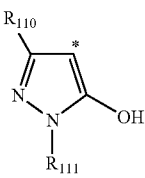
(Cp-6)

[wherein, * has the same meaning as described above, $R_{102}$ represents an acyl group, a cyano group, a nitro group, an aryl group, a heterocyclic group, an alkoxycarbonyl group, an aryloxycarbonyl group, a carbamoyl group, a sulfamoyl group, an alkylsulfonyl group, or an arylsulfonyl group, $R_{103}$ represents an alkyl group, an aryl group, or a heterocyclic group, and $R_{104}$ represents an aryl group or a heterocyclic group, wherein $R_{102}$, $R_{103}$, and $R_{104}$ each may have, if possible, the above-described substituent represented by $V_1$ or $V_2$ where the groups adjacent to each other may be coupled together to form a saturated or unsaturated, 5- or 6-membered cyclic structure, and $R_{102}$ and $R_{103}$ or $R_{102}$ and $R_{104}$ may be coupled together to form a ring].

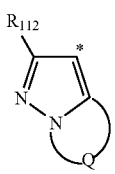
(Cp-7)

[wherein, * has the same meaning as described above, $R_{110}$ represents a hydrogen atom, an acyl group, a cyano group, a nitro group, an alkyl group, an aryl group, a heterocyclic group, an alkoxycarbonyl group, an aryloxycarbonyl group, a carbamoyl group, a sulfamoyl group, an alkylsulfonyl group, or an arylsulfonyl group and it may have, if possible, a substituent further, and $R_{111}$ represents a hydrogen atom, an aryl group, or a phenyl group and it may have, if possible, a substituent further].

Examples of the substituent which $R_{111}$ may have include those described above as the substituents represented by $V_1$ and $V_2$. The groups adjacent to each other may be coupled together to form a saturated or unsaturated, 5-membered or 6-membered cyclic structure.

(Cp-8)

[wherein, * has the same meaning as described above, $R_{112}$ represents a hydrogen atom, an acyl group, a cyano group, a nitro group, an alkyl group, an aryl group, a heterocyclic group, an alkoxycarbonyl group, an aryloxycarbonyl group, a carbamoyl group, a sulfamoyl group, an alkylsulfonyl group, or an arylsulfonyl group and it may have, if possible, a substituent further].

Examples of the substituent which $R_{112}$ may have include those described above as the substituents represented by $V_1$ and $V_2$. The groups adjacent to each other may be coupled together to form a saturated or unsaturated, 5-membered or 6-membered cyclic structure.

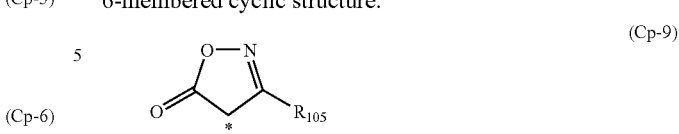
(Cp-9)

[wherein, $R_{105}$ represents a hydrogen atom, an acyl group, a cyano group, a nitro group, an alkyl group, an aryl group, a heterocyclic group, an alkoxycarbonyl group, an aryloxycarbonyl group, a carbamoyl group, an acylamino group, an arylamino group, an alkoxy group, an aryloxy group, a sulfamoyl group, an alkylsulfonyl group, or an arylsulfonyl group and it may have, if possible a substituent further].

Examples of the substituent which $R_{105}$ may have include those described above as the substituents represented by $V_1$ and $V_2$.

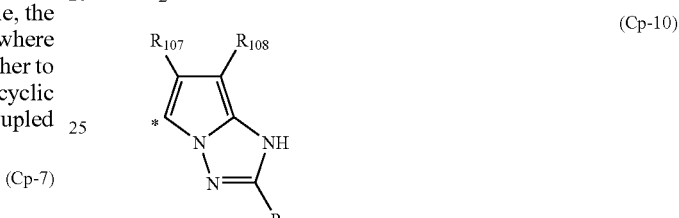
(Cp-10)

(Cp-11)

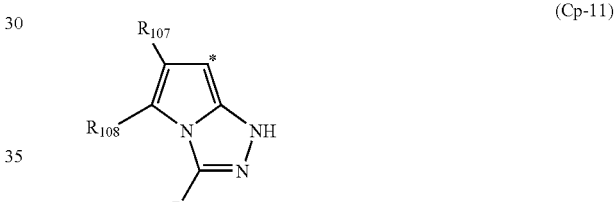
(Cp-12)

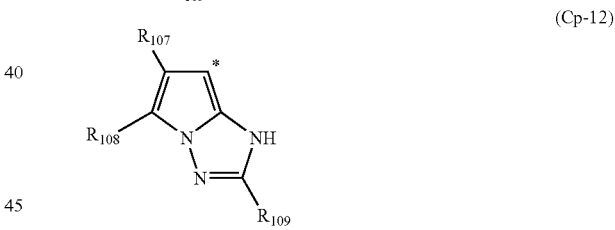
(Cp-13)

[wherein, * has the same meaning as described above, and $R_{107}$, $R_{108}$, and $R_{109}$ each represents a hydrogen atom or a substituent].

Examples of the substituent of $R_{107}$, $R_{108}$, and $R_{109}$ include those described above as the substituents represented by $V_1$ and $V_2$. The groups adjacent to each other may be coupled together to form a saturated or unsaturated, 5-membered or 6-membered cyclic structure.

Of these coupler components, a phenolic coupler (Cp-1) and a naphthol coupler (Cp-2) are more preferred from the standpoint of an effect as a coupler.

The following are specific examples of the dissociative azo dye represented by the formula (4) but they are not limited to the following examples.
D4-1
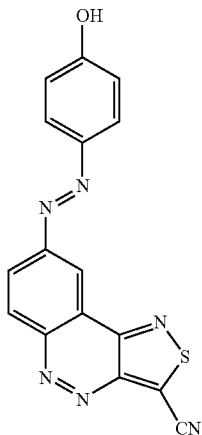
D4-2
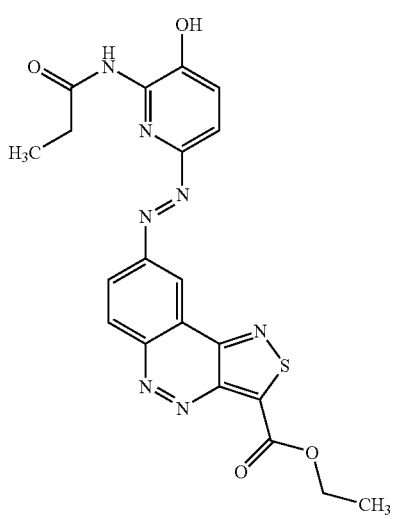
D4-3
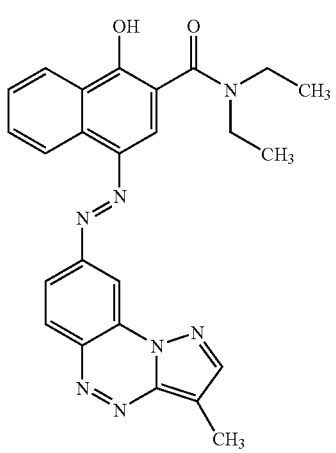
D4-4
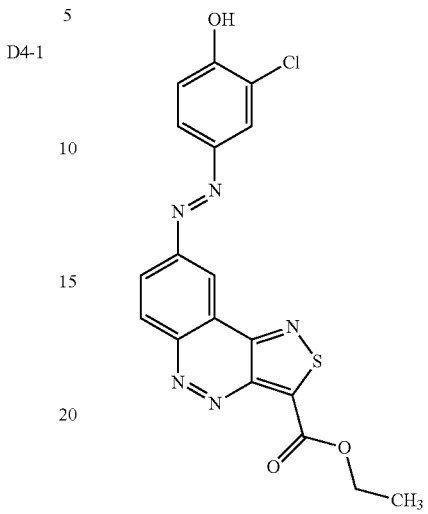
D4-5
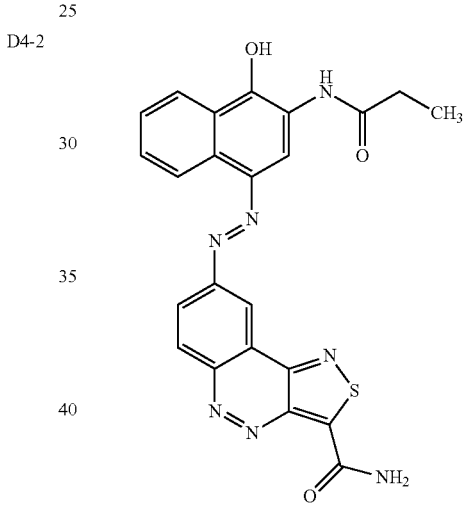
D4-6
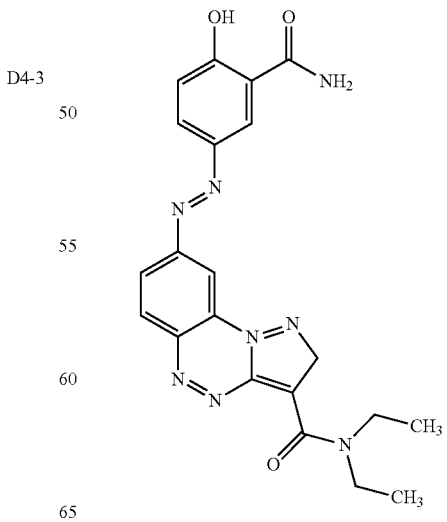

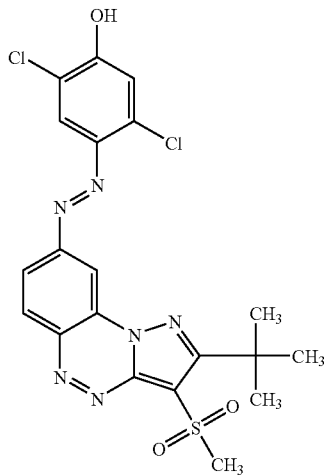
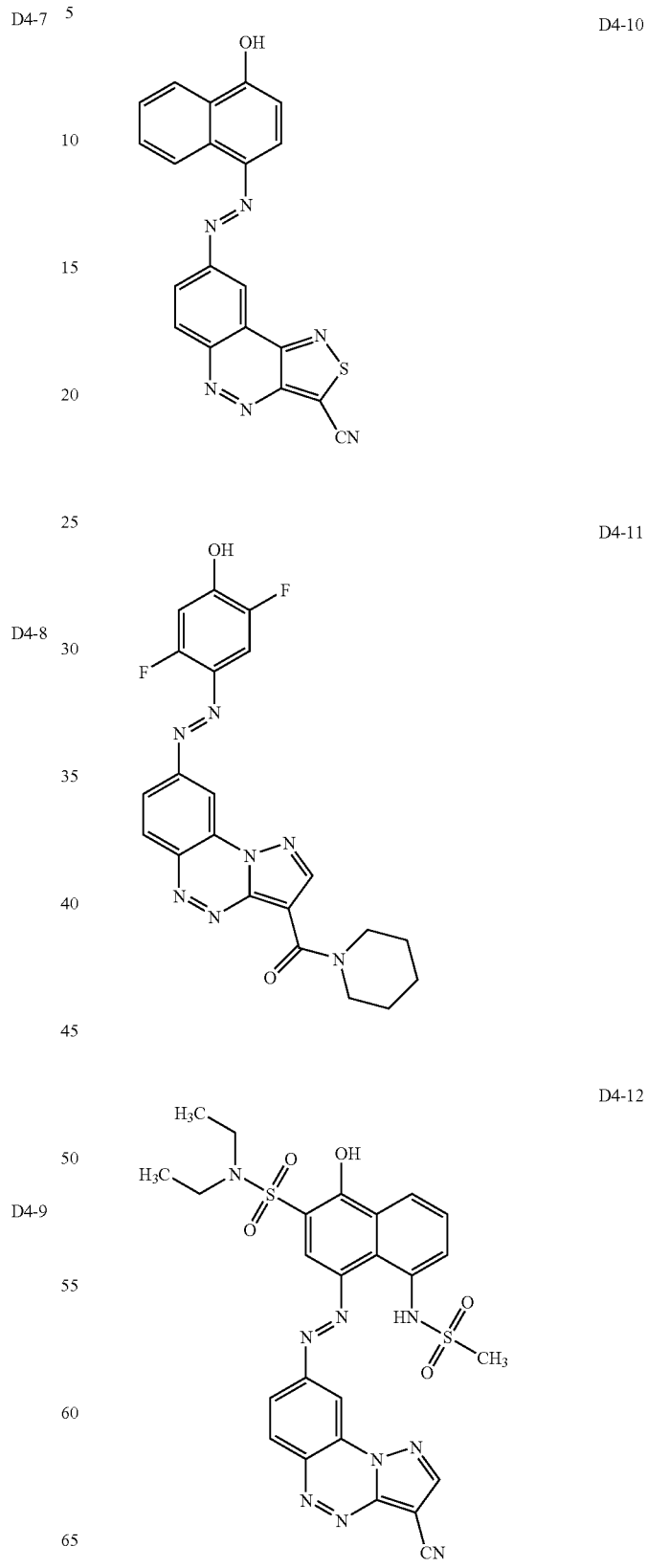

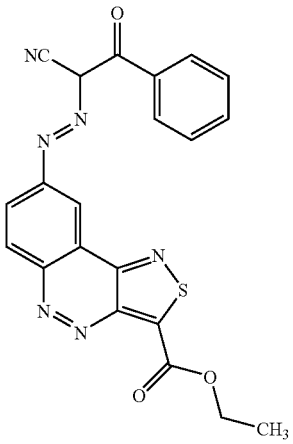
D4-13
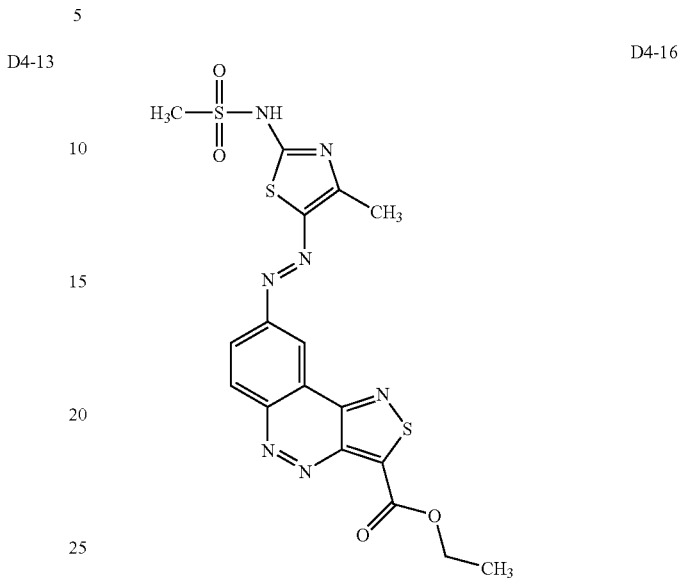
D4-16
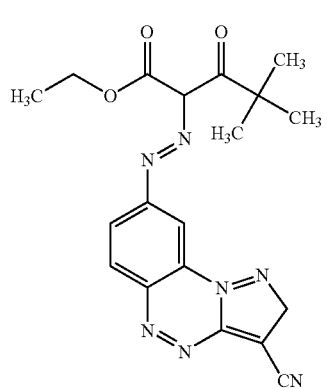
D4-14
D4-17
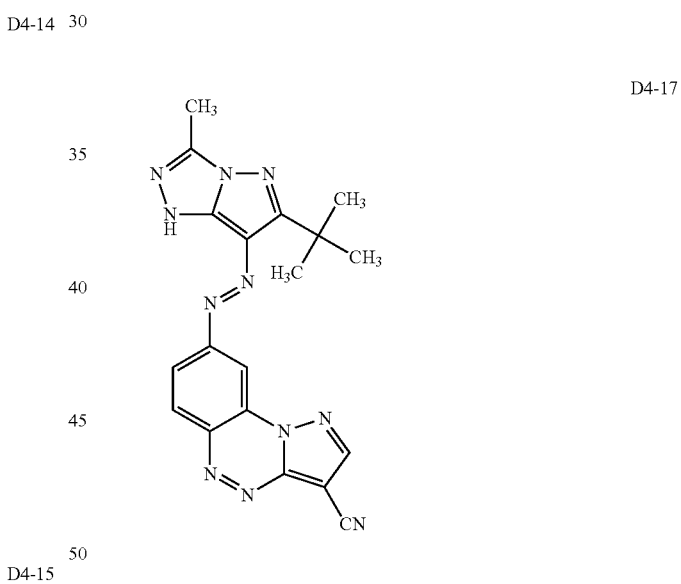
D4-15
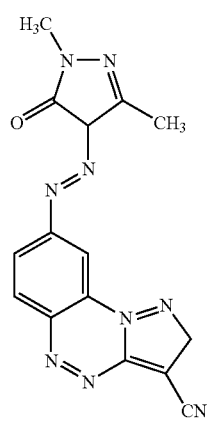
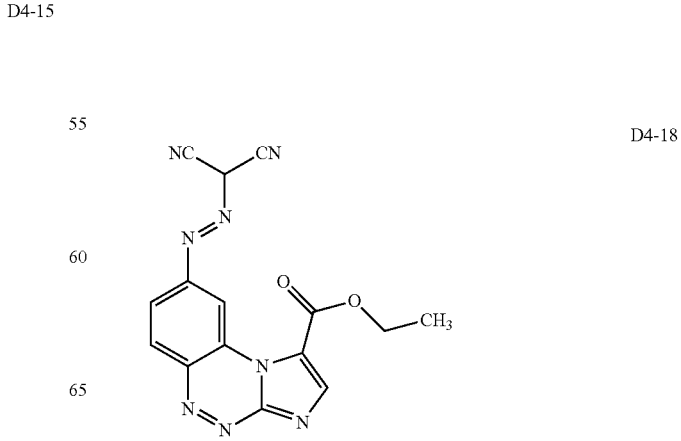
D4-18

-continued
D4-19
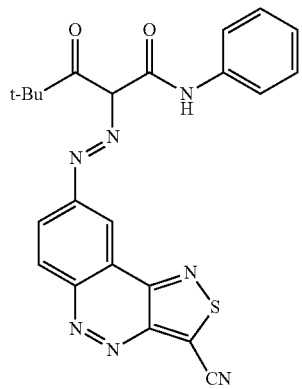
D4-22
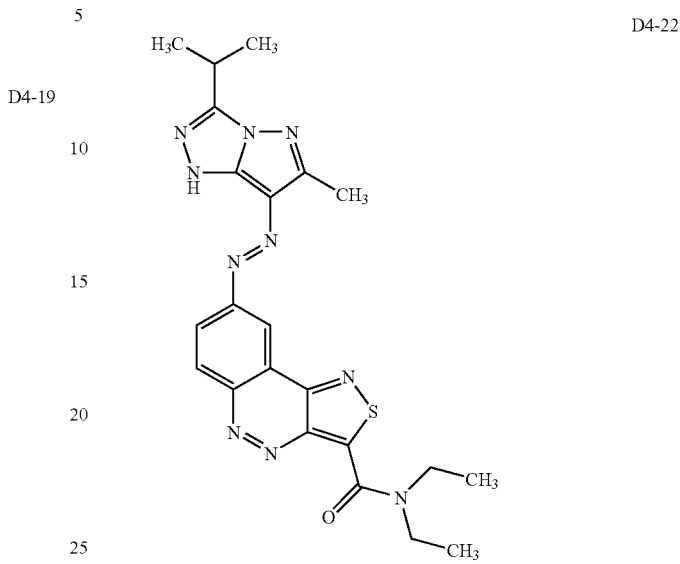
D4-20
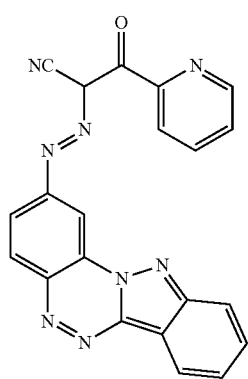
D4-23
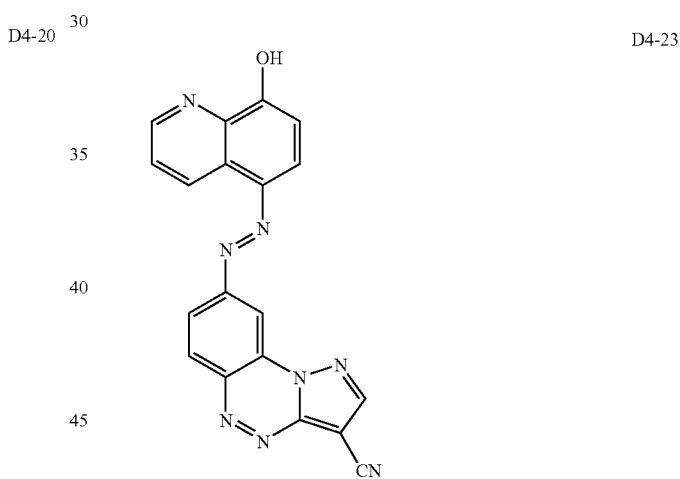
D4-21
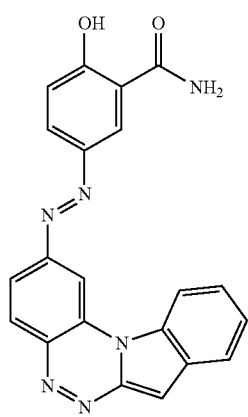
D4-24
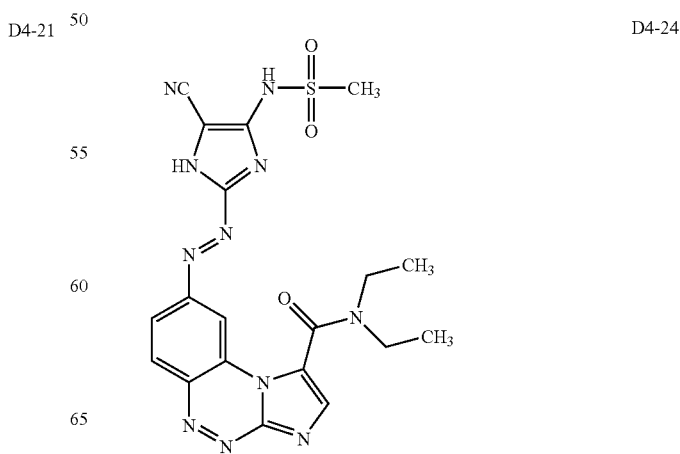

-continued
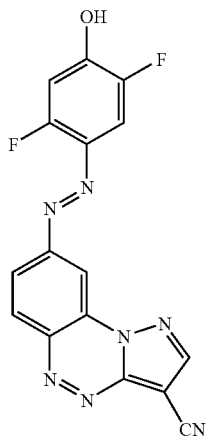
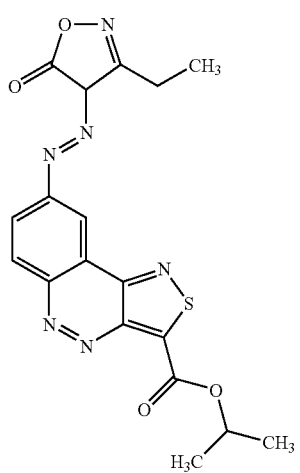
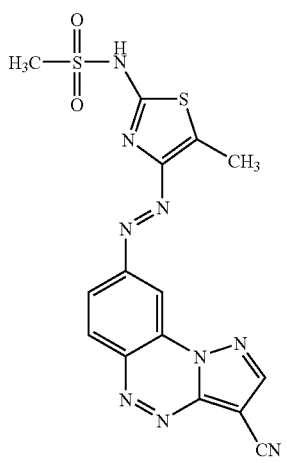
-continued
D4-25
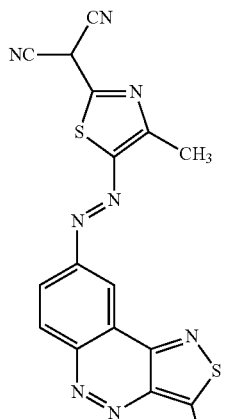
D4-26
D4-27
D4-28
D4-29
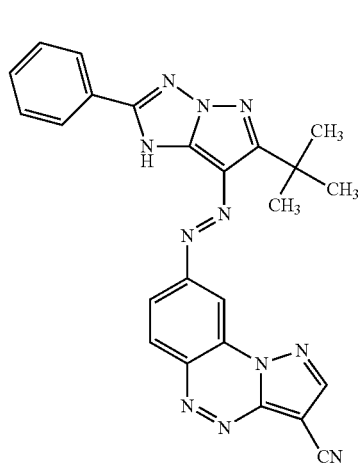
D4-30
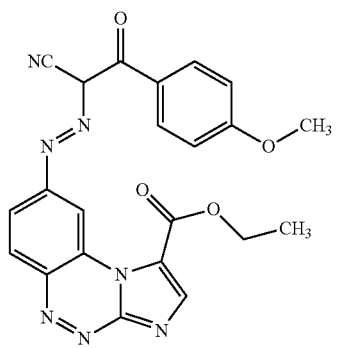

-continued
D4-31
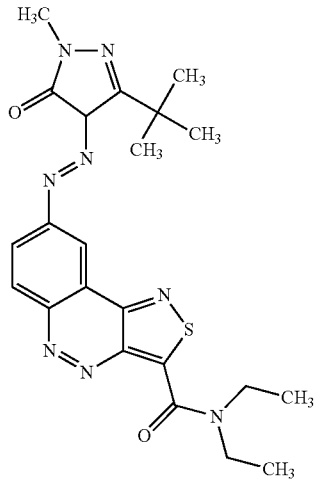
D4-34
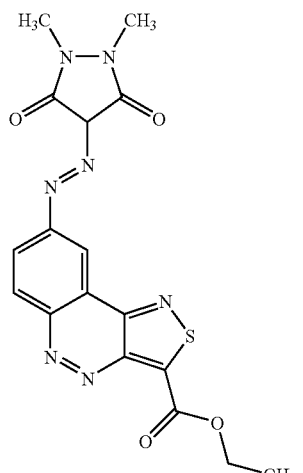
D4-32
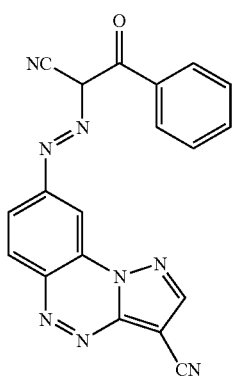
D4-35
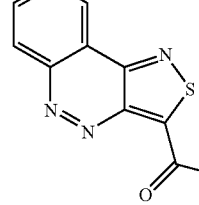
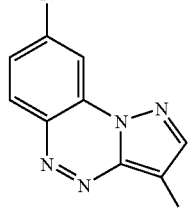
D4-33
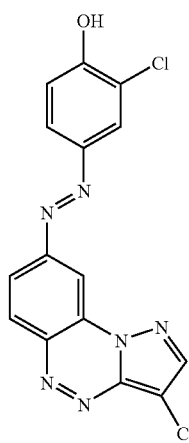
D4-36
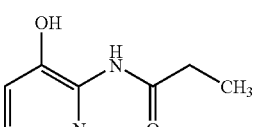

-continued

D4-37
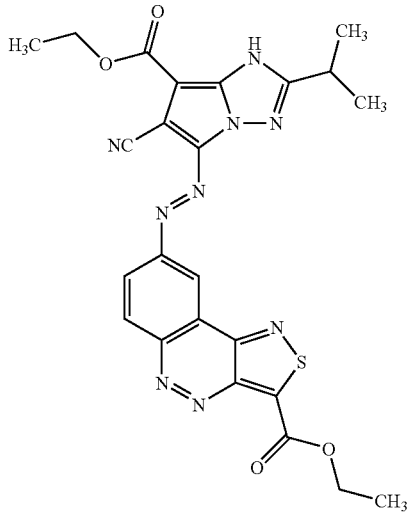

D4-38
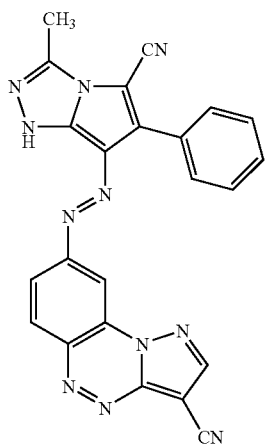

D4-39
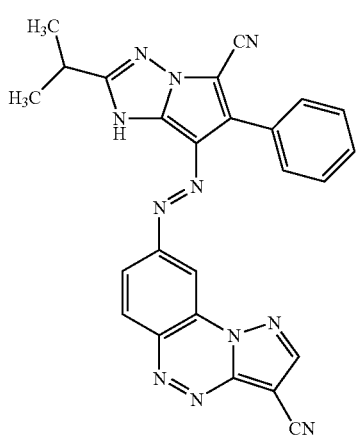

-continued

D4-40
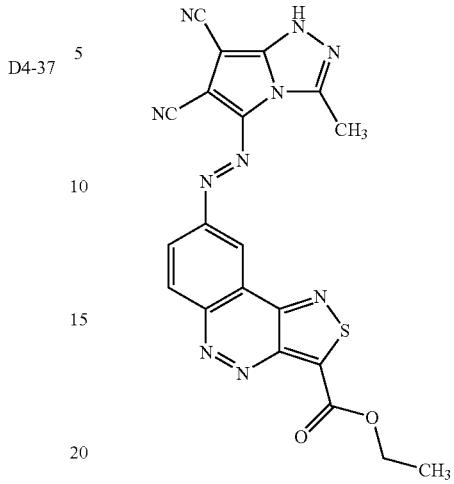

The Dissociative Azo Dye Represented by the Formula (5)

Examples of $R_6$ to $R_8$ in the formula (5) include:

halogen atoms (such as a fluorine atom, a chlorine atom, and a bromine atom), a hydroxy group, an amino group, a mercapto group, alkyl groups (linear, branched, or cyclic alkyl groups having from 1 to 15, preferably from 1 to 6 carbon atoms, such as a methyl group, an ethyl group, an n-propyl group, an isopropyl group, an s-butyl group, a t-butyl group, an n-octyl group, a 2-ethylhexyl group, a cyclopentyl group, and a cyclohexyl group), alkenyl groups (linear, branched, or cyclic alkenyl groups having from 2 to 10, preferably from 2 to 6 carbon atoms, such as a vinyl group, an allyl group, a prenyl group, and a cyclopenten-1-yl group), alkynyl groups (alkynyl groups having from 2 to 10, preferably from 2 to 6 carbon atoms, such as an ethynyl group and a propargyl group), aryl groups (aryl groups having from 6 to 16, preferably from 6 to 10 carbon atoms, such as a phenyl group, an o-tolyl group, a p-tolyl group, and a naphthyl group), heterocyclic groups (monovalent groups having from 1 to 12, preferably from 2 to 6 carbon atoms, which are available by removing a hydrogen atom from 5- to 10-membered, preferably from 5- or 6-membered aromatic or non-aromatic heterocyclic compounds, such as a 1-pyrazolyl group, a 1-imidazolyl group, a 2-furyl group, a 2-thienyl group, a 4-pyrimidinyl group, a 2-pyridyl group, a 2-benzothiazolyl group, a 2-tetrahydrofuryl group, and a 2-morpholyl group)

a nitro group, a cyano group, a carbamoyl group, a sulfamoyl group, acyl groups (a formyl group, alkylcarbonyl groups having from 2 to 10, preferably from 2 to 6 carbon atoms, arylcarbonyl groups having from 7 to 12, preferably from 7 to 9 carbon atoms, heterocyclic carbonyl groups having from 2 to 12, preferably from 2 to 6 carbon atoms, such as a formyl group, an acetyl group, a propionyl group, a pivaloyl group, a benzoyl group, and a 2-pyridylcarbonyl group), alkoxycarbonyl groups (alkoxycarbonyl groups having from 2 to 10, preferably from 2 to 6 carbon atoms, such as a methoxycarbonyl group, an ethoxycarbonyl group, a t-butoxycarbonyl group, and an isobutyloxycarbonyl group), aryloxycarbonyl groups (aryloxycarbonyl groups having from 7 to 12, preferably from 7 to 9 carbon atoms, such as a phenoxycarbonyl group and a naphthoxycarbonyl group), heterocyclic oxycarbonyl groups (heterocyclic oxycarbonyl groups having from 1 to 12, preferably from 2 to 6 carbon atoms, such as a 1-pyrazolyloxycarbonyl group, a 1-imidazolyloxycarbonyl group, a 2-furyloxycarbonyl group, a 2-thienyloxycarbonyl group, a 2-tetrahydrofuryloxycarbonyl group, and a 2-morpholyloxycarbonyl group), imido groups (imido groups having from 2 to 10, preferably from 4 to 8 carbon atoms, such as an N-succinimido group and an N-phthalimido group), alkylsulfinyl groups (alkylsulfinyl groups having from 1 to 10, preferably from 1 to 6 carbon atoms, such as a methylsulfinyl group and an ethylsulfinyl group), arylsulfinyl groups (arylsulfinyl groups having from 6 to 12, preferably from 6 to 8 carbon atoms, such as a phenylsulfinyl group), alkylsulfonyl groups (alkylsulfonyl groups having from 1 to 10, preferably from 1 to 6 carbon atoms, such as a methylsulfonyl group, an ethylsulfonyl group, and a cyclohexylsulfonyl group), arylsulfonyl groups (arylsulfonyl groups having from 6 to 12, preferably from 6 to 8 carbon atoms, such as a phenylsulfonyl group), heterocyclic sulfonyl groups (heterocyclic sulfonyl groups having from 1 to 12, preferably from 2 to 6 carbon atoms, such as a 2-tetrahydropyranylsulfonyl group), a phosphanyl group, a phosphoryl group, and a phosphinoyl group.

Examples also include these substituents having one or more substituents further. In this case, preferred examples of the one or more substituents include those described above as the substituents. When the number of the substituents is two or more, the two or more substituents may be the same or different.

The following are examples of the substituent having a substituent further. Examples of the alkyl or aryl group having a substituent include:

aralkyl groups (aralkyl groups having from 7 to 18, preferably 7 to 12 carbon atoms, such as a benzyl group and a phenethyl group), haloalkyl groups (linear, branched, or cyclic haloalkyl groups having from 1 to 15, preferably from 1 to 6 carbon atoms, such as a chloromethyl group, a 2-chloroethyl group, a 2-bromopropyl group, and a 3-bromopropyl group), haloaryl groups (haloaryl groups having from 6 to 12, preferably from 6 to 8 carbon atoms, such as a p-chlorophenyl group, a 2,4-dichlorophenyl group, and a 3-fluorophenyl group), and hydroxyalkyl groups (linear, branched, or cyclic alkyl groups having from 1 to 15, preferably from 1 to 6 carbon atoms, such as a hydroxymethyl group, a 2-hydroxyethyl group, a 2-hydroxypropyl group, and a 3-hydroxypropyl group).

Examples of the hydroxy group having a substituent include:

alkoxy groups (linear, branched, or cyclic alkoxy groups having from 1 to 10, preferably from 1 to 6 carbon atoms, such as a methoxy group, an ethoxy group, an isopropoxy group, a t-butoxy group, and a cyclopentyloxy group), alkenyloxy groups (linear, branched, or cyclic alkenyloxy groups having from 2 to 10, preferably from 2 to 6 carbon atoms, such as a 2-buten-1-yloxy group), aryloxy groups (aryloxy groups having from 6 to 12, preferably from 6 to 10 carbon atoms, such as a phenoxy group, a 2-methylphenoxy group, and a 4-t-butylphenoxy group), silyloxy groups (silyloxy groups having from 3 to 10, preferably from 3 to 6 carbon atoms, such as a trimethylsilyloxy group and a t-butyldimethylsilyloxy group), heterocyclic oxy groups (heterocyclic oxy groups having from 1 to 12, preferably from 2 to 6 carbon atoms, such as a 1-phenyltetrazol-5-oxy group and a 2-tetrahydropyranyloxy group), alkylsulfonyloxy groups (linear, branched, or cyclic alkylsulfonyloxy groups having from 1 to 10, preferably from 1 to 6 carbon atoms, such as a methanesulfonyloxy group and an ethanesulfonyloxy group), arylsulfonyloxy groups (arylsulfonyloxy groups having from 6 to 12, preferably from 6 to 10 carbon atoms, such as a phenylsulfonyloxy group), heterocyclic sulfonyloxy groups (heterocyclic sulfonyloxy groups having from 1 to 12, preferably from 2 to 6 carbon atoms, such as a 2-pyridylsulfonyloxy group), acyloxy groups (acyloxy groups having from 1 to 12, preferably from 1 to 8 carbon atoms, such as a formyloxy group, an acetyloxy group, a pivaloyloxy group, and a benzoyloxy group), carbamoyloxy groups (carbamoyloxy groups having from 1 to 10, preferably from 1 to 6 carbon atoms, such as an N,N-dimethylcarbamoyloxy group, an N,N-diethylcarbamoyloxy group, and a morpholinocarbonyloxy group), alkoxycarbonyloxy groups (alkoxycarbonyloxy groups having from 2 to 10, preferably from 2 to 8 carbon atoms, such as a methoxycarbonyloxy group, an ethoxycarbonyloxy group, a t-butoxycarbonyloxy group, and an n-octyloxycarbonyloxy group), aryloxycarbonyloxy groups (aryloxycarbonyloxy groups having from 7 to 12, preferably from 7 to 10 carbon atoms, such as a phenoxycarbonyloxy group and a p-methoxyphenoxycarbonyloxy group), and dialkylphosphinyloxy groups (phosphinyloxy groups having from 2 to 12, preferably from 2 to 6 carbon atoms, such as a dimethylphosphinyloxy group and a dibutylphosphinyloxy group).

Examples of the amino group having a substituent include:

alkylamino groups (alkylamino groups having from 1 to 20, preferably from 1 to 12 carbon atoms, such as a methylamino group, a dimethylamino group, a cyclohexylmethylamino group, and a 1-pyrrolidyl group), arylamino groups (arylamino groups having from 6 to 16, preferably from 6 to 12 carbon atoms, such as an anilino group, an N-methylanilino group, and a diphenylamino group), heterocyclic amino groups (heterocyclic amino groups having from 1 to 12, preferably from 2 to 6 carbon atoms, such as a 2-pyridylamino group, a pyrazol-4-ylamino group, a benzimidazol-2-ylamino group, a benzothiazol-2-ylamino group, a benzoxazol-2-ylamino group, a 2-oxazolylamino group, a 1,2,4-triazol-3-ylamino group, a 1,2,4-thiadiazol-2-ylamino group, a 1,3,4-thiadiazol-2-ylamino group, a 1,2,4-oxadiazol-2-ylamino group, and a 1,3,4-oxadiazol-2-ylamino group), acylamino groups (alkylcarbonylamino groups having from 1 to 10, preferably from 1 to 6 carbon atoms, arylcarbonylamino groups having from 6 to 18, preferably from 6 to 12 carbon atoms, and heterocyclic carbonylamino groups having from 2 to 12, preferably from 2 to 6 carbon atoms, such as a formylamino group, an acetylamino group, an ethylcarbonylamino group, a pivaloylamino group, a benzoylamino group, and a 4-pyridylcarbonylamino group), ureido groups (aminocarbonylamino groups having from 1 to 12, preferably from 1 to 8 carbon atoms, such as a carbamoylamino group, an N,N-dimethylaminocarbonylamino group, an N,N-diethylaminocarbonylamino group, and a morpholin-4-ylcarbonylamino group), alkoxycarbonylamino groups (alkoxycarbonylamino groups having from 2 to 10, preferably from 2 to 6 carbon atoms, such as a methoxycarbonylamino group, an ethoxycarbonylamino group, and a t-butoxycarbonylamino group), aryloxycarbonylamino groups (aryloxycarbonylamino groups having from 7 to 12, preferably from 7 to 9 carbon atoms, such as a phenoxycarbonylamino group), heterocyclic oxycarbonylamino groups (heterocyclic oxycarbonylamino groups having from 1 to 12, preferably from 2 to 6 carbon atoms, such as a 2-pyridyloxycarbonylamino group), sulfamoylamino groups (sulfamoylamino groups having from 0 to 10, preferably from 0 to 6 carbon atoms, such as a sulfamoylamino group and an N,N-dimethylaminosulfonylamino group), alkylsulfonylamino groups (alkylsulfonylamino groups having from 1 to 10, preferably from 1 to 6 carbon atoms, such as a methylsulfonylamino group, an ethylsulfonylamino group, and an n-butylsulfonylamino group), arylsulfonylamino groups (arylsulfonylamino groups having from 6 to 12, preferably from 6 to 8 carbon atoms, such as a phenylsulfonylamino group), and phosphinylamino groups (phosphinylamino groups having from 2 to 12, preferably from 2 to 6 carbon atoms, such as a dimethoxyphosphinylamino group and a dimethylaminophosphinylamino group).

Examples of the mercapto group having a substituent include:

alkylthio groups (alkylthio groups having from 1 to 10, preferably from 1 to 6 carbon atoms, such as a methylthio group, an ethylthio group, and a butylthio group), arylthio groups (arylthio groups having from 6 to 12, preferably from 6 to 8 carbon atoms, such as a phenylthio group), and heterocyclic thio groups (heterocyclic thio groups having from 1 to 10, preferably from 1 to 6 carbon atoms, such as a 2-benzothiazolylthio group, and a 1-phenyltetrazol-5-ylthio group).

Examples of the carbamoyl group having a substituent include:

alkylcarbamoyl groups (carbamoyl groups having from 1 to 12, preferably from 1 to 8 carbon atoms, such as a methylcarbamoyl group, a dimethylcarbamoyl group, a diethylcarbamoyl group, and a 1-pyrrolidylcarbamoyl group), and sulfamoylcarbamoyl groups (sulfamoylcarbamoyl groups having from 1 to 12, preferably from 1 to 8 carbon atoms, such as an N-(sulfamoyl)carbamoyl group and an N—(N',N'-dimethylsulfamoyl)carbamoyl group).

Examples of the sulfamoyl group having a substituent include:

alkylsulfamoyl groups (alkylsulfamoyl groups having from 1 to 12, preferably from 1 to 6 carbon atoms, such as an ethylsulfamoyl group, a dimethylsulfamoyl group, a dibutylsulfamoyl group, an ethylmethylsulfamoyl group, a diethylsulfamoyl group, and an N-cyclohexyl-N-methylsulfamoyl group), arylsulfamoyl groups (arylsulfamoyl groups having from 6 to 12, preferably from 6 to 8 carbon atoms, such as a phenylsulfamoyl group), and carbamoylsulfamoyl groups (carbamoylsulfamoyl groups having from 1 to 12, preferably from 1 to 6 carbon atoms, such as an N-(carbamoyl)sulfamoyl group).

Examples of the phosphoryl group having a substituent include:

alkylphosphoryl groups (alkylphosphoryl groups having from 1 to 12, preferably from 1 to 6 carbon atoms, such as a methylphosphoryl group and an ethylphosphoryl group).

Examples of the substituent having a substituent, the latter substituent having a substituent further, include:

alkoxyalkyl groups (linear, branched, or cyclic alkoxyalkyl groups having from 1 to 32, preferably from 1 to 12 carbon atoms, such as a methoxymethyl group, a methoxyethyl group, an ethoxyethyl group, and a cyclohexyloxypropyl group), alkoxyaryl groups (alkoxyaryl groups having from 7 to 18, preferably from 7 to 12 carbon atoms, such as a p-methoxyphenyl group and a 2,4-dimethoxyphenyl group), alkoxycarbonylalkyl groups (alkoxycarbonylalkyl groups having from 2 to 15, preferably from 2 to 6 carbon atoms, such as a methoxycarbonylethyl group and a 3-ethoxycarbonylpropyl group), alkylaminoalkyl groups (alkylaminoalkyl groups having from 2 to 15, preferably from 2 to 6 carbon atoms, such as an N-methylaminomethyl group and a dimethylaminoethyl group), alkylthioalkyl groups (alkylthioalkyl groups having from 2 to 15, preferably from 2 to 6 carbon atoms, such as a methylthiomethyl group, a methylthioethyl group, and an ethylthioethyl group), haloalkoxyaryl groups (haloalkoxyaryl groups having from 7 to 18, preferably from 7 to 12 carbon atoms, such as a 2-chloro-4-methoxyphenyl group and a 2,5-dichloro-4-methoxyphenyl group), alkoxycarbonyloxy groups (alkoxycarbonyloxy groups having from 2 to 15, preferably from 2 to 6 carbon atoms, such as a methoxycarbonyloxy group and an ethoxycarbonyloxy group), aryloxycarbonyloxy groups (aryloxycarbonyloxy groups having from 7 to 18, preferably from 7 to 12 carbon atoms, such as a phenoxycarbonyloxy group), alkoxycarbonylamino groups (alkoxycarbonylamino groups having from 2 to 10, preferably from 2 to 6 carbon atoms, such as a methoxycarbonylamino group, an ethoxycarbonylamino group, a t-butoxycarbonylamino group and an isobutyloxycarbonylamino group), and hydroxyalkylthio groups (hydroxyalkylthio groups having from 1 to 15, preferably from 1 to 6 carbon atoms, such as a hydroxyethylthio group and a 2-hydroxypropylthio group).

$R_3$ represents a hydroxy group, an alkylsulfonylamino group, an arylsulfonylamino group or —CH($R_4$)($R_5$), preferably an alkylsulfonylamino group or —CH($R_4$)($R_5$). The preferred number of carbon atoms and specific examples of these groups are similar to those described in the description of the substituents represented by $R_6$ to $R_8$.

$R_4$ and $R_5$ each represents an electron withdrawing group having a Hammett substituent constant σ value of 0.2 or greater and less than 1.4. The Hammett empirical rule was advocated by L. P. Hammett in 1935 in order to quantitatively discuss the influence of a substituent on the reaction or equilibrium of a benzene derivative and its validity is now recognized widely. The substituent constants determined by the Hammett rule are $σ_p$ and $σ_m$ values. These values are found generally in many books and described in detail, for example, in *Lange's Handbook of Chemistry*, 12 ed., 1979, ed. J. A. Dean (published by McGraw-Hill), *Journal of Japanese Chemistry*, Extra Number, 122, 96-103 (1979) (published by Nankodo), and *Chemical Review*, 91, 165-195 (1991). It is needless to say that $R_4$ and $R_5$ are not limited to substituents described as a substituent having a σ value of 0.2 or greater and less than 1.4 and they embrace substituents whose σ value is unknown in literatures but is within the range when measured based on the Hammette rule. Specific examples of the electron withdrawing group having a σ value of 0.2 or greater and less than 1.4 include a chlorine atom, acyl groups, alkyloxycarbonyl groups, aryloxycarbonyl groups, a carbamoyl group, a cyano group, a nitro group, alkylsulfonyl groups, arylsulfonyl groups, and a sulfamoyl group. $R_4$ and $R_5$ may be the same or different and they are preferably the same. They are each preferably a carbamoyl group, an alkyloxycarbonyl group, an aryloxycarbonyl group, or a cyano group, more preferably a carbamoyl group, an alkyloxycarbonyl group, or a cyano group. The preferred number of carbon atoms and specific examples of these groups are similar to those described in the description of the substituents represented by $R_6$ to $R_8$.

$R_6$ is preferably an alkyl group, an acyl group, or an aryl group, more preferably an alkyl group or an aryl group, even more preferably an alkyl group having from 1 to 6 carbon atoms. Specific examples include a methyl group, an ethyl group, an n-propyl group, an isopropyl group, and a t-butyl group.

$R_7$ is preferably an alkyl group, an acylamino group, an aryl group, an amino group, an alkyloxycarbonylamino group, or an alkylaminocarbonyloxy group, more preferably an alkyl group or an aryl group, even more preferably an alkyl group having from 1 to 4 carbon atoms. Specific examples include a methyl group, an ethyl group, and an isopropyl group.

$R_8$ is preferably an alkyl group, an aryl group, an alkylthio group, an arylthio group, or an alkyloxy group, more preferably an alkyl group or an alkylthio group, even more preferably an alkyl group having from 1 to 3 carbon atoms. Specific examples include a methyl group and an ethyl group.

Preferred examples of the combination of X, Y and Z include a combination of X representing a carbon atom, and Y and Z each representing a nitrogen atom and a combination of X and Z each representing a nitrogen atom and Y representing a carbon atom. The following Het-1 to Het-13 are examples of a group composed of a heterocycle in which X, Y, and Z are combined and one or two $R_8$(s). Of these, Het-4 to Het-13 are examples in which two $R_8$ are coupled to form an aromatic ring or a heterocyclic ring. In the following formulas, $R_8$ has the same meaning as described above and $R_{9a}$ to $R_{9h}$ represent a substituent. Examples of the substituent of $R_{9a}$ to $R_{9h}$ include those described above as $R_6$ to $R_8$. Two or more of the groups adjacent to each other may be coupled together to form a saturated or unsaturated, 5-membered or 6-membered structure.

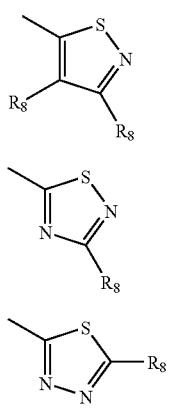

Het-1

Het-2

Het-3

-continued

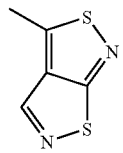

Het-4

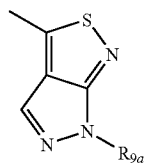

Het-5

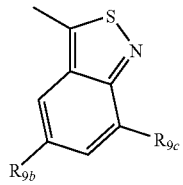

Het-6

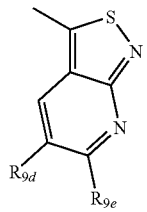

Het-7

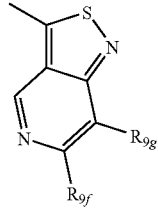

Het-8

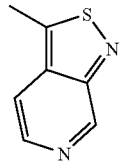

Het-9

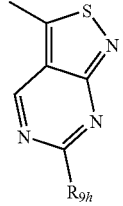

Het-10

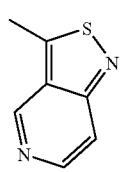

Het-11

-continued
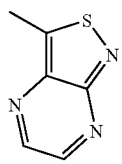
Het-12
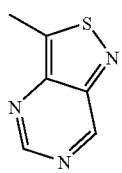
Het-13
The following are specific examples of the dissociative azo dye represented by the formula (5), but the dye is not limited to the following examples.
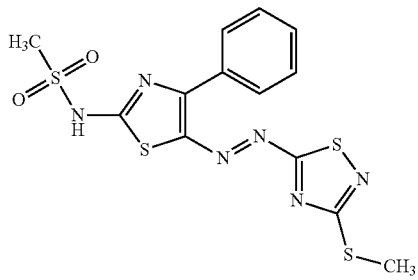
D5-1
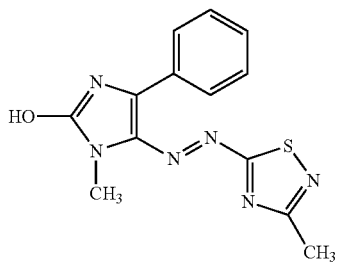
D5-2
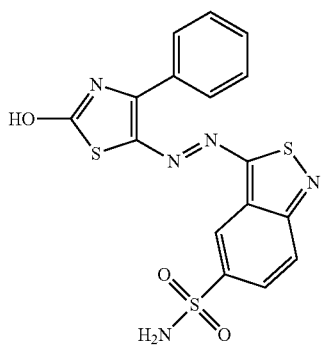
D5-3
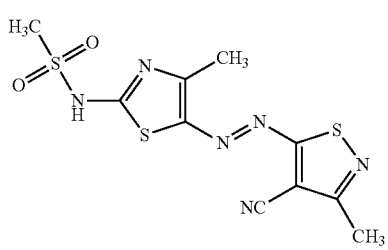
D5-4
-continued
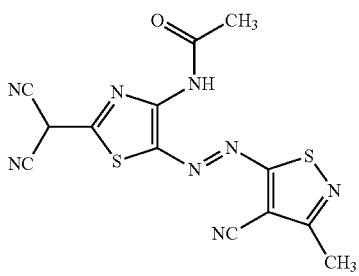
D5-5
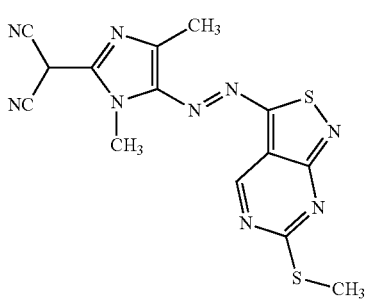
D5-6
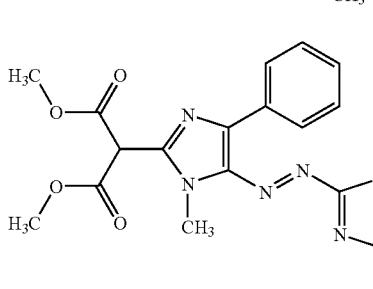
D5-7
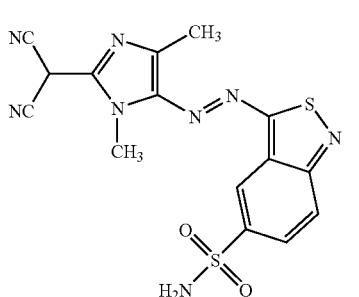
D5-8
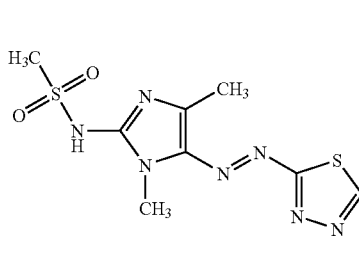
D5-9
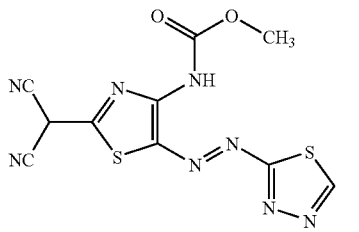
D5-10

D5-11
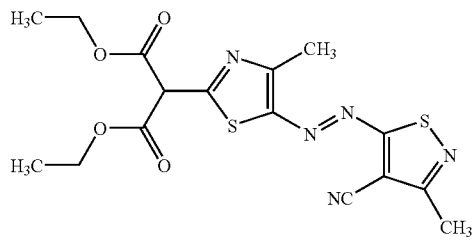
D5-12
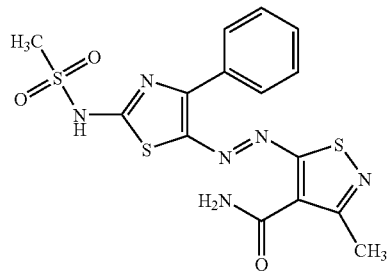
D5-13
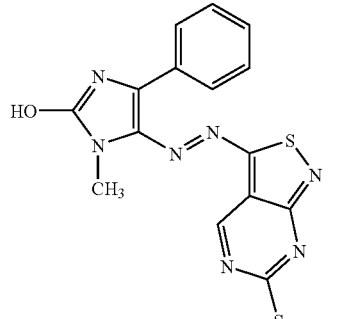
D5-14
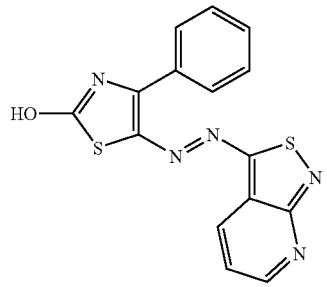
D5-15
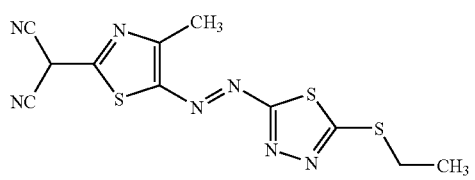
D5-16
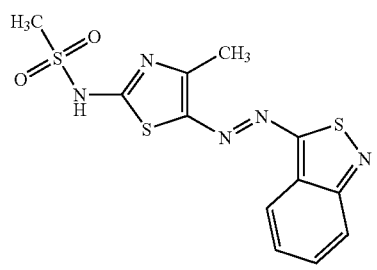
D5-17
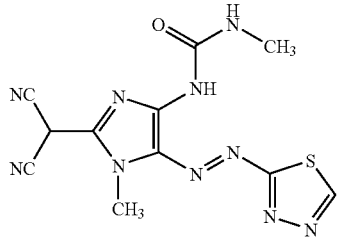
D5-18
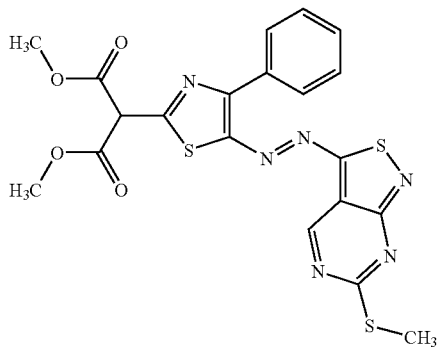
D5-19
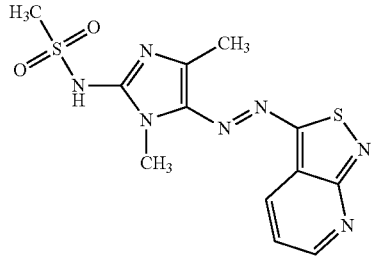
D5-20
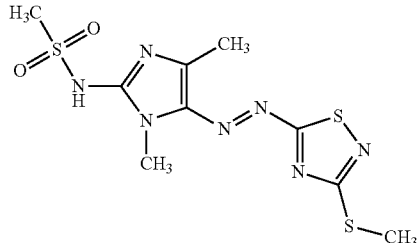
D5-21
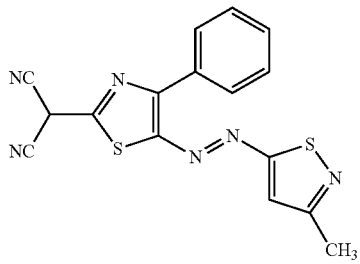

-continued

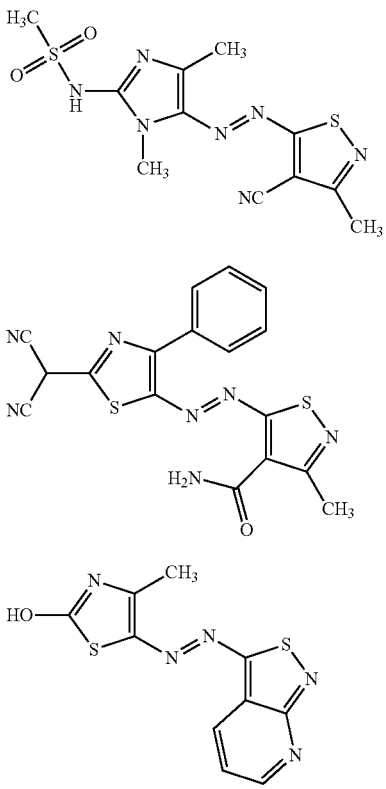

Preferred examples of the dissociative azo dye (5) include compounds having as $R_3$ an alkylsulfonylamino group, and as W a sulfur atom, b being 1.

The dissociative azo dyes (1) to (5) to be used for the hair dye composition of the present invention may be used either singly or in combination of two or more thereof. Its (their) content in the whole composition is preferably from 0.0001 to 25 mass %, more preferably from 0.001 to 20 mass %, even more preferably from 0.05 to 15 mass %, even more preferably from 0.1 to 10 mass %.

The dissociative azo dyes (1) to (5) to be used in the hair dye composition of the present invention have excellent storage stability within a wide pH range from 2 to 14 within which ordinary hair dyes are used. They can be used at a desired pH within the above-described range. From the standpoints of hair dyeing/bleaching effects and less skin irritation, the pH of the whole composition at the time of use (at the time of mixing) is preferably from 8 to 14 (25° C.), more preferably from pH 8 to 13. When the hair dye composition of the present invention is a multi-part type, the first part before mixing has preferably a pH of from 8 to 14 and the second part before mixing has preferably a pH of from 2 to 5. Examples of the pH regulator which can be added include, in addition to the alkali agents described below, inorganic acids such as hydrochloric acid and phosphoric acid, organic acids such as citric acid, glycolic acid, and lactic acid, hydrochlorides such as monoethanolamine hydrochloride, and phosphates such as monopotassium dihydrogen phosphate and disodium monohydrogen phosphate.

Oxidizing Agent

Since each of the dissociative azo dyes (1) to (5) is remarkably stable against an oxidizing agent, it can be applied to the hair after mixed with an oxidizing agent. In other words, the hair dye composition of the present invention can be provided as a two part type composed of a first part containing the dissociative azo dye (1) to (5) and a second part containing an oxidizing agent. In this case, dyeing and bleaching occur simultaneously so that more vivid color can be produced.

Examples of the oxidizing agent include hydrogen peroxide, persulfates such as ammonium persulfate, potassium persulfate, and sodium persulfate, perborates such as sodium perborate, percarbonates such as sodium percarbonate, and bromates such as sodium bromate and potassium bromate. Of these, hydrogen peroxide is preferred from the viewpoint of hair bleaching property and stability and effectiveness as the oxidizing agent itself. Another oxidizing agent may be used as an oxidizing aid in combination with hydrogen peroxide. Use of hydrogen peroxide and a persulfate in combination is preferred.

When the oxidizing agents are used, they may be used either singly or in combination of two or more thereof. Its (their) content in the whole composition is preferably from 0.5 to 30 mass %, more preferably from 1 to 20 mass %. When hydrogen peroxide and a persulfate are used in combination, it is preferred that the content of hydrogen peroxide in the whole composition is from 0.5 to 10 mass %, the content of a persulfate in the whole composition is from 0.5 to 25 mass %, and the total content of them is from 1 to 30 mass %.

When the hair dye composition of the present invention is provided as a two-part type, the first part containing one or more of the dissociative azo dyes (1) to (5) and the second part containing the oxidizing agent are mixed preferably at a volume ratio of from 2:1 to 1:3.

Other Dyes

The hair dye composition of the present invention can have various color tones by incorporating therein another direct dye or oxidation dye.

As another direct dye, known direct dyes such as acid dyes, basic dyes, nitro dyes, disperse dyes, and cationic dyes can be used. Examples of the direct dye include Blue No. 1, Violet No. 401, Black No. 401, Orange No. 205, Red No. 227, Red No. 106, Yellow No. 203, Yellow No. 403(1), Acid Orange 3, 2-nitro-p-phenylenediamine, 2-amino-6-chloro-4-nitrophenol, 3-nitro-p-hydroxyethylaminophenol, 4-nitro-o-phenylenediamine, 4-amino-3-nitrophenol, 4-hydroxypropylamino-3-nitrophenol, HC Blue 2, HC Orange 1, HC Red 1, HC Yellow 2, HC Yellow 4, HC Yellow 5, HC Red 3, N,N-bis (2-hydroxyethyl)-2-nitro-p-phenylenediamine, Disperse Violet 1, Disperse Blue 1, Disperse Black 9, Basic Blue 99, Basic Brown 16, Basic Brown 17, Basic Red 76, Basic Yellow 76, Basic Yellow 57, Basic Orange 31, Basic Red 51, and methine type cationic dyes having a cyanine structure represented by the following formulas:

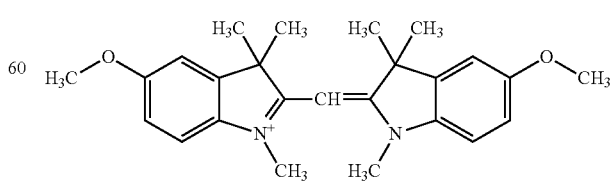

Yellow dye

-continued

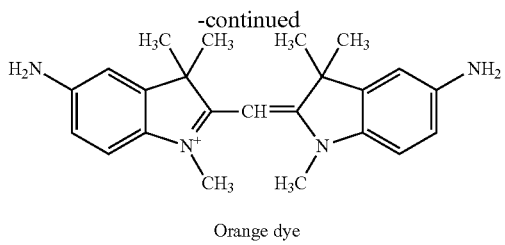

Orange dye

Additional examples include direct dyes described in JP-A-2002-275040, JP-A-2003-107222, JP-A-2003-107223, JP-A-2003-113055, JP-A-2003-342139, JP-A-2004-107343, JP-A-2004-155746, and JP-A-2006-182653.

When another direct dye is used in combination, the total content of one or more of the dissociative azo dye (1) to (5) and another direct dye in the whole composition is preferably from 0.0001 to 20 mass %, more preferably from 0.001 to 20 mass %, even more preferably from 0.05 to 15 mass %, even more preferably from 0.1 to 10 mass %.

In the hair dye composition of the present invention, an oxidation dye may be used in combination with the dissociative azo dyes (1) to (5). Such combined use achieves very vivid and strong dyeing which is not available by the single use of an oxidation dye. As the oxidation dye, known precursors and known couplers ordinarily employed for oxidation hair dyes are used.

Examples of the precursor include paraphenylenediamine, toluene-2,5-diamine, orthochloroparaphenylenediamine, N-phenylparaphenylenediamine, N,N-bis(hydroxyethyl)paraphenylenediamine, 3-methyl-4-aminophenol, 2-hydroxyethylparaphenylenediamine, paraminophenol, paramethylaminophenol, 4-aminometacresol, and orthoaminophenol, and salts thereof.

Examples of the coupler include resorcin, 2-methylresorcin, 1-naphthol, 1,5-dihydroxynaphthalene, 5-aminoorthocresol, metaphenylenediamine, metaminophenol, 2,4-diaminophenoxyethanol, 2,6-diaminopyridine, 2-methyl-5-hydroxyethylaminophenol, and 2-amino-3-hydroxypyridine, and salts thereof.

Two or more of these precursors or these couplers may be used in combination. A total content of them in the whole composition is preferably from 0.0005 to 20 mass %, more preferably from 0.001 to 15 mass %, even more preferably from 0.5 to 10 mass %.

The hair dye composition of the present invention may further contain an automatic oxidation dye typified by an indole or indoline.

The total content of one or more of the dissociative azo dyes (1) to (5), another direct dye, an oxidation dye, and an automatic oxidation dye in the whole composition is preferably from 0.001 to 25 mass %, more preferably from 0.01 to 20 mass %, even more preferably from 0.1 to 15 mass %, even more preferably from 0.5 to 10 mass %.

Other Components

When the hair dye composition of the present invention is a two part type or a three part type, the first part contains an alkali agent. Examples of the alkali agent include ammonia and salts thereof; alkanolamines such as monoethanolamine, isopropanolamine, 2-amino-2-methylpropanol, and 2-aminobutanol, and salts thereof; alkanediamines such as 1,3-propanediamine, and salts thereof; and carbonates such as guanidine carbonate, sodium carbonate, potassium carbonate, sodium bicarbonate and potassium bicarbonate. Of the alkali agents, ammonia and alkanolamines, and salts thereof are preferred. As the ammonium salt, ammonium carbonate and ammonium hydrogen carbonate are preferred, while as the alkanolamine and salts thereof, monoethanolamine and salts thereof are preferred.

Of the above-described alkali agents, ammonia and alkanolamines, and salts thereof are preferred. As the ammonium salt, ammonium carbonate and ammonium hydrogen carbonate are preferred, while as the alkanolamine and salts thereof, monoethanolamine and salts thereof are preferred. The content of the alkali agent preferably falls within the following range. The sum of the content (X), in terms of ammonia, of the ammonia and salts thereof and the content (Y), in terms of monoethanolamine, of the monoethanolamine and salts thereof is preferably from 0.05 to 15 mass %, more preferably from 0.1 to 10 mass %, even more preferably from 0.2 to 5 mass % in the whole composition in order to produce sufficient hair dyeing/bleaching effects and reduce the hair damage, scalp irritation and odor stimulus. A X:Y mass ratio is preferably from 0.01:1 to 2:1, more preferably from 0.02:1 to 1:1, even more preferably from 0.05:1 to 0.5:1.

The hair dye composition of the present invention may contain a conditioning component which can be suitably applied to the hair. The conditioning component is usually a polymer or an oil, such component may be soluble or dispersible in hair dye compositions, and it attaches to the hair during rinsing or when diluted with water or a shampoo.

When the conditioning component is used, its amount is from 0.01 to 30 mass %, preferably from 0.05 to 20 mass %, more preferably from 0.1 to 10 mass in the whole composition.

The conditioning component suited for use in the hair dye composition of the present invention is usually a conditioning agent characterized as a cationic polymer, a silicone, or an organic conditioning oil (such as a hydrocarbon oil, a polyolefin, or a fatty acid ester), or a combination thereof. In addition, a conditioning agent which forms dispersion particles in an aqueous surfactant can also be used as the conditioning component.

The term "cationic polymer" means a polymer having a cationic group or a group which can be ionized into a cationic group. It embraces an amphoteric polymer which will be cationic as an entirety. Described specifically, examples of the cationic polymer include polymers in the form of an aqueous solution having, on the side chain of their polymer chain, an amino or ammonium group, or having a diallyl quaternary ammonium salt as a constituent unit, such as cationic cellulose derivatives, cationic starches, cationic guar gum derivatives, polymers or copolymers of a diallyl quaternary ammonium salt, and quaternized polyvinylpyrrolidone derivatives. Of these cationic polymers, polymers containing a diallyl quaternary ammonium salt as a constituent unit, quaternized polyvinylpyrrolidone derivatives, and cationic cellulose derivatives are preferred from the viewpoint of their effect on softness, smoothness and easy finger combing during shampooing, and manageability of hair and moisture retention during drying, and stability of the composition.

Specific examples of the polymer or copolymer of a diallyl quaternary ammonium salt include dimethyldiallyl ammonium chloride polymers ("polyquaternium-6, such as "Merquat 100", product of Nalco), dimethyldiallyl ammonium chloride/acrylic acid copolymers (polyquaternium-22 such as "Merquat 280" and "Merquat 295", each product of Nalco), and dimethyldiallyl ammonium chloride/acrylic acid amide copolymers (polyquaternium-7 such as "Merquat 550", product of Nalco).

Specific examples of the quaternized polyvinyl pyrrolidone derivatives include quaternary ammonium salts (polyquaternium-11, such as "Gafquat 734", "Gafquat 755" and "Gafquat 755N" (each, product of ISP, JAPAN)) available from a copolymer of vinylpyrrolidone (VP) and dimethylaminoethyl methacrylate and diethyl sulfate.

Specific examples of the cationic cellulose derivatives include polymers of a quaternary ammonium salt (polyquaternium-10 such as "Leogard G" and "Leogard GP" (each, product of Lion), "Polymer JR-125", "Polymer JR-400", "Polymer JR-30M", "Polymer LR-400" and "Polymer LR-30M" (each, product of Amerchol)) available by adding glycidyl trimethylammonium chloride to hydroxyethyl cellulose and hydroxyethylcellulose/dimethyl diallylammonium chloride copolymers (polyquaternium-4 such as "Celquat H-100" and "Celquat L-200" (each, product of National Starch and Chemical).

Two or more of these cationic polymers may be used in combination. When the content of the cationic polymer is higher, the effect brought by it is greater. An excessively high content may however cause poor stability and reduction in viscosity of the composition or viscosity during mixing thereof. In view of them and also improvement in hair feel, the content of the cationic polymer in the whole composition is preferably from 0.001 to 20 mass %, more preferably from 0.01 to 10 mass %, even more preferably from 0.05 to 5 mass %.

The hair dye composition of the present invention contains preferably a polysilicone in order to impart excellent feeling upon use to the composition. Examples of the polysilicone include polyalkoxysilanes, modified silicones (such as amino-modified silicones, fluorine-modified silicones, alcohol-modified silicones, polyether-modified silicones, epoxy-modified silicones, and alkyl-modified silicones). Of these, polyalkoxysilanes, polyether-modified silicones, and amino-modified silicones are preferred.

As the polyalkoxysilanes, cyclic or noncyclic dimethylsiloxane polymers are usable. Examples include "SH200 Series", "BY22-019", "BY22-020", "BY11-026", "BY22-029", "BY22-034", "BY22-050A", "BY22-055", "BY22-060", "BY22-083", and "FZ-4188" (each, product of Dow Corning Toray), and "KF-9008" "KM-900 Series", "MK-15H", and "MK-88" (each, product of Shin-etsu Chemical).

As the polyether-modified silicones, silicones having a polyoxyalkylene group are usable. Examples of groups constituting the polyoxyalkylene group include an oxyethylene group and an oxypropylene group. Specific examples include "KF-6015", "KF-945A", "KF-6005", "KF-6009", "KF-6013", "KF-6019", "KF-6029", "KF-6017", "KF-6043", "KF-353A", "KF-354A", and "KF-355A (each, product of Shin-etsu Chemical), and "FZ-2404", "SS-2805", "FZ-2411", "FZ-2412", "SH3771M", "SH3772M", "SH3773M", "SH3775M", "SH3749", "SS-280X Series", "BY22-008M", "BY11-030", and "BY25-337" (each, product of Dow Corning Toray).

As the amino-modified silicones, silicones having an amino or ammonium group are usable. Examples include amino-modified silicone oils having terminal hydroxy groups, some or all of which have been blocked with a methyl or the like group, and amodimethicone having an unblocked terminal group. Preferred examples of the amino-modified silicones include those represented by the following formula (S):

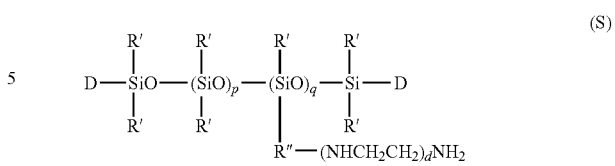

[wherein, R' represents a hydroxy group, a hydrogen atom, or $R^x$, $R^x$ represents a substituted or unsubstituted monovalent hydrocarbon group having from 1 to 20 carbon atoms, D represents $R^x$, a group —R"—(NHCH$_2$CH$_2$)$_d$NH$_2$, a group OR$^x$, or a hydroxy group, R" represents a divalent hydrocarbon group having from 1 to 8 carbon atoms, d stands for a number from 0 to 3, p and q are numbers, the sum of which is, in number average, 10 or greater and less than 20000, preferably 20 or greater and less than 3000, more preferably 30 or greater and less than 1000, even more preferably 40 or greater and less than 800].

Specific preferred examples of the commercially available amino-modified silicone include amino-modified silicone oils such as "SF8452C" and "SS-3551" (each, product of Dow Corning Toray) and "KF8004", "KF-867S", and "KF-8015" (each, product of Shin-etsu Chemical) and amodimethicone emulsions such as "SM8704C", "SM8904", "BY22-079", "FZ-4671", and "FZ-4672" (each, product of Dow Corning Toray).

The total content of these silicones in the hair dye composition of the present invention is preferably from 0.02 to 40 mass %, more preferably from 0.1 to 20 mass %, even more preferably from 0.2 to 15 mass % in the whole composition from the standpoint of producing sufficient effects and preventing sticky feel.

When the hair dye composition of the present invention contains the silicone and the cationic polymer, a cationic polymer (active amount):silicone mass ratio in the whole composition is preferably from 100:1 to 1:50, more preferably from 50:1 to 1:10.

The hair dye composition of the present invention preferably contains a higher alcohol in at least one of the first part, the second part, and the third part from the viewpoint of improving the feel and stability. Addition of the higher alcohol is effective for preventing the separation of the hair dye composition by forming a structure with a surfactant and at the same time improving the feel during rinsing.

As the higher alcohol, those having from 8 to 22 carbon atoms are preferred, with those having from 16 to 22 carbon atoms being more preferred. Specific examples include cetyl alcohol, stearyl alcohol, and behenyl alcohol, and mixtures thereof.

Two or more of these higher alcohols may be used in combination. Its (their) content in the whole composition is preferably from 0.01 to 20 mass %, more preferably from 0.1 to 10 mass %.

The hair dye composition of the present invention may contain a surfactant. As the surfactant, any of cationic surfactants, nonionic surfactants, amphoteric surfactants and anionic surfactants can be used.

As the cationic surfactants, mono(long-chain alkyl) quaternary ammonium salts are preferred. Specific examples include cetyltrimethylammonium chloride, stearyltrimethylammonium chloride, arachyltrimethylammonium chloride, and behenyltrimethylammonium chloride. Of these, stearyltrimethylammonium chloride and behenyltrimethylammonium chloride are preferred.

Examples of the nonionic surfactants include polyoxyalkylene alkyl ethers, polyoxyalkylene alkenyl ethers, higher fatty acid sucrose esters, polyglycerin fatty acid esters, higher fatty acid mono- or di-ethanolamides, polyoxyethylene hydrogenated castor oils, polyoxyethylene sorbitan fatty acid esters, polyoxyethylene sorbitol fatty acid esters, alkyl saccharide surfactants, alkylamine oxides, and alkylamidoamine oxides. Of these, polyoxyalkylene alkyl ethers, and polyoxyethylene hydrogenated castor oils are preferred, with polyoxyethylene alkyl ethers being more preferred.

Examples of the amphoteric surfactants include imidazoline, carbobetaine, amidobetaine, sulfobetaine, hydroxysulfobetaine, and amidosulfobetaine.

Examples of the anionic surfactant include alkylbenzene sulfonates, alkyl or alkenyl ether sulfates, alkyl or alkenyl sulfates, olefin sulfonates, alkane sulfonates, saturated or unsaturated fatty acid salts, alkyl or alkenyl ether carboxylates, α-sulfone fatty acid salts, N-acylamino acid surfactants, mono- or di-phosphate surfactants and sulfosuccinates. Examples of the alkyl ether sulfates include polyoxyethylene alkyl ether sulfates. Examples of the counter ions of the anionic residue of the above-described surfactants include alkali metal ions such as sodium ion and potassium ion; alkaline earth metal ions such as calcium ion and magnesium ion, ammonium ions, alkanolamines having 1 to 3 alkanol groups with 2 or 3 carbon atoms (such as monoethanolamine, diethanolamine, triethanolamine and triisopropanolamine).

These surfactants may be used either singly or in combination of two or more. Its (their) content in the whole composition is not particularly limited, but it is preferably from 0.05 to 20 mass %, more preferably from 0.1 to 18 mass %, even more preferably from 0.5 to 15 mass %.

For the hair dye composition of the present invention, water and, if necessary, an organic solvent are used as a medium. Examples of the organic solvent include lower aliphatic alcohols such as ethanol, propanol and isopropanol; aromatic alcohols such as benzyl alcohol and benzyloxyethanol; polyols such as propylene glycol, 1,3-butanediol, diethylene glycol and glycerin; cellosolves such as ethyl cellosolve and butyl cellosolve; and carbitols such as ethyl carbitol and butyl carbitol.

Although no particular limitation is imposed on the content of the organic solvent, it is preferably from 0.05 to 20 mass %, more preferably from 0.1 to 15 mass %, even more preferably from 0.5 to 10 mass % in the whole composition.

The hair dye composition of the present invention may contain, in addition to the above-described components, another component used ordinarily as cosmetic raw materials. Examples of such an optional component include hydrocarbons, plant or animal oils or fats, higher fatty acids, natural or synthetic polymers, ethers, protein derivatives, hydrolyzed proteins, amino acids, preservatives, chelating agents, stabilizers, antioxidants, plant extracts, crude drug extracts, vitamin preparations, fragrances, and ultraviolet absorbers.

The hair dye composition of the present invention is provided preferably as a one-part type; a two-part type composed of a first part containing one or more of the dissociative azo dyes (1) to (5) and an alkali agent and a second part containing an oxidizing agent such as hydrogen peroxide; or a three-part type containing, in addition to the second-part type, a powdery oxidizing agent made of ground persulfate (ammonium persulfate, potassium persulfate, sodium persulfate or the like) as a third part for improving bleaching capacity.

The one-part type can be provided, for example, as a liquid, an emulsion, a cream, a gel, a paste, or a mousse. It can also be provided as an aerosol. In the case of the two-part type (or three-part type), the first part and the second part can be provided, for example, as a liquid, an emulsion, a cream, a gel, a paste or a mousse. They can also be provided as an aerosol. It is preferred that a mixture of the first part and the second part (and also the third part in the three-part type) has a viscosity enough to prevent sagging when it is applied to the hair. In any of the one-part type, the two-part type, and the three-part type, the hair dye composition of the present invention has a viscosity of preferably from 2000 to 100000 mPa·s as measured at 25° C. by a B type rotational viscometer equipped with a helical stand ("B8R viscometer", product of Tokimec). The viscosity is a value determined after rotation at 10 rpm for one minute by using a rotor T-C.

It is also possible to use a known two-part oxidation hair dye or three-part oxidation hair dye in combination with a solution containing one or more of the dissociative azo dyes (1) to (5) as a booster solution for changing the color tone of the oxidation hair dye. Described specifically, a booster solution containing one or more of the dissociative azo dyes (1) to (5) is used in combination with a known two-part oxidation hair dye composed of a first part containing an alkali agent (which may contain any oxidation dye intermediates or direct dyes) and a second part containing an oxidizing agent, or with a known three-part oxidation hair dye having, in addition to such first part and second part, a third part containing an oxidizing aid. It is also possible to use, for example, the two-part oxidation hair dye or the three-part oxidation hair dye as described above before or during use of the one-part hair dye composition containing one or more of the dissociative azo dyes (1) to (5).

Hair Dyeing Method

The hair may be dyed with the composition of the present invention, for example, in the following manner. After mixing the first part and the second part (also the third part if the composition is a three-part type) are mixed just before use, the resulting mixture is applied to the hair. After being allowed to stand for a predetermined time within one hour, the hair may be rinsed and dried. The composition is applied to the hair at from 15 to 45° C. for preferably from 3 to 50 minutes, more preferably from 5 to 40 minutes, even more preferably from 10 to 30 minutes. In this case, by washing off the hair dye lightly with water, shampooing the hair with a shampoo containing an anionic surfactant, and then washing the hair with water, the cationic polymer is washed away sufficiently, while an adequate amount of the silicone still remains on the hair and it produces good conditioning effects. As the shampoo, a typical aqueous shampoo containing from 50 to 20 mass % of an anionic surfactant such as sodium laureth-1 sulfate, sodium laureth-2 sulfate or sodium laureth-3 sulfate is suited.

The following examples further describe and demonstrate embodiments of the present invention. The examples are given solely for the purpose of illustration and are not to be construed as limitations of the present invention.

EXAMPLES

Synthesis Example 1-1

A dissociative azo dye D1-31 is synthesized in accordance with the following reaction scheme:

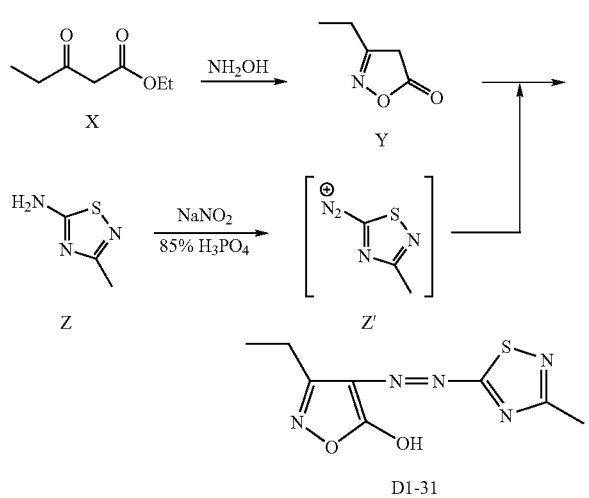

Compound Z (6.4 g, 0.056 mol) is dissolved in 54 g of 850 phosphoric acid. While stirring, 4.2 g of sodium nitrite is added in portions in the form of a powder to the resulting solution at 0° C. or less over about one hour. After completion of the addition, stirring is continued further for one hour at 0° C. While stirring, the reaction mixture is added to a solution of Compound Y in methanol (4 g/50 mL) at 0° C. or less. After stirring is continued for one hour without changing the temperature, 100 mL of water is poured into the reaction mixture. Crystals thus precipitated are collected by filtration and then washed with water. The crystals are air dried overnight at room temperature, followed by recrystallization from methanol/water to yield 3 g of Isoxazolone dye D1-31. Yield: 38%.

The dye had a melting point of from 116 to 117° C. and an absorption maximum λmax in DMF at 443 nm (ε: 23,000) and developed a good hue.

Fastness Test

The hair dye composition having the following formulation is prepared using Dissociative azo dye D1-31 and is evaluated for its fastness.

| | |
|---|---|
| Dye D1-31 | 0.2 g |
| Benzyl alcohol | 5.0 g |
| Sodium lauryl sulfate | 0.01 g |
| Ammonium hydroxide (25 mass %) | 5.0 g |
| Hydrogen peroxide (50 mass %) | 6.0 g |
| Water | To provide a total of 100 g | pH 10.0

The hair dye composition is applied at 50° C. for 15 minutes to white goat hair damaged (by permanent waving). After completion of the dyeing procedure, the tress is washed and dried and the color of it is observed. Each tress is then subjected to a washing and fading protocol and fastness to shampooing is analyzed.

The washing protocol comprises applying 0.1 g of a shampoo per gram of hair, rubbing the shampoo into the hair over 30 seconds, and washing the tress with water of 40° C. for 30 seconds. A series of this procedure is repeated 20 times.

As a result, it has been observed that the hair dye composition had good fastness to light or heat without undergoing concentration reduction and color change.

Synthesis Examples 1-2 to 1-9

Dissociative azo dyes synthesized in a similar manner to that employed in Synthesis Example 1-1 are shown in Table 1.

TABLE 1

| Synthesis Examples | | λmax (nm) | ε | Yield (%) | Color of crystals |
|---|---|---|---|---|---|
| Synthesis Example 1-1 | D1-31 | 443 | 23000 | 38 | Yellow |
| Synthesis Example 1-2 | D1-35 | 443 | 24300 | 47 | Yellow |
| Synthesis Example 1-3 | D1-46 | 444 | 21800 | 38 | Yellow |
| Synthesis Example 1-4 | D1-34 | 422 | 21800 | 51 | Yellow |
| Synthesis Example 1-5 | D1-47 | 442 | 22000 | 41 | Yellow |
| Synthesis Example 1-6 | D1-31 | 443 | 23000 | 38 | Yellow |
| Synthesis Example 1-7 | D1-48 | 440 | 22300 | 33 | Yellow |
| Synthesis Example 1-8 | D1-32 | 449 | 24800 | 53 | Yellow |
| Synthesis Example 1-9 | D1-49 | 449 | 26300 | 42 | Yellow |

A fastness test is also made on the dissociative azo dyes in Table 1 in a similar manner to that employed for Azo dye D1-31 of Synthesis Example 1-1. As a result, it has been observed that the hair dye compositions had good fastness to light or heat without undergoing concentration reduction and color change.

Examples 1-1 to 1-7

The first part of each of the two-part hair dyes shown in Table 2 and 6 mass % aqueous hydrogen peroxide (second part) are prepared. The first part, the second part, and purified water are mixed at a 4:7:1 mass ratio to yield a hair dye composition. To 1 g of goat hair, 1 g of the hair dye composition is applied at 30° C. After being allowed to stand for 30 minutes, the hair is washed with water and a shampoo, and then dried.

After hair dyeing, the chromaticities of the tress are measured. The chromaticities of the tress before and after coloring treatment are measured using a colorimeter "CR-400" manufactured by Konica Minolta and expressed by a L*a*b* color system. A chromaticity change ΔE* is calculated by the following known equation. The results are also shown in Table 2.

$$\Delta E^* = \sqrt{(\Delta L^*)^2 + (\Delta a^*)^2 + (\Delta b^*)^2} \quad \text{[Equation 1]}$$

TABLE 2

| | Examples | | | | | | |
|---|---|---|---|---|---|---|---|
| (Mass %) | 1-1 | 1-2 | 1-3 | 1-4 | 1-5 | 1-6 | 1-7 |
| Dye | D1-31 | D1-32 | D1-34 | D1-46 | D1-47 | D1-48 | D1-49 |
| | 1.2 | 1.2 | 1.2 | 1.2 | 1.2 | 1.2 | 1.2 |
| Aqueous ammonia (28%) | | | | 9.0 | | | |
| Purified water | | | | Balance | | | |
| Total | 100.0 | 100.0 | 100.0 | 100.0 | 100.0 | 100.0 | 100.0 |
| ΔE* | 78.0 | 60.6 | 75.6 | 79.1 | 70.1 | 61.2 | 75.7 |

Examples 1-8 to 1-10

Foam-type one-part hair dyes shown in Table 3 are prepared. To 1 g of a tress made of human hair and containing 10% of gray hair, an equal amount of each of the hair dye compositions is applied. After being allowed to stand for 30 minutes, the tress is washed with water and a shampoo, and then dried.

TABLE 3

| (Mass %) | Example 1-8 | Example 1-9 | Example 1-10 |
| --- | --- | --- | --- |
| D1-35 | 0.3 | — | 0.1 |
| D1-46 | — | 0.3 | — |
| D1-49 | — | — | 0.2 |
| Basic red 76 | 0.3 | — | 0.3 |
| Basic blue 99 | — | 0.2 | — |
| Ammonia (28%) | 8.0 | 8.0 | 8.0 |
| Isopropyl alcohol | 3.5 | 3.5 | 3.5 |
| Polyoxyethylene lauryl ether (23E.O) | 0.5 | 0.5 | 0.5 |
| Benzyl alcohol | — | — | 8.0 |
| Oleic acid | 7.5 | 7.5 | 7.5 |
| LPG (4.0 kg/cm$^2$) | 10.0 | 10.0 | 10.0 |
| Purified water | Balance | Balance | Balance |
| Total | 100.0 | 100.0 | 100.0 |

Examples 1-11 to 1-14

The first part of each of the cream-type two-part hair dyes shown in Table 4 and the common second part shown in Table 5 are prepared. The first part and the common second part are mixed at a 1:1 mass ratio to yield a hair dye composition. To 1 g of a tress made of human hair and containing 10% of gray hair, an equal amount of the hair dye composition is applied. After being allowed to stand for 30 minutes, the tress is washed with water and a shampoo, and then dried.

TABLE 4

| (Mass %) | Example 1-11 | Example 1-12 | Example 1-13 | Example 1-14 |
| --- | --- | --- | --- | --- |
| D1-32 | 0.5 | 0.3 | 0.1 | 0.1 |
| D1-34 | — | — | — | 0.2 |
| D1-35 | — | 0.2 | 0.3 | — |
| Toluene-2,5-diamine sulfate | — | 0.1 | 0.4 | — |
| Para-aminophenol | — | 0.1 | — | 0.1 |
| Meta-aminophenol | — | 0.2 | 0.2 | — |
| 5-Amino-ortho-cresol | — | — | 0.2 | 0.1 |
| Ammonia (28%) | 6.0 | 6.0 | 6.0 | 6.0 |
| Stearyl alcohol | 8.0 | 8.0 | 8.0 | 8.0 |
| Cocamide MEA | 4.5 | 4.5 | 4.5 | 4.5 |
| Glyceryl stearate (SE) | 1.3 | 1.3 | 1.3 | 1.3 |
| Ceteareth-30 | 4.0 | 4.0 | 4.0 | 4.0 |
| Na Lauryl sulfate | 1.0 | 1.0 | 1.0 | 1.0 |
| Oleic acid | 2.0 | 2.0 | 2.0 | 2.0 |
| Propylene glycol | 1.5 | 1.5 | 1.5 | 1.5 |
| PEG-9 Dimethicone*[1] | 1.5 | 1.5 | 1.5 | 1.5 |
| Hydrolyzed keratin | 0.5 | 0.5 | 0.5 | 0.5 |
| Panthenol | 0.8 | 0.8 | 0.8 | 0.8 |
| EDTA-4Na | 0.5 | 0.5 | 0.5 | 0.5 |
| Ammonium chloride | q.s.*[2] | q.s.*[2] | q.s.*[2] | q.s.*[2] |
| Purified water | Balance | Balance | Balance | Balance |
| Total | 100.0 | 100.0 | 100.0 | 100.0 |

*[1]"KF-6005": product of Shin-etsu Chemical

*[2]Amount to adjust pH to 10

TABLE 5

| (Mass %) | Common second agent |
| --- | --- |
| Cetanol | 2.0 |
| Sodium lauryl sulfate | 1.0 |
| Hydrogen peroxide (50%) | 12.0 |
| Methylparaben | 0.1 |
| Phosphoric acid | q.s.*[3] |
| Purified water | Balance |
| Total | 100.0 |

*[3]Amount to adjust pH to 3.5

Examples 1-15 to 1-18

The first part of each of the two-part hair dyes shown in Table 6 is prepared and the first part and the common second part (Table 5) are mixed at a 1:1 mass ratio to yield a hair dye composition. To 1 g of a tress made of human hair and containing 10% of gray hair, an equal amount of the hair dye composition is applied. After being allowed to stand for 30 minutes, the tress is washed with water and a shampoo, and then dried.

TABLE 6

| (Mass %) | Example 1-15 | Example 1-16 | Example 1-17 | Example 1-18 |
| --- | --- | --- | --- | --- |
| D1-46 | 0.3 | 0.1 | 0.3 | 0.1 |
| D1-47 | — | — | 0.2 | — |
| D1-49 | — | 0.2 | — | — |
| Direct dye X | — | — | 0.3 | — |
| Direct dye Y | — | — | — | 0.4 |
| Direct dye Z | — | 0.3 | — | — |
| Toluene-2,5-diamine sulfate | 0.2 | 0.3 | — | 0.2 |
| Para-aminophenol | — | — | 0.1 | — |
| Meta-aminophenol | 0.2 | — | 0.1 | — |
| 5-Amino-ortho-cresol | — | 0.3 | — | 0.2 |
| Behentrimonium chloride | 2.1 | 2.1 | 2.1 | 2.1 |
| Mineral oil | 0.5 | 0.5 | 0.5 | 0.5 |
| Propylene glycol | 7.0 | 7.0 | 7.0 | 7.0 |
| Cetearyl alcohol | 7.0 | 7.0 | 7.0 | 7.0 |
| Aqueous ammonia (28%) | 6.5 | 6.5 | 6.5 | 6.5 |
| Polyquaternium-10*[4] | 1.0 | — | — | 1.0 |
| Amodimethicone*[5] | 1.5 | 1.5 | 1.5 | — |
| Purified water | Balance | Balance | Balance | Balance |
| Total | 100.0 | 100.0 | 100.0 | 100.0 |

Direct dye X

TABLE 6-continued

| (Mass %) | Example 1-15 | Example 1-16 | Example 1-17 | Example 1-18 |
|---|---|---|---|---|

Direct dye Y

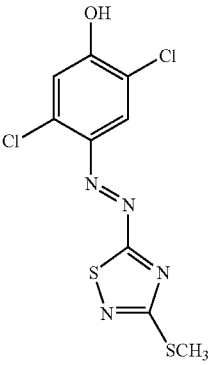

Direct dye Z

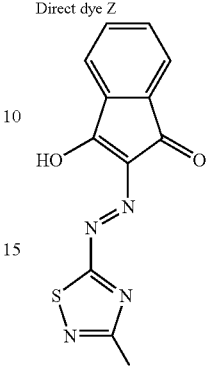

*[4]"Ucare Polymer JR-400", product of Amerchol
*[5]"SM8704C": product of Dow Corning Toray

Examples 1-19 to 1-22

The first part of each of the two-part hair dyes and each of the booster solutions shown in Table 7 are prepared and the first part, the booster solution, and the common second part (Table 5) are mixed at a 1:1:0.1 mass ratio to yield a hair dye composition. To 1 g of a tress made of human hair and containing 10% of gray hair, an equal amount of the hair dye composition is applied. After being allowed to stand for 30 minutes, the tress is washed with water and a shampoo, and then dried.

TABLE 7

| | (Mass %) | Example 1-19 | Example 1-20 | Example 1-21 | Example 1-22 |
|---|---|---|---|---|---|
| First part | D1-31 | 0.5 | 0.4 | 0.3 | 0.1 |
| | D1-35 | — | 0.2 | — | 0.2 |
| | D1-48 | — | 0.2 | — | 0.2 |
| | HC red 3 | 1.0 | — | 0.3 | — |
| | Basic blue 99 | — | 1.0 | — | 0.1 |
| | Para-aminophenol | — | 0.2 | 0.2 | 0.1 |
| | Toluene-2,5-diamine sulfate | 0.2 | — | 0.4 | — |
| | 5-Amino-ortho-cresol | — | 0.2 | 0.2 | 0.1 |
| | Meta-aminophenol | 0.2 | — | 0.2 | — |
| | Behentrimonium chloride | 2.1 | 2.1 | 2.1 | 2.1 |
| | Mineral oil | 0.5 | 0.5 | 0.5 | 0.5 |
| | Propylene glycol | 7.0 | 7.0 | 7.0 | 7.0 |
| | Cetearyl alcohol | 7.0 | 7.0 | 7.0 | 7.0 |
| | Aqueous ammonia (28%) | 6.5 | 6.5 | 6.5 | 6.5 |
| | Polyquaternium-10*[6] | 1.0 | — | 1.0 | — |
| | Amodimethicone*[7] | 1.5 | 1.5 | 1.5 | 1.5 |
| | Purified water | Balance | Balance | Balance | Balance |
| | Total | 100.0 | 100.0 | 100.0 | 100.0 |
| Booster solution | D1-46 | 1.0 | 0.6 | — | 0.4 |
| | Direct dye X | — | 0.4 | 1.5 | — |
| | Aqueous ammonia (28%) | 2.0 | 2.0 | 2.0 | 2.0 |
| | PEG-8 | 3.0 | 3.0 | 3.0 | 3.0 |
| | Purified water | Balance | Balance | Balance | Balance |
| | Total | 100.0 | 100.0 | 100.0 | 100.0 |

*[6]"Ucare Polymer JR-400", product of Amerchol
*[7]"SM8704C", product of Dow Corning Toray

Examples 1-23 to 1-25

In a manner known per se in the art, the first part and the third part of each of the cream type three-part hair dyes shown in Table 8 are prepared. The first part, the common second agent (Table 5) and the third part are mixed at a 1:1:0.3 mass ratio to yield a hair dye composition. To 1 g of a tress made of human hair and containing 10% of gray hair, an equal amount of the hair dye composition is applied. After being allowed to stand for 30 minutes, the tress is washed with water and a shampoo, and then dried.

TABLE 8

| (Mass %) | | Example 1-23 | Example 1-24 | Example 1-25 |
|---|---|---|---|---|
| First part | D1-46 | 0.3 | — | 0.3 |
| | Toluene-2,5-diamine sulfate | 0.2 | 0.4 | — |
| | Para-aminophenol | 0.2 | — | 0.3 |
| | Meta-aminophenol | 0.4 | 0.2 | — |
| | 5-Amino-ortho-cresol | — | 0.2 | 0.3 |
| | Ammonia (28%) | 8.0 | 8.0 | 8.0 |
| | Stearyl alcohol | 8.0 | 8.0 | 8.0 |
| | Cocamide MEA | 4.5 | 4.5 | 4.5 |
| | Glyceryl stearate (SE) | 1.3 | 1.3 | 1.3 |
| | Ceteareth-30 | 4.0 | 4.0 | 4.0 |
| | Na Lauryl sulfate | 1.0 | 1.0 | 1.0 |
| | Oleic acid | 2.0 | 2.0 | 2.0 |
| | Propylene glycol | 1.5 | 1.5 | 1.5 |
| | PEG-9 Dimethicone*[8] | 1.5 | — | — |
| | Hydrolyzed keratin | 0.5 | 0.5 | 0.5 |
| | Panthenol | 0.8 | 0.8 | 0.8 |
| | EDTA-4Na | 0.5 | 0.5 | 0.5 |
| | Ammonium chloride | q.s.*[9] | q.s.*[9] | q.s.*[9] |
| | Purified water | Balance | Balance | Balance |
| | Total | 100.0 | 100.0 | 100.0 |
| Third part | D1-35 | — | 0.5 | 0.3 |
| | Ammonium persulfate (g)*[10] | 5.0 | 5.0 | 5.0 |

*[8]KF-6005 product of Shin-etsu Chemical
*[9]Amount to adjust pH to 10
*[10]Purity: 95% (in the form of powder)

Synthesis Examples 2-1 to 2-13

Dissociative azo dye D2-31 is synthesized in accordance with the following reaction scheme:

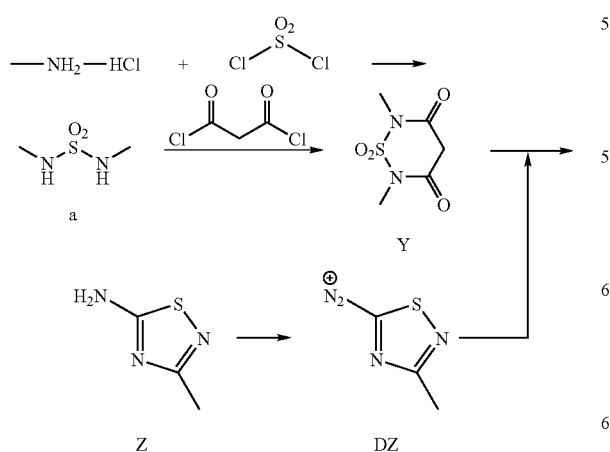

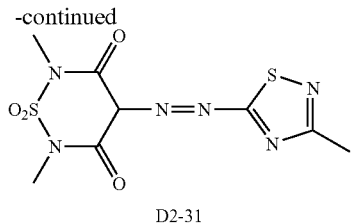

Compound Z (6.4 g, 0.056 mol) is dissolved in 54 g of 85% phosphoric acid. While stirring, 4.2 g of sodium nitrite is added in portions in the form of a powder to the resulting solution at 0° C. or less over about one hour. After completion of the addition, stirring is continued for one further hour at 0° C. While stirring, the reaction mixture is added to a solution of Compound Y in 2-methoxyethanol (9.7 g/100 mL) at 0° C. or less. After stirring is continued for one hour without changing the temperature, 300 mL of water is poured into the reaction mixture. Crystals thus precipitated are collected by filtration and then washed with water. The crystals are air dried overnight at room temperature, followed by recrystallization from N,N-dimethylacetamide/methanol/acetonitrile to yield 5 g of yellow Dissociative azo dye D2-31. Yield: 31%.

The dye had a melting point of from 245 to 246° C. and an absorption maximum λmax in DMF at 398 nm ($\epsilon$: 22200) and developed a good hue.

The dissociative azo dyes synthesized in a similar manner are shown in Table 9.

TABLE 9

| Synthesis Example | | $\lambda_{max}$ (nm) | $\epsilon$ | Yield (%) | Color of crystals |
|---|---|---|---|---|---|
| Synthesis Example 2-1 | D2-31 | 398 | 22200 | 42 | Yellow |
| Synthesis Example 2-2 | D2-21 | 418 | 25100 | 39 | Yellow |
| Synthesis Example 2-3 | D2-23 | 400 | 22000 | 25 | Yellow |
| Synthesis Example 2-4 | D2-26 | 390 | 24600 | 42 | Yellow |
| Synthesis Example 2-5 | D2-27 | 392 | 24000 | 40 | Yellow |
| Synthesis Example 2-6 | D2-29 | 406 | 26200 | 31 | Yellow |
| Synthesis Example 2-7 | D2-32 | 403 | 21300 | 33 | Yellow |
| Synthesis Example 2-8 | D2-34 | 401 | 21900 | 43 | Yellow |
| Synthesis Example 2-9 | D2-36 | 409 | 23100 | 33 | Yellow |
| Synthesis Example 2-10 | D2-40 | 411 | 21800 | 36 | Yellow |
| Synthesis Example 2-11 | D2-42 | 491 | 24200 | 12 | Orange |
| Synthesis Example 2-12 | D2-43 | 487 | 21200 | 15 | Orange |
| Synthesis Example 2-13 | D2-44 | 488 | 22000 | 16 | Orange |

Fastness test is made on the dissociative azo dyes in Table 9 in a similar manner to that employed for the test on Azo dye D1-31 of Synthesis Example 1-1. As a result, the dissociative azo dyes were stable showing neither concentration reduction nor color change and had good fastness to light or heat.

Examples 2-1 to 2-3

Foam-type one-part hair dyes shown in Table 10 are prepared. To 1 g of a tress made of human hair and containing 10% of gray hair, an equal amount of the hair dye composition is applied. After being allowed to stand for 30 minutes, the tress is washed with water and a shampoo, and then dried.

TABLE 10

| (Mass %) | Example 2-1 | Example 2-2 | Example 2-3 |
|---|---|---|---|
| D2-31 | 0.3 | — | 0.1 |
| D2-36 | — | 0.3 | — |

TABLE 10-continued

| (Mass %) | Example 2-1 | Example 2-2 | Example 2-3 |
|---|---|---|---|
| D2-44 | — | — | 0.2 |
| Basic red 76 | 0.3 | — | 0.3 |
| Basic blue 99 | — | 0.2 | — |
| Ammonia (28%) | 8.0 | 8.0 | 8.0 |
| Isopropyl alcohol | 3.5 | 3.5 | 3.5 |
| Polyoxyethylene lauryl ether (23E.O) | 0.5 | 0.5 | 0.5 |
| Benzyl alcohol | — | — | 8.0 |
| Oleic acid | 7.5 | 7.5 | 7.5 |
| LPG (4.0 kg/cm$^2$) | 10.0 | 10.0 | 10.0 |
| Purified water | Balance | Balance | Balance |
| Total | 100.0 | 100.0 | 100.0 |

Examples 2-4 to 2-7

The first part of each of the cream-type two-part hair dyes shown in Table 11 is prepared and the first part and the common second part (Table 5) are mixed at a 1:1 mass ratio to yield a hair dye composition. To 1 g of a tress made of human hair and containing 10% of gray hair, an equal amount of the hair dye composition is applied. After being allowed to stand for 30 minutes, the tress is washed with water and a shampoo, and then dried.

TABLE 11

| (Mass %) | Example 2-4 | Example 2-5 | Example 2-6 | Example 2-7 |
|---|---|---|---|---|
| D2-21 | 0.5 | 0.3 | 0.1 | 0.1 |
| D2-27 | — | — | — | 0.2 |
| D2-31 | — | 0.2 | 0.3 | — |
| Toluene-2,5-diamine sulfate | — | 0.1 | 0.4 | — |
| Para-aminophenol | — | 0.1 | — | 0.1 |
| Meta-aminophenol | — | 0.2 | 0.2 | — |
| 5-Amino-ortho-cresol | — | — | 0.2 | 0.1 |
| Ammonia (28%) | 6.0 | 6.0 | 6.0 | 6.0 |
| Stearyl alcohol | 8.0 | 8.0 | 8.0 | 8.0 |
| Cocamide MEA | 4.5 | 4.5 | 4.5 | 4.5 |
| Glyceryl stearate (SE) | 1.3 | 1.3 | 1.3 | 1.3 |
| Ceteareth-30 | 4.0 | 4.0 | 4.0 | 4.0 |
| Na Lauryl sulfate | 1.0 | 1.0 | 1.0 | 1.0 |
| Oleic acid | 2.0 | 2.0 | 2.0 | 2.0 |
| Propylene glycol | 1.5 | 1.5 | 1.5 | 1.5 |
| PEG-9 Dimethicone*[1] | 1.5 | 1.5 | 1.5 | 1.5 |
| Hydrolyzed keratin | 0.5 | 0.5 | 0.5 | 0.5 |
| Panthenol | 0.8 | 0.8 | 0.8 | 0.8 |
| EDTA-4Na | 0.5 | 0.5 | 0.5 | 0.5 |
| Ammonium chloride | q.s.*[2] | q.s.*[2] | q.s.*[2] | q.s.*[2] |
| Purified water | Balance | Balance | Balance | Balance |
| Total | 100.0 | 100.0 | 100.0 | 100.0 |

*[1]"KF-6005", product of Shin-etsu Chemical
*[2]Amount to adjust pH to 10

Examples 2-8 to 2-11

The first part of each of the two-part hair dyes shown in Table 12 is prepared and the first part and the common second part (Table 5) are mixed at a 1:1 mass ratio to yield a hair dye composition. To 1 g of a tress made of human hair and containing 10% of gray hair, an equal amount of the hair dye composition is applied. After being allowed to stand for 30 minutes, the tress is washed with water and a shampoo, and then dried.

TABLE 12

| (Mass %) | Example 2-8 | Example 2-9 | Example 2-10 | Example 2-11 |
|---|---|---|---|---|
| D2-34 | 0.3 | 0.1 | 0.3 | 0.1 |
| D2-36 | — | — | 0.2 | — |
| D2-40 | — | 0.2 | — | — |
| Direct dye X | — | — | 0.3 | — |
| Direct dye Y | — | — | — | 0.4 |
| Direct dye Z | — | 0.3 | — | — |
| Toluene-2,5-diamine sulfate | 0.2 | 0.3 | — | 0.2 |
| Para-aminophenol | — | — | 0.1 | — |
| Meta-aminophenol | 0.2 | — | 0.1 | — |
| 5-Amino-ortho-cresol | — | 0.3 | — | 0.2 |
| Behentrimonium chloride | 2.1 | 2.1 | 2.1 | 2.1 |
| Mineral oil | 0.5 | 0.5 | 0.5 | 0.5 |
| Propylene glycol | 7.0 | 7.0 | 7.0 | 7.0 |
| Cetearyl alcohol | 7.0 | 7.0 | 7.0 | 7.0 |
| Aqueous ammonia (28%) | 6.5 | 6.5 | 6.5 | 6.5 |
| Polyquaternium-10*[4] | 1.0 | — | — | 1.0 |
| Amodimethicone*[5] | 1.5 | 1.5 | 1.5 | — |
| Purified water | Balance | Balance | Balance | Balance |
| Total | 100.0 | 100.0 | 100.0 | 100.0 |

Direct dye X

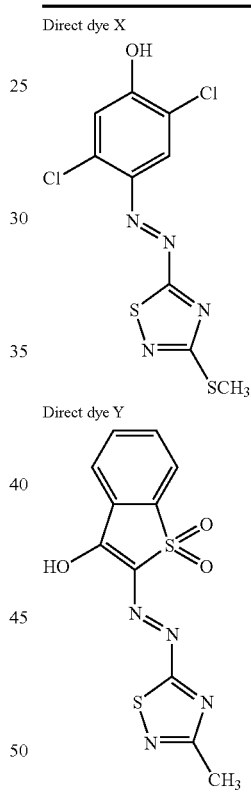

Direct dye Y

Direct dye Z

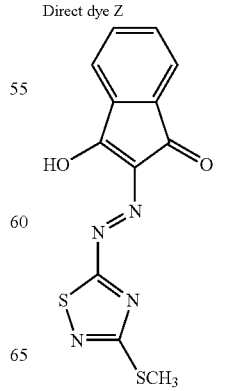

TABLE 12-continued

| (Mass %) | Example 2-8 | Example 2-9 | Example 2-10 | Example 2-11 |
|---|---|---|---|---|
| *4"Ucare Polymer JR-400", product of Amerchol | | | | |
| *5"SM8704C", product of Dow Corning Toray | | | | |

Examples 2-12 to 2-15

The first part of each of the two-part hair dyes and each booster solution shown in Table 13 are prepared and the first part, the booster solution, and the common second part (Table 5) are mixed at a 1:1:0.1 mass ratio to yield a hair dye composition. To 1 g of a tress made of human hair and containing 10% of gray hair, an equal amount of the hair dye composition is applied. After being allowed to stand for 30 minutes, the tress is washed with water and a shampoo, and then dried.

TABLE 13

| | (Mass %) | Example 2-12 | Example 2-13 | Example 2-14 | Example 2-15 |
|---|---|---|---|---|---|
| First part | D2-31 | 0.5 | 0.4 | 0.3 | 0.1 |
| | D2-40 | — | 0.2 | — | 0.2 |
| | D2-43 | — | 0.2 | — | 0.2 |
| | HC red 3 | 1.0 | — | 0.3 | — |
| | Basic blue 99 | — | 1.0 | — | 0.1 |
| | Para-aminophenol | — | 0.2 | 0.2 | 0.1 |
| | Toluene-2,5-diamine sulfate | 0.2 | — | 0.4 | — |
| | 5-Amino-ortho-cresol | — | 0.2 | 0.2 | 0.1 |
| | Meta-aminophenol | 0.2 | — | 0.2 | — |
| | Behentrimonium chloride | 2.1 | 2.1 | 2.1 | 2.1 |
| | Mineral oil | 0.5 | 0.5 | 0.5 | 0.5 |
| | Propylene glycol | 7.0 | 7.0 | 7.0 | 7.0 |
| | Cetearyl alcohol | 7.0 | 7.0 | 7.0 | 7.0 |
| | Aqueous ammonia (28%) | 6.5 | 6.5 | 6.5 | 6.5 |
| | Polyquaternium-10*6 | 1.0 | — | 1.0 | — |
| | Amodimethicone*7 | 1.5 | 1.5 | 1.5 | 1.5 |
| | Purified water | Balance | Balance | Balance | Balance |
| | Total | 100.0 | 100.0 | 100.0 | 100.0 |
| Booster solution | D2-46 | 1.0 | 0.6 | — | 0.4 |
| | Direct dye X | — | 0.4 | 1.5 | — |
| | Aqueous ammonia (28%) | 2.0 | 2.0 | 2.0 | 2.0 |
| | PEG-8 | 3.0 | 3.0 | 3.0 | 3.0 |
| | Purified water | Balance | Balance | Balance | Balance |
| | Total | 100.0 | 100.0 | 100.0 | 100.0 |

*6"Ucare Polymer JR-400", product of Amerchol
*7"SM8704C", product of Dow Corning Toray

Examples 2-16 to 2-18

In a manner known per se in the art, the first part and the third part of each of the cream-type three-part hair dyes shown in Table 14 are prepared. The first part, the common second part shown in Table 5 and the third part are mixed at a 1:1:0.3 mass ratio to yield a hair dye composition. To 1 g of a tress made of human hair and containing 10% of gray hair, an equal amount of the hair dye composition is applied. After being allowed to stand for 30 minutes, the tress is washed with water and a shampoo, and then dried.

TABLE 14

| | (Mass %) | Example 2-16 | Example 2-17 | Example 2-18 |
|---|---|---|---|---|
| First part | D2-27 | 0.3 | — | 0.3 |
| | Toluene-2,5-diamine sulfate | 0.2 | 0.4 | — |
| | Para-aminophenol | 0.2 | — | 0.3 |
| | Meta-aminophenol | 0.4 | 0.2 | — |
| | 5-Amino-ortho-cresol | — | 0.2 | 0.3 |
| | Ammonia (28%) | 8.0 | 8.0 | 8.0 |
| | Stearyl alcohol | 8.0 | 8.0 | 8.0 |
| | Cocamide MEA | 4.5 | 4.5 | 4.5 |
| | Glyceryl stearate (SE) | 1.3 | 1.3 | 1.3 |
| | Ceteareth-30 | 4.0 | 4.0 | 4.0 |
| | Na Lauryl sulfate | 1.0 | 1.0 | 1.0 |
| | Oleic acid | 2.0 | 2.0 | 2.0 |
| | Propylene glycol | 1.5 | 1.5 | 1.5 |
| | PEG-9 Dimethicone*8 | 1.5 | — | — |
| | Hydrolyzed keratin | 0.5 | 0.5 | 0.5 |
| | Panthenol | 0.8 | 0.8 | 0.8 |
| | EDTA-4Na | 0.5 | 0.5 | 0.5 |
| | Ammonium chloride | q.s.*9 | q.s.*9 | q.s.*9 |
| | Purified water | Balance | Balance | Balance |
| | Total | 100.0 | 100.0 | 100.0 |
| Third part | D2-36 | — | 0.5 | 0.3 |
| | Ammonium persulfate (g)*10 | 5.0 | 5.0 | 5.0 |

*8"KF-6005"; product of Shin-etsu Chemical
*9Amount to adjust pH to 10
*10Purity: 95% (in the form of powder)

Synthesis Examples 3-1 to 3-10

Dissociative azo dye D3-31 is synthesized in accordance with the following reaction scheme:

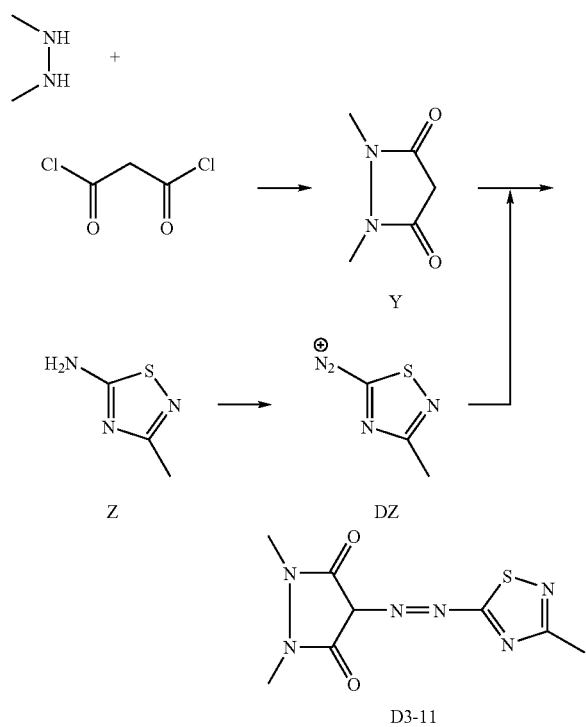

D3-11

Compound Z (6.4 g, 0.056 mol) is dissolved in 54 g of 85% phosphoric acid. While stirring, 4.2 g of sodium nitrite is added in portions in the form of a powder to the resulting solution at 0° C. or less over about one hour. After completion of the addition, stirring is continued for one further hour at 0° C. While stirring, the reaction mixture is added to a solution of Compound Y in 2-methoxyethanol (6.5 g/100 mL) at 0° C. or less. After stirring is continued for one hour without changing the temperature, 300 mL of water is added to the reaction mixture. Crystals thus precipitated are collected by filtration and then washed with water. The crystals are air dried overnight at room temperature, followed by recrystallization from N,N-dimethylacetamide/methanol/acetonitrile to yield 3.6 g of Dissociative azo dye D3-11. Yield: 28%.

The dye had a melting point of from 234 to 235° C. and an absorption maximum λmax in DMF at 410 nm ($\epsilon$:24400) and developed a good hue.

The dissociative azo dyes synthesized in a similar manner are shown in Table 15.

TABLE 15

| Synthesis Example | | $\lambda_{max}$ (nm) | $\epsilon$ | Yield (%) | Color of crystals |
|---|---|---|---|---|---|
| Synthesis Example 3-1 | D3-11 | 410 | 24400 | 28 | Yellow |
| Synthesis Example 3-2 | D3-1 | 436 | 31000 | 41 | Yellow |
| Synthesis Example 3-3 | D3-3 | 410 | 23100 | 33 | Yellow |
| Synthesis Example 3-4 | D3-6 | 401 | 29000 | 50 | Yellow |
| Synthesis Example 3-5 | D3-8 | 415 | 25000 | 39 | Yellow |
| Synthesis Example 3-6 | D3-9 | 417 | 29800 | 33 | Yellow |
| Synthesis Example 3-7 | D3-10 | 416 | 23000 | 38 | Yellow |
| Synthesis Example 3-8 | D3-12 | 417 | 23100 | 33 | Yellow |
| Synthesis Example 3-9 | D3-17 | 498 | 28300 | 13 | Red |
| Synthesis Example 3-10 | D3-18 | 503 | 29000 | 15 | Red |

Fastness test is performed on the dissociative azo dyes in Table 15 in a similar manner to that employed for Azo dye D1-31 of Synthesis Example 1-1. As a result, the dissociative azo dyes were stable without concentration reduction or color change and had good fastness to light or heat.

Example 3-1

The first part of the two-part hair dye shown in Table 16 and 6 mass % aqueous hydrogen peroxide (second part) are prepared. The first part, the second part, and purified water are mixed at a mass ratio of 4:7:1 to yield a hair cosmetic composition. To 1 g of goat hair, 1 g of the hair dye composition is applied at 30° C. After being allowed to stand for 30 minutes, the hair is washed with water and a shampoo, and dried.

After hair dyeing, the chromaticities of the tress before and after the coloring treatment are measured and a chromaticity change ΔE* is calculated. As a result, the ΔE* was 58.4.

TABLE 16

| (Mass %) | Example 3-1 |
|---|---|
| Dye D3-11 | 1.2 |
| Aqueous ammonia (28%) | 9.0 |
| Purified water | Balance |
| Total | 100.0 |

Examples 3-2 to 3-4

The foam-type one-part hair dyes shown in Table 17 are prepared. To 1 g of a tress made of human hair and containing 10% of gray hair, an equal amount of the hair dye composition is applied. After being allowed to stand for 30 minutes, the hair is washed with water and a shampoo, and dried.

TABLE 17

| (Mass %) | Example 3-2 | Example 3-3 | Example 3-4 |
|---|---|---|---|
| D3-1 | 0.3 | — | 0.1 |
| D3-6 | — | 0.3 | — |
| D3-11 | — | — | 0.2 |
| Basic red 76 | 0.3 | — | 0.3 |
| Basic blue 99 | — | 0.2 | — |
| Ammonia (28%) | 8.0 | 8.0 | 8.0 |
| Isopropyl alcohol | 3.5 | 3.5 | 3.5 |
| Polyoxyethylene lauryl ether (23E.O) | 0.5 | 0.5 | 0.5 |
| Benzyl alcohol | — | — | 8.0 |
| Oleic acid | 7.5 | 7.5 | 7.5 |
| LPG (4.0 kg/cm$^2$) | 10.0 | 10.0 | 10.0 |
| Purified water | Balance | Balance | Balance |
| Total | 100.0 | 100.0 | 100.0 |

Examples 3-5 to 3-8

The first part of each of the cream-type two-part hair dyes shown in Table 18 is prepared. The first part and the common second agent (Table 5) are mixed at a 1:1 mass ratio to yield a hair dye composition. To 1 g of a tress made of human hair and containing 10% of gray hair, an equal amount of the hair dye composition is applied. After being allowed to stand for 30 minutes, the tress is washed with water and a shampoo, and then dried.

TABLE 18

| (Mass %) | Example 3-5 | Example 3-6 | Example 3-7 | Example 3-8 |
|---|---|---|---|---|
| D3-3 | 0.5 | 0.3 | 0.1 | 0.1 |
| D3-8 | — | — | — | 0.2 |
| D3-9 | — | 0.2 | 0.3 | — |
| Toluene-2,5-diamine sulfate | — | 0.1 | 0.4 | — |
| Para-aminophenol | — | 0.1 | — | 0.1 |
| Meta-aminophenol | — | 0.2 | 0.2 | — |
| 5-Amino-ortho-cresol | — | — | 0.2 | 0.1 |
| Ammonia (28%) | 6.0 | 6.0 | 6.0 | 6.0 |
| Stearyl alcohol | 8.0 | 8.0 | 8.0 | 8.0 |
| Cocamide MEA | 4.5 | 4.5 | 4.5 | 4.5 |
| Glyceryl stearate (SE) | 1.3 | 1.3 | 1.3 | 1.3 |
| Ceteareth-30 | 4.0 | 4.0 | 4.0 | 4.0 |
| Na Lauryl sulfate | 1.0 | 1.0 | 1.0 | 1.0 |
| Oleic acid | 2.0 | 2.0 | 2.0 | 2.0 |
| Propylene glycol | 1.5 | 1.5 | 1.5 | 1.5 |
| PEG-9 Dimethicone[*1] | 1.5 | 1.5 | 1.5 | 1.5 |
| Hydrolyzed keratin | 0.5 | 0.5 | 0.5 | 0.5 |
| Panthenol | 0.8 | 0.8 | 0.8 | 0.8 |
| EDTA-4Na | 0.5 | 0.5 | 0.5 | 0.5 |
| Ammonium chloride | q.s.[*2] | q.s.[*2] | q.s.[*2] | q.s.[*2] |
| Purified water | Balance | Balance | Balance | Balance |
| Total | 100.0 | 100.0 | 100.0 | 100.0 |

[*1]"KF-6005", product of Shin-etsu Chemical
[*2]Amount to adjust pH to 10

Examples 3-9 to 3-12

The first part of each of the two-part hair dyes shown in Table 19 is prepared. The first part and the common second agent (Table 5) are mixed at a 1:1 mass ratio to yield a hair dye composition. To 1 g of a tress made of human hair and containing 10% of gray hair, an equal amount of the hair dye composition is applied. After being allowed to stand for 30 minutes, the tress is washed with water and a shampoo, and then dried.

TABLE 19

| (Mass %) | Example 3-9 | Example 3-10 | Example 3-11 | Example 3-12 |
|---|---|---|---|---|
| D3-10 | 0.3 | 0.1 | 0.3 | 0.1 |
| D3-11 | — | — | 0.2 | — |
| D3-12 | — | 0.2 | — | — |
| Direct dye X | — | — | 0.3 | — |
| Direct dye Y | — | — | — | 0.4 |
| Direct dye Z | — | 0.4 | — | — |
| Toluene-2,5-diamine sulfate | 0.2 | 0.3 | — | 0.2 |
| Para-aminophenol | — | — | 0.1 | — |
| Meta-aminophenol | 0.2 | — | 0.1 | — |
| 5-Amino-ortho-cresol | — | 0.3 | — | 0.2 |
| Behentrimonium chloride | 2.1 | 2.1 | 2.1 | 2.1 |
| Mineral oil | 0.5 | 0.5 | 0.5 | 0.5 |
| Propylene glycol | 7.0 | 7.0 | 7.0 | 7.0 |
| Cetearyl alcohol | 7.0 | 7.0 | 7.0 | 7.0 |
| Aqueous ammonia (28%) | 6.5 | 6.5 | 6.5 | 6.5 |
| Polyquaternium-10[*4] | 1.0 | — | — | 1.0 |
| Amodimethicone[*5] | 1.5 | 1.5 | 1.5 | — |
| Purified water | Balance | Balance | Balance | Balance |
| Total | 100.0 | 100.0 | 100.0 | 100.0 |

Direct dye X

TABLE 19-continued

| (Mass %) | Example 3-9 | Example 3-10 | Example 3-11 | Example 3-12 |
|---|---|---|---|---|

Direct dye Y

Direct dye Z

[*4]"Ucare Polymer", product of JR-400 Amerchol
[*5]"SM8704C", product of Dow Corning Toray Examples 3-13 to 3-16

The first part of each of the two-part hair dyes and each booster solution shown in Table 20 are prepared and the first part, the booster solution, and the common second part (Table 5) are mixed at a 1:1:0.1 mass ratio to yield a hair dye composition. To 1 g of a tress made of human hair and containing 10% of gray hair, an equal amount of the hair dye composition is applied. After being allowed to stand for 30 minutes, the tress is washed with water and a shampoo, and then dried.

TABLE 20

|  | (Mass %) | Example 3-13 | Example 3-14 | Example 3-15 | Example 3-16 |
|---|---|---|---|---|---|
| First part | D3-3 | 0.5 | 0.4 | 0.3 | 0.1 |
|  | D3-11 | — | 0.2 | — | 0.2 |
|  | D3-18 | — | 0.2 | — | 0.2 |
|  | HC red 3 | 1.0 | — | 0.3 | — |
|  | Basic blue 99 | — | 1.0 | — | 0.1 |
|  | Para-aminophenol | — | 0.2 | 0.2 | 0.1 |
|  | Toluene-2,5-diamine sulfate | 0.2 | — | 0.4 | — |
|  | 5-Amino-ortho-cresol | — | 0.2 | 0.2 | 0.1 |
|  | Meta-aminophenol | 0.2 | — | 0.2 | — |
|  | Behentrimonium chloride | 2.1 | 2.1 | 2.1 | 2.1 |
|  | Mineral oil | 0.5 | 0.5 | 0.5 | 0.5 |
|  | Propylene glycol | 7.0 | 7.0 | 7.0 | 7.0 |
|  | Cetearyl alcohol | 7.0 | 7.0 | 7.0 | 7.0 |
|  | Aqueous ammonia (28%) | 6.5 | 6.5 | 6.5 | 6.5 |
|  | Polyquaternium-10*[6] | 1.0 | — | 1.0 | — |
|  | Amodimethicone*[7] | 1.5 | 1.5 | 1.5 | 1.5 |
|  | Purified water | Balance | Balance | Balance | Balance |
|  | Total | 100.0 | 100.0 | 100.0 | 100.0 |
| Booster solution | D3-17 | 1.0 | 0.6 | — | 0.4 |
|  | Direct dye X | — | 0.4 | 1.5 | — |
|  | Aqueous ammonia (28%) | 2.0 | 2.0 | 2.0 | 2.0 |
|  | PEG-8 | 3.0 | 3.0 | 3.0 | 3.0 |
|  | Purified water | Balance | Balance | Balance | Balance |
|  | Total | 100.0 | 100.0 | 100.0 | 100.0 |

*[6]"Ucare Polymer JR-400", product of Amerchol
*[7]"SM8704C", product of Dow Corning Toray Examples 3-17 to 3-19

In a manner known per se in the art, the first part and the third part of each of the cream-type three-part hair dyes shown in Table 21 are prepared. The first part, the common second part (Table 5) and the third part are mixed at a 1:1:0.3 mass ratio to yield a hair dye composition. To 1 g of a tress made of human hair and containing 10% of gray hair, an equal amount of the hair dye composition is applied. After being allowed to stand for 30 minutes, the tress is washed with water and shampoo, and then dried.

TABLE 21

|  | (Mass %) | Example 3-17 | Example 3-18 | Example 3-19 |
|---|---|---|---|---|
| First part | D3-12 | 0.3 | — | 0.3 |
|  | Toluene-2,5-diamine sulfate | 0.2 | 0.4 | — |
|  | Para-aminophenol | 0.2 | — | 0.3 |
|  | Meta-aminophenol | 0.4 | 0.2 | — |
|  | 5-Amino-ortho-cresol | — | 0.2 | 0.3 |
|  | Ammonia (28%) | 8.0 | 8.0 | 8.0 |
|  | Stearyl alcohol | 8.0 | 8.0 | 8.0 |
|  | Cocamide MEA | 4.5 | 4.5 | 4.5 |
|  | Glyceryl stearate (SE) | 1.3 | 1.3 | 1.3 |
|  | Ceteareth-30 | 4.0 | 4.0 | 4.0 |
|  | Na Lauryl sulfate | 1.0 | 1.0 | 1.0 |
|  | Oleic acid | 2.0 | 2.0 | 2.0 |
|  | Propylene glycol | 1.5 | 1.5 | 1.5 |
|  | PEG-9 Dimethicon*[8] | 1.5 | — | — |
|  | Hydrolyzed keratin | 0.5 | 0.5 | 0.5 |
|  | Panthenol | 0.8 | 0.8 | 0.8 |
|  | EDTA-4Na | 0.5 | 0.5 | 0.5 |
|  | Ammonium chloride | q.s.*[9] | q.s.*[9] | q.s.*[9] |
|  | Purified water | Balance | Balance | Balance |
|  | Total | 100.0 | 100.0 | 100.0 |
| Third part | D3-18 | — | 0.5 | 0.3 |
|  | Ammonium persulfate (g)*[10] | 5.0 | 5.0 | 5.0 |

*[8]"KF-6005" product of Shin-etsu Chemical
*[9]Amount to adjust pH to 10
*[10]Purity: 95% (in the form of powder)

Synthesis Example 4-1

In accordance with the following reaction scheme, Dissociative azo dye D4-12 is synthesized.

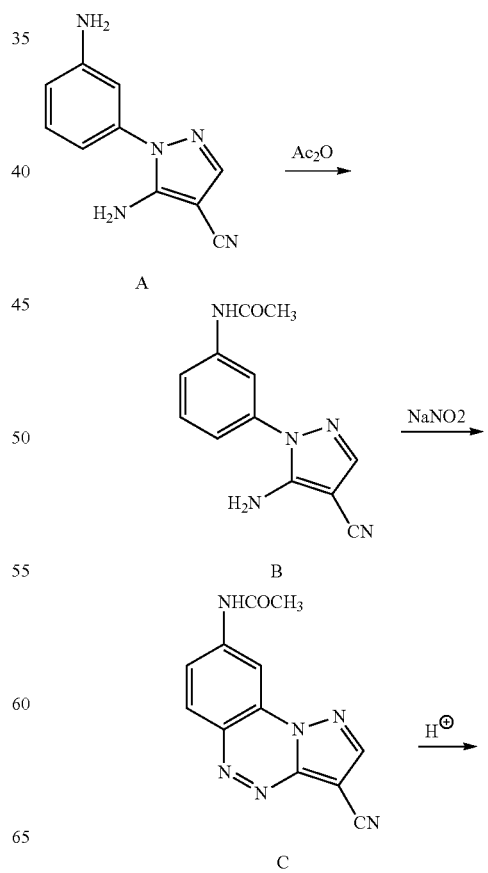

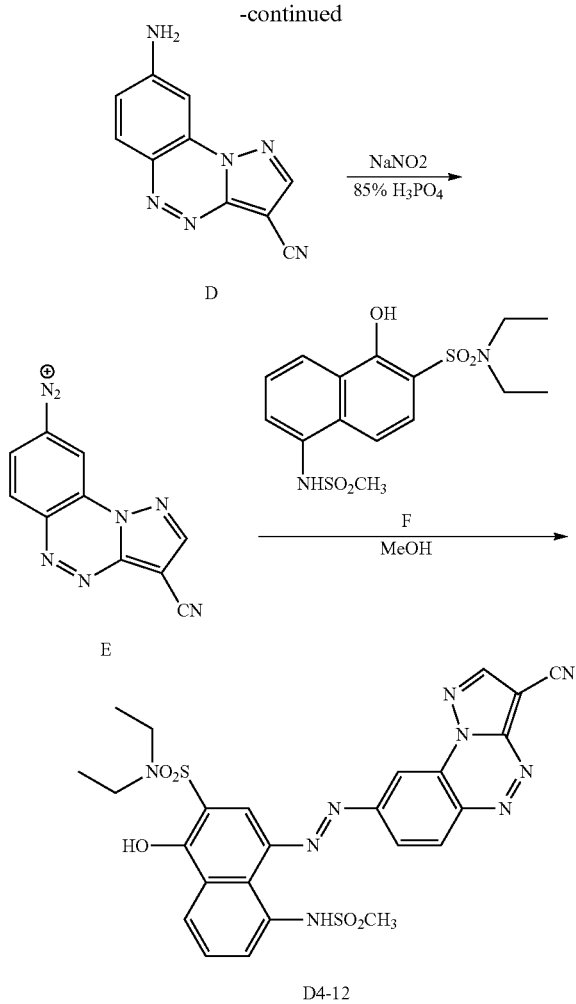

(1) Synthesis of Compound A

Compound (A) (diazo component) serving as a starting material of Diazonium Compound E is synthesized by the process described in JP-A-2006-169239.

(2) Synthesis of Compound C

Compound A (10.0 g) is suspended in 50 mL of acetonitrile. To the resulting suspension is added 4.5 mL of acetic anhydride at room temperature. After stirring for one hour, the reaction mixture is concentrated to dryness under reduced pressure. The residue is extracted with ethyl acetate/water, followed by washing with water and drying overnight over magnesium sulfate. Magnesium sulfate is then filtered out and the filtrate is concentrated to dryness. To the residue is added 150 g of 85% phosphoric acid. While stirring at 0° C. or less, 3.1 g of sodium nitrite is added in portions over about 60 minutes. Stirring is continued for 2 hours without changing the temperature and 500 mL of ice water is added to the reaction mixture. Crystals thus precipitated are collected by filtration, washed with acetonitrile, and purified by column chromatography to yield 5.0 g of Compound C.

(3) Synthesis of Compound D

In a mixed solvent of 30 mL of 35% hydrochloric acid and 30 mL of ethanol is suspended 5.0 g of Compound C. While stirring at from 60 to 70° C., the suspension is reacted for 3 hours. The reaction mixture is concentrated under reduced pressure. To the residue is added 200 mL of ice water. Crystals thus precipitated are collected by filtration, followed by drying to yield 2.5 g of Compound D.

(4) Synthesis of D4-12

Compound D (1.0 g) is dissolved in 20 mL of 85% phosphoric acid. While stirring at 0° C. or less, 0.36 g of sodium nitrite is added in portions over 30 minutes. Stirring is continued for 2 hours without changing the temperature. Compound (F, coupler component, 1.4 g) is dissolved in 150 mL of methanol. While stirring the resulting solution at 0° C. or less, the diazonium salt synthesized in advance is added thereto in portions. After stirring is continued at from 0 to 5° C. for one hour and at from 20 to 25° C. (room temperature) for one hour, 200 mL of water is added to the reaction mixture. Crystals thus precipitated are collected by filtration and dried. The resulting crystals are purified by column chromatography to yield 0.5 g of D4-12. Yield: 20%

Dissociative azo dye D4-12 had a melting point of from 258 to 260° C. and an absorption maximum $\lambda$max in DMF at 677 nm ($\epsilon$: 82,300) and developed a good hue.

Synthesis Examples 4-2 to 4-4

In a similar manner to that employed in Synthesis Example 4-1, a diazo component is synthesized in accordance with the process described in JP-A-2006-143902, JP-A-2006-169239, or Liebigs Annalen der Chemie, 1534 (1979). By using the resulting diazo component and, as a coupler component, 3-ethylisoxazolone, 2,5-difluorophenol, and 2-chlorophenol, Dissociative azo dyes D4-9, D4-25, and D4-35 are synthesized, respectively.

D4-9: melting point: 210 to 212° C. (decomposition), absorption maximum at 564 nm (in DMF)

D4-25: melting point: 233° C., absorption maximum at 624 nm (in DMF)

D4-35: melting point: 237 to 238° C., absorption maximum at 653 nm (in DMF)

The dissociative azo dyes synthesized in a similar manner are shown in Table 22.

TABLE 22

| Synthe0sis Example | | $\lambda_{max}$ (nm) | $\epsilon$ | Yield (%) | Color of crystals |
|---|---|---|---|---|---|
| Synthesis Example 4-1 | D4-12 | 677 | 82,300 | 20 | Blue |
| Synthesis Example 4-2 | D4-9 | 564 | 32,000 | 31 | Reddish violet |
| Synthesis Example 4-3 | D4-25 | 624 | 56,700 | 33 | Blue |
| Synthesis Example 4-4 | D4-35 | 667 | 51,000 | 33 | Bluish green |
| Synthesis Example 4-5 | D4-2 | 650 | 20,000 | 20 | Bluish green |
| Synthesis Example 4-6 | D4-4 | 640 | 21,000 | 28 | Bluish green |
| Synthesis Example 4-7 | D4-13 | 551 | 14,700 | 31 | Reddish violet |
| Synthesis Example 4-8 | D4-15 | 599 | 22,000 | 38 | Blue |
| Synthesis Example 4-9 | D4-16 | 558 | 15,300 | 21 | Reddish violet |
| Synthesis Example 4-10 | D4-17 | 617 | 29,600 | 23 | Blue |
| Synthesis Example 4-11 | D4-26 | 558 | 14,200 | 18 | Reddish violet |
| Synthesis Example 4-12 | D4-27 | 564 | 36,400 | 28 | Reddish violet |
| Synthesis Example 4-13 | D4-28 | 660 | 13,100 | 16 | Bluish violet |
| Synthesis Example 4-14 | D4-29 | 595 | 28,600 | 22 | blue |
| Synthesis Example 4-15 | D4-31 | 584 | 13,600 | 20 | Reddish violet |
| Synthesis Example 4-16 | D4-32 | 550 | 25,700 | 38 | Reddish violet |
| Synthesis Example 4-17 | D4-33 | 533 | 24,800 | 21 | Red |
| Synthesis Example 4-18 | D4-36 | 653 | 53,000 | 38 | Bluish green |

Fastness test is performed on the dissociative azo dyes in Table 22 in a similar manner to that employed for Azo dye D1-31 of Synthesis Example 1-1. As a result, the dissociative azo dyes were stable without concentration reduction or color change and had good fastness to light or heat.

Examples 4-1 to 4-3

The foam-type one-part hair dyes shown in Table 23 are prepared. To 1 g of a tress made of human hair and containing 10% of gray hair, an equal amount of the hair dye composition is applied. After being allowed to stand for 30 minutes, the hair is washed with water and a shampoo, and dried.

TABLE 23

| (Mass %) | Example 4-1 | Example 4-2 | Example 4-3 |
|---|---|---|---|
| D4-12 | 0.3 | — | 0.1 |
| D4-25 | — | 0.3 | — |
| D4-15 | — | — | 0.2 |
| Basic red 76 | 0.3 | — | 0.3 |
| Basic blue 99 | — | 0.2 | — |
| Ammonia (28%) | 8.0 | 8.0 | 8.0 |
| Isopropyl alcohol | 3.5 | 3.5 | 3.5 |
| Polyoxyethylene lauryl ether (23EO) | 0.5 | 0.5 | 0.5 |
| Benzyl alcohol | — | — | 8.0 |
| Oleic acid | 7.5 | 7.5 | 7.5 |
| LPG (4.0 kg/cm$^2$) | 10.0 | 10.0 | 10.0 |
| Purified water | Balance | Balance | Balance |
| Total | 100.0 | 100.0 | 100.0 |

Examples 4-4 to 4-7

The first part of each of the cream-type two-part hair dyes shown in Table 24 and the common second part (Table 5) are prepared and the first part and the common second part are mixed at a 1:1 mass ratio to yield a hair dye composition. To 1 g of a tress made of human hair and containing 10% of gray hair, an equal amount of the hair dye composition is applied. After being allowed to stand for 30 minutes, the tress is washed with water and a shampoo, and then dried.

TABLE 24

| (Mass %) | Example 4-4 | Example 4-5 | Example 4-6 | Example 4-7 |
|---|---|---|---|---|
| D4-12 | 0.5 | 0.3 | 0.1 | 0.1 |
| D4-25 | — | — | — | 0.2 |
| D4-15 | — | 0.2 | 0.3 | — |
| Toluene-2,5-diamine sulfate | — | 0.1 | 0.4 | — |
| Para-aminophenol | — | 0.1 | — | 0.1 |
| Meta-aminophenol | — | 0.2 | 0.2 | — |
| 5-Amino-ortho-cresol | — | — | 0.2 | 0.1 |
| Ammonia (28%) | 6.0 | 6.0 | 6.0 | 6.0 |
| Stearyl alcohol | 8.0 | 8.0 | 8.0 | 8.0 |
| Cocamide MEA | 4.5 | 4.5 | 4.5 | 4.5 |
| Glyceryl stearate (SE) | 1.3 | 1.3 | 1.3 | 1.3 |
| Ceteareth-30 | 4.0 | 4.0 | 4.0 | 4.0 |
| Na Lauryl sulfate | 1.0 | 1.0 | 1.0 | 1.0 |
| Oleic acid | 2.0 | 2.0 | 2.0 | 2.0 |
| Propylene glycol | 1.5 | 1.5 | 1.5 | 1.5 |
| PEG-9 Dimethicone[*1] | 1.5 | 1.5 | 1.5 | 1.5 |
| Hydrolyzed keratin | 0.5 | 0.5 | 0.5 | 0.5 |
| Panthenol | 0.8 | 0.8 | 0.8 | 0.8 |
| EDTA-4Na | 0.5 | 0.5 | 0.5 | 0.5 |
| Ammonium chloride | q.s.[*2] | q.s.[*2] | q.s.[*2] | q.s.[*2] |
| Purified water | Balance | Balance | Balance | Balance |
| Total | 100.0 | 100.0 | 100.0 | 100.0 |

[*1]"KF-6005", product of Shin-etsu Chemical
[*2]Amount to adjust pH to 10

Examples 4-8 to 4-11

The first part of each of the two-part hair dyes shown in Table 25 is prepared and the first part and the common second part (Table 5) are mixed at a 1:1 mass ratio to yield a hair dye composition. To 1 g of a tress made of human hair and containing 10% of gray hair, an equal amount of the hair dye composition is applied. After being allowed to stand for 30 minutes, the tress is washed with water and a shampoo, and then dried.

TABLE 25

| (Mass %) | Example 4-8 | Example 4-9 | Example 4-10 | Example 4-11 |
|---|---|---|---|---|
| D4-12 | 0.3 | 0.1 | 0.3 | 0.1 |
| D4-25 | — | — | 0.2 | — |
| D4-1 | — | 0.2 | — | — |
| Direct dye X | — | — | 0.3 | — |
| Direct dye Y | — | — | — | 0.4 |
| Direct dye Z | — | 0.5 | — | — |
| Toluene-2,5-diamine sulfate | 0.2 | 0.3 | — | 0.2 |
| Para-aminophenol | — | — | 0.1 | — |
| Meta-aminophenol | 0.2 | — | 0.1 | — |
| 5-Amino-ortho-cresol | — | 0.3 | — | 0.2 |
| Behentrimonium chloride | 2.1 | 2.1 | 2.1 | 2.1 |
| Mineral oil | 0.5 | 0.5 | 0.5 | 0.5 |
| Propylene glycol | 7.0 | 7.0 | 7.0 | 7.0 |
| Cetearyl alcohol | 7.0 | 7.0 | 7.0 | 7.0 |
| Aqueous ammonia (28%) | 6.5 | 6.5 | 6.5 | 6.5 |
| Polyquaternium-10[*4] | 1.0 | — | — | 1.0 |
| Amodimethicone[*5] | 1.5 | 1.5 | 1.5 | — |
| Purified water | Balance | Balance | Balance | Balance |
| Total | 100.0 | 100.0 | 100.0 | 100.0 |

Direct dye X

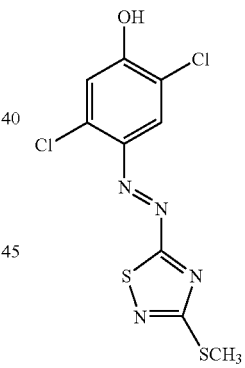

Direct dye Y

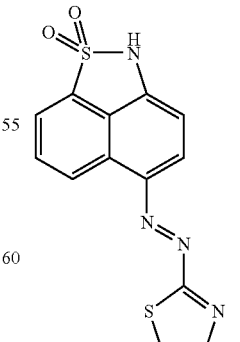

Direct dye Z

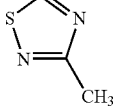

TABLE 25-continued

| (Mass %) | Example 4-8 | Example 4-9 | Example 4-10 | Example 4-11 |
|---|---|---|---|---|

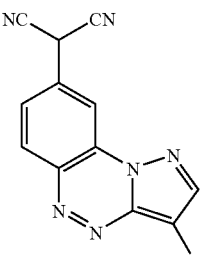

*[4]"Ucare Polymer JR-400", product of Amerchol
*[5]"SM8704C", product of Dow Corning Toray

Examples 4-12 to 4-15

The first part and the booster solution of each of the two-part hair dyes shown in Table 26 are prepared and the first part, the booster solution, and the common second part (Table 5) are mixed at a 1:1:0.1 mass ratio to yield a hair dye composition. To 1 g of a tress made of human hair and containing 10% of gray hair, an equal amount of the hair dye composition is applied. After being allowed to stand for 30 minutes, the tress is washed with water and a shampoo, and then dried.

Examples 4-16 to 4-18

In a manner known per se in the art, the first part and the third part of each of the cream-type three-part hair dyes shown in Table 7 are prepared. The first part, the common second part (Table 5) and the third part are mixed at a 1:1:0.3 mass ratio to yield a hair dye composition. To 1 g of a tress made of human hair and containing 10% of gray hair, an equal amount of the hair dye composition is applied. After being allowed to stand for 30 minutes, the tress is washed with water and a shampoo, and then dried.

TABLE 27

| | (Mass %) | Example 4-16 | Example 4-17 | Example 4-18 |
|---|---|---|---|---|
| First part | D4-25 | 0.3 | — | 0.3 |
| | Toluene-2,5-diamine sulfate | 0.2 | 0.4 | — |
| | Para-aminophenol | 0.2 | — | 0.3 |
| | Meta-aminophenol | 0.4 | 0.2 | — |
| | 5-Amino-ortho-cresol | — | 0.2 | 0.3 |
| | Ammonia (28%) | 8.0 | 8.0 | 8.0 |
| | Stearyl alcohol | 8.0 | 8.0 | 8.0 |
| | Cocamide MEA | 4.5 | 4.5 | 4.5 |
| | Glyceryl stearate (SE) | 1.3 | 1.3 | 1.3 |
| | Ceteareth-30 | 4.0 | 4.0 | 4.0 |
| | Na Lauryl sulfate | 1.0 | 1.0 | 1.0 |
| | Oleic acid | 2.0 | 2.0 | 2.0 |
| | Propylene glycol | 1.5 | 1.5 | 1.5 |
| | PEG-9 Dimethicone*[8] | 1.5 | — | — |
| | Hydrolyzed keratin | 0.5 | 0.5 | 0.5 |
| | Panthenol | 0.8 | 0.8 | 0.8 |
| | EDTA-4Na | 0.5 | 0.5 | 0.5 |
| | Ammonium chloride | q.s.*[9] | q.s.*[9] | q.s.*[9] |
| | Purified water | Balance | Balance | Balance |

TABLE 26

| | (Mass %) | Example 4-12 | Example 4-13 | Example 4-14 | Example 4-15 |
|---|---|---|---|---|---|
| First part | D4-12 | 0.5 | 0.4 | 0.3 | 0.1 |
| | D4-6 | — | 0.2 | — | 0.2 |
| | D4-25 | — | 0.2 | — | 0.2 |
| | HC red 3 | 1.0 | — | 0.3 | — |
| | Basic blue 99 | — | 1.0 | — | 0.1 |
| | Para-aminophenol | — | 0.2 | 0.2 | 0.1 |
| | Toluene-2,5-diamine sulfate | 0.2 | — | 0.4 | — |
| | 5-Amino-ortho-cresol | — | 0.2 | 0.2 | 0.1 |
| | Meta-aminophenol | 0.2 | — | 0.2 | — |
| | Behentrimonium chloride | 2.1 | 2.1 | 2.1 | 2.1 |
| | Mineral oil | 0.5 | 0.5 | 0.5 | 0.5 |
| | Propylene glycol | 7.0 | 7.0 | 7.0 | 7.0 |
| | Cetearyl alcohol | 7.0 | 7.0 | 7.0 | 7.0 |
| | Aqueous ammonia (28%) | 6.5 | 6.5 | 6.5 | 6.5 |
| | Polyquaternium-10*[6] | 1.0 | — | 1.0 | — |
| | Amodimethicone*[7] | 1.5 | 1.5 | 1.5 | 1.5 |
| | Purified water | Balance | Balance | Balance | Balance |
| | Total | 100.0 | 100.0 | 100.0 | 100.0 |
| Booster solution | D4-23 | 1.0 | 0.6 | — | 0.4 |
| | Direct dye X | — | 0.4 | 1.5 | — |
| | Aqueous ammonia (28%) | 2.0 | 2.0 | 2.0 | 2.0 |
| | PEG-8 | 3.0 | 3.0 | 3.0 | 3.0 |
| | Purified water | Balance | Balance | Balance | Balance |
| | Total | 100.0 | 100.0 | 100.0 | 100.0 |

*[6]"Ucare Polymer JR-400", product of Amerchol
*[7]"SM8704C", product of Dow Corning Toray TABLE 27-continued

| (Mass %) | | Example 4-16 | Example 4-17 | Example 4-18 |
|---|---|---|---|---|
| | Total | 100.0 | 100.0 | 100.0 |
| Third part | D4-23 | — | 0.5 | 0.3 |
| | Ammonium persulfate (g)*[10] | 5.0 | 5.0 | 5.0 |

*[8]"KF-6005", product of Shin-etsu Chemical
*[9]Amount to adjust pH to 10
*[10]Purity: 95% (in the form of powder)

Synthesis Example 5-1

In accordance with the following reaction scheme, Dissociative azo dye D5-23 is synthesized.

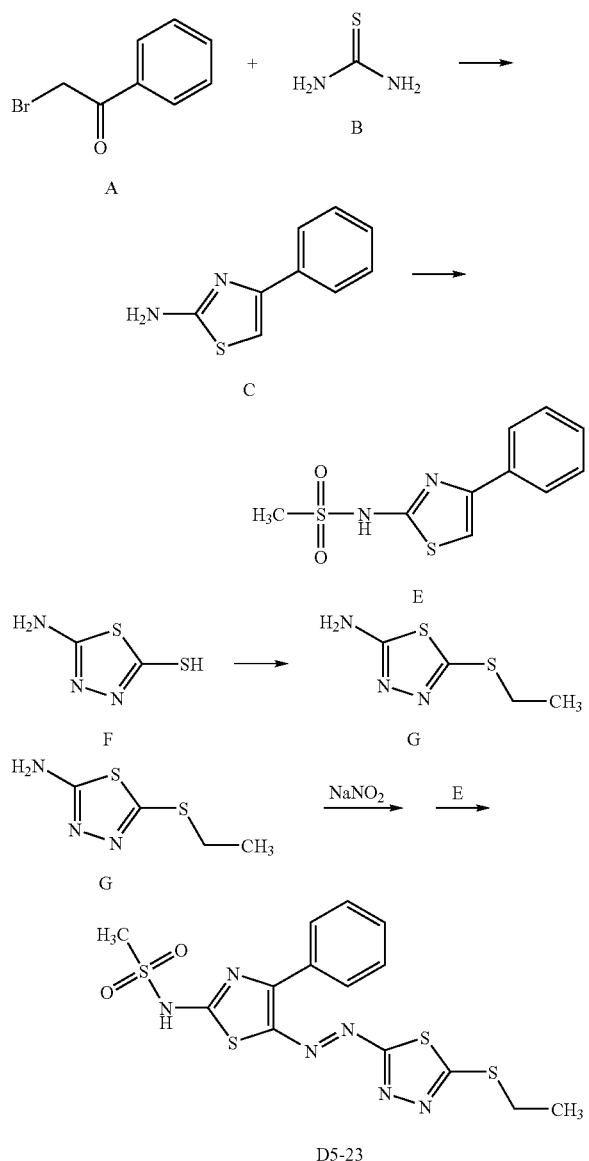

(1) Synthesis of Compound C

Compound (A) (16.2 g, 0.08 mol) and 6.2 g (0.08 mol) of Compound B are suspended in 80 mL of isopropyl alcohol and the resulting suspension is stirred for 3 hours at an internal temperature of 25° C. A solution obtained by dissolving 6.9 g (0.082 mol) of sodium bicarbonate in 200 mL of water is added dropwise. Crystals thus precipitated are filtered, rinsed sufficiently with water, and dried to yield 14.0 g of Compound C as colorless crystals. Yield: 99%.

(2) Synthesis of Compound E

After 10.0 g (0.055 mol) of Compound C is dissolved in 100 mL of tetrahydrofuran, 18.9 g (0.165 mol) of methanesulfonyl chloride is added. To the resulting mixture is added 8.9 g of sodium hydride (in oil, content: from 50 to 72%), followed by stirring at a reaction temperature of 65° C. for 5 hours. To the reaction mixture are added 10 mL of methanol, 1000 mL of ethyl acetate, and 500 mL of saturated saline and the resulting mixture is allowed to stand. After removal of the water layer, the ethyl acetate layer is washed with 500 mL of saturated saline, and then dried over anhydrous magnesium sulfate. Magnesium sulfate is filtered off and the filtrate is distilled under reduced pressure. The residue is purified by silica gel column chromatography to yield 5.5 g of Compound E as colorless microcrystals. Yield: 39%.

(3) Synthesis of Compound G

After 13.3 g (0.1 mol) of Compound F is suspended in 20 mL of isopropyl alcohol and 15 mL of water, 6.6 g of 85% potassium hydroxide is added to dissolve it in the suspension. Under ice cooling, 16.4 g (0.105 mol) of ethyl iodide is added dropwise while maintaining the reaction temperature at 25° C. or less. Stirring is then conducted for 2 hours at a reaction temperature of 60° C. and the reaction mixture is poured into 400 mL of cold water. Stirring is performed for further 30 minutes. Crystals thus precipitated are collected by filtration, rinsed sufficiently with water, and dried to yield 15.2 g of Compound G as pale yellow crystals. Yield: 94%.

(4) Synthesis of D5-23

Compound G (2.8 g, 0.017 mol) is dissolved in 350 mL of phosphoric acid. While maintaining the internal temperature at 5° C. or less, 1.3 g (0.19 mol) of sodium nitride is added gradually. The resulting mixture is stirred for 30 minutes. A solution obtained by dissolving 4.8 g (0.19 mol) of Compound E in 50 mL of acetic acid is added dropwise to the reaction mixture and the resulting mixture is stirred at 10° C. for 5 hours. To the reaction mixture is added 2 L of water, followed by stirring for one hour. Crystals thus precipitated are collected by filtration and rinsed sufficiently with water. Crystals thus obtained are dried and purified by silica gel column chromatography. After crystallization from 150 mL of a 1:1 (volume ratio) mixture of methanol and water and filtration, the crystals are washed with 50 mL of the same solvent mixture and dried to yield 2.8 g of Dissociative azo dye D5-23 as orange crystals. Yield: 39%.

Melting point: from 257 to 258° C., absorption maximum λmax in DMF: 546.1 nm, molar absorption coefficient ε: 41,200, $pK_a$ in 1:1 (volume ratio) mixture of DMF and water: 2.91

Synthesis Example 5-2

In accordance with the following reaction scheme, Dissociative azo dye D5-26 is synthesized.

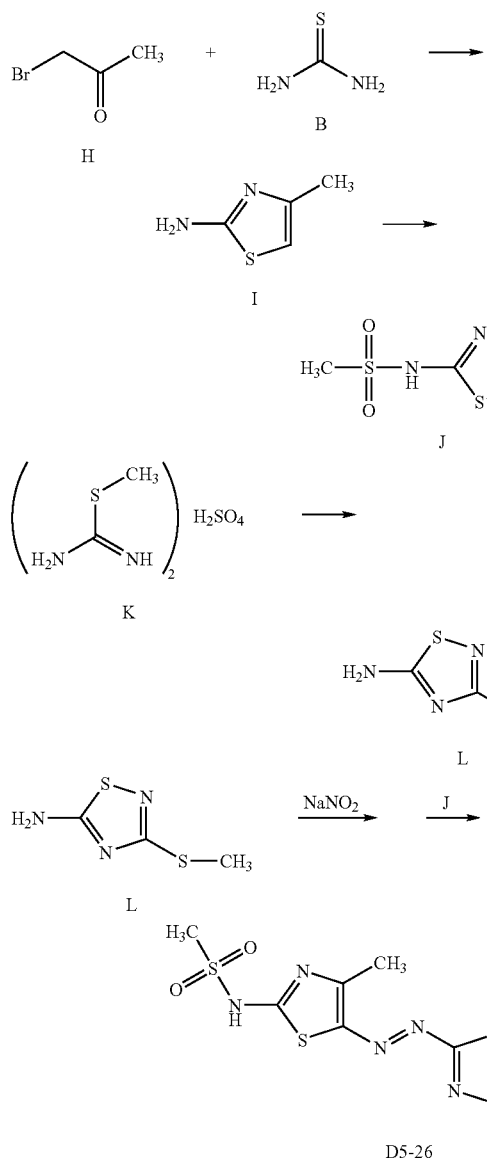

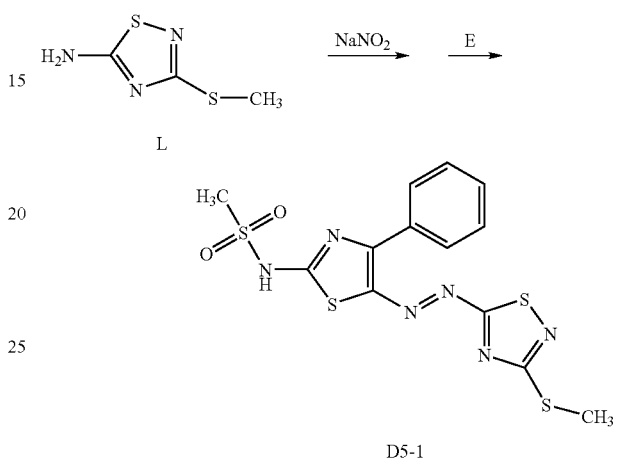

(1) Synthesis of Compound J

In a similar manner to that employed in (1) and (2) of Synthesis Example 5-1 except that Compound H is used instead of Compound A, Compound J is obtained.

(2) Synthesis of Compound L

After 10.5 g (0.13 mol) of sodium thiocyanate is dissolved in 100 mL of methanol, 13.9 g (0.05 mol) of Compound K is added to the resulting solution under cooling with ice/methanol. Then, 15.4 mL (0.11 ml) of triethylamine is added. While maintaining the internal temperature at 5° C. or less, 14 mL (0.1 mol) of triethylamine and 16.3 g (0.102 mol) of bromine are added dropwise simultaneously. After reaction at room temperature for 2 hours, the reaction mixture is poured into 1000 mL of cold water and the resulting mixture is stirred for 30 minutes. Crystals thus precipitated are filtered, rinsed sufficiently with water, and dried to yield 10.0 g of Compound L as pale yellow crystals.

Yield: 68%.

(3) Synthesis of D5-26

In a similar manner to that employed in (4) of Synthesis Example 5-1 except that Compound L and Compound J are used instead of Compound G and Compound E, respectively, Dissociative azo dye D5-26 is obtained.

Synthesis Example 5-3

In accordance with the following reaction scheme, Dissociative azo dye D5-1 is synthesized.

In a similar manner to that employed in (3) of Synthesis Example 5-2 except Compound E is used instead of Compound J, Dissociative azo dye D5-1 is obtained.

Example 5-1

The first part of the two-part hair dye shown in Table 28 and 6 mass % aqueous hydrogen peroxide (second part) are prepared. The first part, the second part, and purified water are mixed at a mass ratio of 4:7:1 to yield a hair dye composition. To 1 g of goat hair is applied 1 g of the hair dye composition at 30° C. After being allowed to stand for 30 minutes, the resulting goat hair is washed with water and a shampoo, and then dried.

After hair dyeing, the chromaticities of the tress before and after coloring treatment are measured as described above and a chromaticity change $\Delta E^*$ is calculated. As a result, the $\Delta E^*$ was 50.6.

TABLE 28

| (Mass %) | Example 5-1 |
| --- | --- |
| Dye D5-23 | 1.2 |
| Aqueous ammonia (28%) | 9.0 |
| Purified water | Balance |
| Total | 100.0 |

Examples 5-2 to 5-4

The foam-type one-part hair dyes shown in Table 29 are prepared. To 1 g of a tress made of human hair and containing 10% of gray hair, an equal amount of each of the hair dye compositions is applied. After being allowed to stand for 30 minutes, the hair is washed with water and a shampoo, and dried.

TABLE 29

| (Mass %) | Example 5-2 | Example 5-3 | Example 5-4 |
|---|---|---|---|
| D5-23 | 0.3 | — | 0.1 |
| D5-26 | — | 0.3 | — |
| D5-1 | — | — | 0.2 |
| Basic red 76 | 0.3 | — | 0.3 |
| Basic blue 99 | — | 0.2 | — |
| Ammonia (28%) | 8.0 | 8.0 | 8.0 |
| Isopropyl alcohol | 3.5 | 3.5 | 3.5 |
| Polyoxyethylene lauryl ether (23E.O) | 0.5 | 0.5 | 0.5 |
| Benzyl alcohol | — | — | 8.0 |
| Oleic acid | 7.5 | 7.5 | 7.5 |
| LPG (4.0 kg/cm$^2$) | 10.0 | 10.0 | 10.0 |
| Purified water | Balance | Balance | Balance |
| Total | 100.0 | 100.0 | 100.0 |

Examples 5-5 to 5-8

The first part of each of the cream-type two-part hair dyes shown in Table 30 is prepared and the first part and the common second part (Table 5) are mixed at a 1:1 mass ratio to yield a hair dye composition. To 1 g of a tress made of human hair and containing 10% of gray hair, an equal amount of the hair dye composition is applied. After being allowed to stand for 30 minutes, the tress is washed with water and a shampoo, and then dried.

TABLE 30

| (Mass %) | Example 5-5 | Example 5-6 | Example 5-7 | Example 5-8 |
|---|---|---|---|---|
| D5-23 | 0.5 | 0.3 | 0.1 | 0.1 |
| D5-26 | — | — | — | 0.2 |
| D5-1 | — | 0.2 | 0.3 | — |
| Toluene-2,5-diamine sulfate | — | 0.1 | 0.4 | — |
| Para-aminophenol | — | 0.1 | — | 0.1 |
| Meta-aminophenol | — | 0.2 | 0.2 | — |
| 5-Amino-ortho-cresol | — | — | 0.2 | 0.1 |
| Ammonia (28%) | 6.0 | 6.0 | 6.0 | 6.0 |
| Stearyl alcohol | 8.0 | 8.0 | 8.0 | 8.0 |
| Cocamide MEA | 4.5 | 4.5 | 4.5 | 4.5 |
| Glyceryl stearate (SE) | 1.3 | 1.3 | 1.3 | 1.3 |
| Ceteareth-30 | 4.0 | 4.0 | 4.0 | 4.0 |
| Na Lauryl sulfate | 1.0 | 1.0 | 1.0 | 1.0 |
| Oleic acid | 2.0 | 2.0 | 2.0 | 2.0 |
| Propylene glycol | 1.5 | 1.5 | 1.5 | 1.5 |
| PEG-9 Dimethicone*[1] | 1.5 | 1.5 | 1.5 | 1.5 |
| Hydrolyzed keratin | 0.5 | 0.5 | 0.5 | 0.5 |
| Panthenol | 0.8 | 0.8 | 0.8 | 0.8 |
| EDTA-4Na | 0.5 | 0.5 | 0.5 | 0.5 |
| Ammonium chloride | q.s.*[2] | q.s.*[2] | q.s.*[2] | q.s.*[2] |
| Purified water | Balance | Balance | Balance | Balance |
| Total | 100.0 | 100.0 | 100.0 | 100.0 |

*[1]"KF-6005", product of Shin-etsu Chemical
*[2]Amount to adjust pH to 10

Examples 5-9 to 5-12

The first part of each of the two-part hair dyes shown in Table 31 is prepared and the first part and the common second part (Table 5) are mixed at a 1:1 mass ratio to yield a hair dye composition. To 1 g of a tress made of human hair and containing 100 of gray hair, an equal amount of the hair dye composition is applied. After being allowed to stand for 30 minutes, the tress is washed with water and a shampoo, and then dried.

TABLE 31

| (Mass %) | Example 5-9 | Example 5-10 | Example 5-11 | Example 5-12 |
|---|---|---|---|---|
| D5-23 | 0.3 | 0.1 | 0.3 | 0.1 |
| D5-26 | — | — | 0.2 | — |
| D5-1 | — | 0.2 | — | — |
| Direct dye X | — | — | 0.3 | — |
| Direct dye Y | — | — | — | 0.4 |
| Direct dye Z | — | 0.5 | — | — |
| Toluene-2,5-diamine sulfate | 0.2 | 0.3 | — | 0.2 |
| Para-aminophenol | — | — | 0.1 | — |
| Meta-aminophenol | 0.2 | — | 0.1 | — |
| 5-Amino-ortho-cresol | — | 0.3 | — | 0.2 |
| Behentrimonium chloride | 2.1 | 2.1 | 2.1 | 2.1 |
| Mineral oil | 0.5 | 0.5 | 0.5 | 0.5 |
| Propylene glycol | 7.0 | 7.0 | 7.0 | 7.0 |
| Cetearyl alcohol | 7.0 | 7.0 | 7.0 | 7.0 |
| Aqueous ammonia (28%) | 6.5 | 6.5 | 6.5 | 6.5 |
| Polyquaternium-10*[4] | 1.0 | — | — | 1.0 |
| Amodimethicone*[5] | 1.5 | 1.5 | 1.5 | — |
| Purified water | Balance | Balance | Balance | Balance |
| Total | 100.0 | 100.0 | 100.0 | 100.0 |

Direct dye X

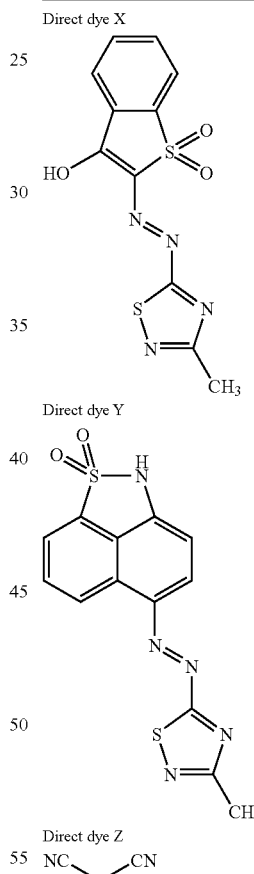

Direct dye Y

Direct dye Z

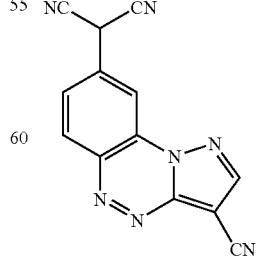

*[4]"Ucare Polymer JR-400", product of Amerchol
*[5]"SM8704C", product of Dow Corning Toray

Examples 5-13 to 5-16

The first part and the booster solution of each of the two-part hair dyes shown in Table 32 are prepared and the first part, the booster solution, and the common second part (Table 5) are mixed at a 1:1:0.1 mass ratio to yield a hair dye composition. To 1 g of a tress made of human hair and containing 10% of gray hair, an equal amount of the hair dye composition is applied. After being allowed to stand for 30 minutes, the tress is washed with water and a shampoo, and then dried.

TABLE 32

| | (Mass %) | Example 5-13 | Example 5-14 | Example 5-15 | Example 5-16 |
|---|---|---|---|---|---|
| First part | D5-3 | 0.5 | 0.4 | 0.3 | 0.1 |
| | D5-6 | — | 0.2 | — | 0.2 |
| | D5-11 | — | 0.2 | — | 0.2 |
| | HC red 3 | 1.0 | — | 0.3 | — |
| | Basic blue 99 | — | 1.0 | — | 0.1 |
| | Para-aminophenol | — | 0.2 | 0.2 | 0.1 |
| | Toluene-2,5-diamine sulfate | 0.2 | — | 0.4 | — |
| | 5-Amino-ortho-cresol | — | 0.2 | 0.2 | 0.1 |
| | Meta-aminophenol | 0.2 | — | 0.2 | — |
| | Behentrimonium chloride | 2.1 | 2.1 | 2.1 | 2.1 |
| | Mineral oil | 0.5 | 0.5 | 0.5 | 0.5 |
| | Propylene glycol | 7.0 | 7.0 | 7.0 | 7.0 |
| | Cetearyl alcohol | 7.0 | 7.0 | 7.0 | 7.0 |
| | Aqueous ammonia (28%) | 6.5 | 6.5 | 6.5 | 6.5 |
| | Polyquaternium-10*[6] | 1.0 | — | 1.0 | — |
| | Amodimethicone*[7] | 1.5 | 1.5 | 1.5 | 1.5 |
| | Purified water | Balance | Balance | Balance | Balance |
| | Total | 100.0 | 100.0 | 100.0 | 100.0 |
| Booster solution | D5-23 | 1.0 | 0.6 | — | 0.4 |
| | Direct dye X | — | 0.4 | 1.5 | — |
| | Aqueous ammonia (28%) | 2.0 | 2.0 | 2.0 | 2.0 |
| | PEG-8 | 3.0 | 3.0 | 3.0 | 3.0 |
| | Purified water | Balance | Balance | Balance | Balance |
| | Total | 100.0 | 100.0 | 100.0 | 100.0 |

*[6]"Ucare Polymer JR-400", product of Amerchol
*[7]"SM8704C", product of Dow Corning Toray

Examples 5-17 to 5-19

In a manner known per se in the art, the first part and the third part of each of the cream-type three-part hair dyes shown in Table 33 are prepared. The first part, the common second part (Table 5) and the third part are mixed at a 1:1:0.3 mass ratio to yield a hair dye composition. To 1 g of a tress made of human hair and containing 10% of gray hair, an equal amount of the hair dye composition is applied. After being allowed to stand for 30 minutes, the tress is washed with water and a shampoo, and then dried.

TABLE 33

| | (Mass %) | Example 5-17 | Example 5-18 | Example 5-19 |
|---|---|---|---|---|
| First part | D5-27 | 0.3 | — | 0.3 |
| | Toluene-2,5-diamine sulfate | 0.2 | 0.4 | — |
| | Para-aminophenol | 0.2 | — | 0.3 |
| | Meta-aminophenol | 0.4 | 0.2 | — |
| | 5-Amino-ortho-cresol | — | 0.2 | 0.3 |
| | Ammonia (28%) | 8.0 | 8.0 | 8.0 |
| | Stearyl alcohol | 8.0 | 8.0 | 8.0 |
| | Cocamide MEA | 4.5 | 4.5 | 4.5 |
| | Glyceryl stearate (SE) | 1.3 | 1.3 | 1.3 |
| | Ceteareth-30 | 4.0 | 4.0 | 4.0 |
| | Na Lauryl sulfate | 1.0 | 1.0 | 1.0 |
| | Oleic acid | 2.0 | 2.0 | 2.0 |
| | Propylene glycol | 1.5 | 1.5 | 1.5 |
| | PEG-9 Dimethicone*[8] | 1.5 | — | — |
| | Hydrolyzed keratin | 0.5 | 0.5 | 0.5 |
| | Panthenol | 0.8 | 0.8 | 0.8 |
| | EDTA-4Na | 0.5 | 0.5 | 0.5 |
| | Ammonium chloride | q.s.*[9] | q.s.*[9] | q.s.*[9] |
| | Purified water | Balance | Balance | Balance |
| | Total | 100.0 | 100.0 | 100.0 |
| Third part | D5-23 | — | 0.5 | 0.3 |
| | Ammonium persulfate (g)*[10] | 5.0 | 5.0 | 5.0 |

*[8]"KF-6005" product of Shin-etsu Chemical
*[9]Amount to adjust pH to 10
*[10]Purity: 95% (in the form of powder)

The invention claimed is:

1. A hair dye composition comprising:

(a) an azo dye represented by any one of the following formulas (1) to (5):

(1)

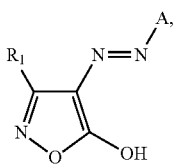

wherein $R_1$ represents a hydrogen atom or a substituent and A represents a monocyclic or bicyclic, aromatic heterocyclic residue which may have a substituent and has a free valence at a carbon atom of the residue, with the proviso that $R_1$ and A each contains, in the structure thereof, none of a carboxy group, a sulfo group and a quaternary ammonium group, (2)

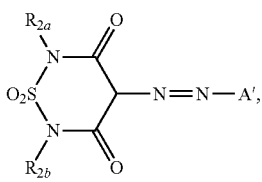

wherein $R_{2a}$ and $R_{2b}$ each represents a hydrogen atom or a substituent, and A' represents a monocyclic or bicyclic, aromatic heterocyclic residue which may have a substituent and has a free valence at a carbon atom of the residue, with the proviso that $R_{2a}$, $R_{2b}$, and A' each contains, in the structure thereof, none of a carboxy group, a sulfo group, and a quaternary ammonium group, (3)

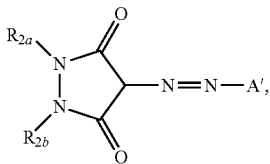

wherein $R_{2a}$, $R_{2b}$, and A' have the same meanings as defined above, (4)

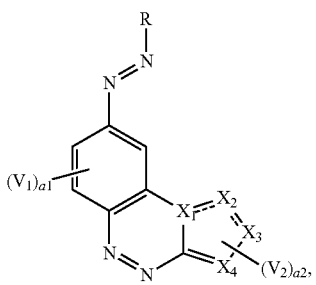

wherein R represents a coupler component, $X_1$, $X_2$, $X_3$, and $X_4$ represent atoms which are coupled together with the carbon atom sandwiched between $X_1$ and $X_4$ to form a 5-membered heteroaromatic ring, $V_1$ and $V_2$ each represents a substituent, and a1 and a2 each stands for an integer from 0 to 3, and (5)

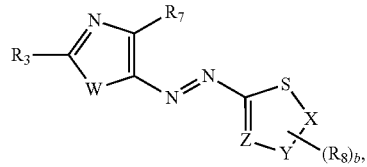

wherein $R_3$ represents a hydroxy group, an alkylsulfonylamino group, an arylsulfonylamino group, or —CH($R_4$)($R_5$), $R_4$ and $R_5$ each representing a substituent having a Hammett's constant σ of 0.2 or greater and less than 1.4, W represents a sulfur atom or N—$R_6$, $R_6$ representing a substituent, X, Y and Z each represents a nitrogen atom or a carbon atom, with the proviso that at least one of X, Y and Z is a nitrogen atom and when Z represents a nitrogen atom, either one or both of X and Y represent a nitrogen atom, $R_7$ and $R_8$ each represents a substituent, and b stands for from 0 to 2, with the proviso that when b stands for 2, two $R_8$s may be coupled to form an aromatic ring or a heteroaromatic ring, and (b) at least one dyeing ingredient selected from the group consisting of an oxidizing agent, oxidation dye, and a direct dye.

2. The hair dye composition according to claim 1, wherein in the azo dye represented by the formula (1), $R_1$ represents a hydrogen atom or a substituent selected from the group consisting of halogen atoms, alkyl groups, aryl groups, heterocyclic groups, a cyano group, a hydroxy group, a nitro group, alkoxy groups, aryloxy groups, silyloxy groups, heterocyclic oxy groups, acyloxy groups, carbamoyloxy groups, alkoxycarbonyloxy groups, aryloxycarbonyloxy groups, an amino group, acylamino groups, ureido groups, alkoxycarbonylamino groups, aryloxycarbonylamino groups, sulfamoylamino groups, alkylsulfonylamino groups, arylsulfonylamino groups, alkylthio groups, arylthio groups, heterocyclic thio groups, a sulfamoyl group, alkylsulfinyl groups, arylsulfinyl groups, alkylsulfonyl groups, arylsulfonyl groups, acyl groups, aryloxycarbonyl groups, alkoxycarbonyl groups, a carbamoyl group, and imido groups; and A is a residue of an aromatic heterocycle selected from the group consisting of a pyrrole ring, a thiophene ring, a furan ring, an oxazole ring, a pyrazole ring, an imidazole ring, an isoxazole ring, a thiadiazole ring, a thiazole ring, an isothiazole ring, a triazole ring, an oxadiazole ring, a benzoxazole ring, a benzisoxazole ring, a benzothiazole ring, a benzisothiazole ring, and a benzimidazole ring.

3. The hair dye composition according to claim 1, wherein in the azo dye represented by the formula (1), $R_1$ represents an alkyl group, an aryl group, a heterocyclic group, or an alkoxycarbonyl group, and A represents a residue of a benzisothiazole ring, a pyrazole ring, an isothiazole ring, or a thiadiazole ring.

4. The hair dye composition according to claim 1, wherein in the azo dye represented by the formula (2), $R_{2a}$ and $R_{2b}$ each represents a hydrogen atom or a substituent selected from the group consisting of alkyl groups, aryl groups, heterocyclic groups, alkylsulfonyl groups, arylsulfonyl groups, acyl groups, aryloxycarbonyl groups, alkoxycarbonyl groups, and carbamoyl groups; and A' represents a residue of an aromatic heterocycle selected from the group consisting of a pyrrole ring, a thiophene ring, a furan ring, an oxazole ring, a pyrazole ring, an imidazole ring, an isoxazole ring, a thiadiazole ring, an isothiazole ring, a triazole ring, an oxadiazole ring, a benzoxazole ring, a benzisoxazole ring, a benzothiazole ring, a benzisothiazole ring, and a benzimidazole ring.

5. The hair dye composition according to claim 1, wherein in the azo dye represented by the formula (2), $R_{2a}$ and $R_{2b}$ each represents a hydrogen atom, an alkyl group, or an aryl group and A' represents a residue of a benzisothiazole ring, an isothiazole ring, or a thiadiazole ring.

6. The hair dye composition according to claim 1, wherein in the azo dye represented by the formula (3), $R_{2a}$ and $R_{2b}$ each represents a hydrogen atom or a substituent selected from the group consisting of alkyl groups, aryl groups, heterocyclic groups, alkylsulfonyl groups, arylsulfonyl groups, acyl groups, aryloxycarbonyl groups, alkoxycarbonyl groups, and carbamoyl groups; and A represents a residue of an aromatic heterocycle selected from the group consisting of a pyrrole ring, a thiophene ring, a furan ring, an oxazole ring, a pyrazole ring, an imidazole ring, an isoxazole ring, a thiadiazole ring, an isothiazole ring, a triazole ring, an oxadiazole ring, a benzoxazole ring, a benzisoxazole ring, a benzothiazole ring, a benzisothiazole ring, and a benzimidazole ring.

7. The hair dye composition according to claim 1, wherein in the azo dye represented by the formula (3), $R_{2a}$ and $R_{2b}$ each represents a hydrogen atom, an alkyl group, an aryl group, or an acyl group and A represents a residue of a benzisothiazole ring, an isothiazole ring, or a thiadiazole ring.

8. The hair dye composition according to claim 1, wherein in the azo dye represented by the formula (4), $X_1$, $X_2$, $X_3$ and $X_4$ are any one of a combination (i) of a carbon atom, a nitrogen atom, a sulfur atom, and a carbon atom, a combination (ii) of a nitrogen atom, a nitrogen atom, a carbon atom, and a carbon atom, and a combination (iii) of a nitrogen atom, a carbon atom, a carbon atom, and a nitrogen atom, the atoms being arranged in the order of $X_1$, $X_2$, $X_3$ and $X_4$.

9. The hair dye composition according to claim 1, wherein in the azo dye represented by the formula (4), a coupler component R is a group represented by the following formula (C):

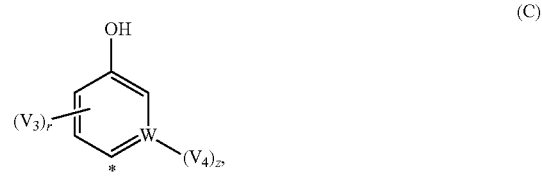

wherein symbol * means a carbon atom to be bonded to an azo portion of the formula (4), $V_3$ represents a substituent, r stands for an integer from 0 to 3, $V_4$ represents a hydrogen atom or a substituent, and W represents a carbon atom or a nitrogen atom, with the proviso that when W represents a carbon atom, z stands for 1 and when W represents a nitrogen atom, z stands for 0.

10. The hair dye composition according to claim 1, wherein in the azo dye represented by the formula (5), X represents a carbon atom, and Y and Z each represents a nitrogen atom, or X and Z each represents a nitrogen atom and Y represents a carbon atom.

11. The hair dye composition according to claim 1, wherein in the azo dye represented by the formula (5), $R_7$ represents an alkyl group or an aryl group.

12. The hair dye composition according to claim 1, wherein in the azo dye represented by the formula (5), $R_3$ represents an alkylsulfonylamino group, W represents a sulfur atom, and b stands for 1.

13. The hair dye composition according to claim 1, further comprising an oxidizing agent.

14. A hair dyeing method comprising applying a hair dye composition as claimed in claim 1 to hair.

* * * * *